US012605356B2

(12) United States Patent     (10) Patent No.:   US 12,605,356 B2

Indolfi et al.     (45) Date of Patent:    Apr. 21, 2026

(54) METHODS OF TREATING PANCREATIC CANCER

(71) Applicant: PanTher Therapeutics, Inc., Watertown, MA (US)

(72) Inventors: Laura Indolfi, Boston, MA (US); Margaret Lashof-Sullivan, Watertown, MA (US)

(73) Assignee: PanTher Therapeutics, Inc., Watertown, MA (US)

( * ) Notice: Subject to any disclaimer, the term of this patent is extended or adjusted under 35 U.S.C. 154(b) by 319 days.

(21) Appl. No.: 18/495,476

(22) Filed: Oct. 26, 2023

(65) Prior Publication Data

US 2024/0165071 A1     May 23, 2024

Related U.S. Application Data

(60) Provisional application No. 63/384,145, filed on Nov. 17, 2022.

(51) Int. Cl.
*A61K 31/337*     (2006.01)
*A61K 9/00*     (2006.01)
    (Continued)

(52) U.S. Cl.
CPC .......... *A61K 31/337* (2013.01); *A61K 9/0024* (2013.01); *A61K 9/7007* (2013.01); *A61K 47/34* (2013.01); *A61P 35/04* (2018.01)

(58) Field of Classification Search
CPC .......... A61K 31/337; A61K 9/24; A61P 35/00
See application file for complete search history.

(56) References Cited

U.S. PATENT DOCUMENTS 5,716,981 A    2/1998   Hunter et al.
7,994,213 B2   8/2011   Shin et al.
      (Continued)

FOREIGN PATENT DOCUMENTS

CN     102727944 A    10/2012
EP      2005980 A2    12/2008
      (Continued)

OTHER PUBLICATIONS

International Preliminary Report on Patentability for PCT Application No. PCT/US2023/077896, issued on Apr. 29, 2025, 7 pages.
      (Continued)

*Primary Examiner* — Carlos A Azpuru
(74) *Attorney, Agent, or Firm* — GOODWIN PROCTER LLP

(57)        ABSTRACT

Provided are implantable and biodegradable drug delivery devices capable of delivering an active pharmaceutical ingredient (API) directly to a target pancreatic tumor tissue. The drug delivery devices can include at least two layers. One of the layers can include the API and a biodegradable polymer and a second layer can include another biodegradable polymer that degrades slower than the first biodegradable polymer. When the device is placed directly on the target tissue, the API layer can degrade thereby releasing the API towards the target tissue while the non-API layer can prevent the API from being released away from the target tissue onto non-target tissue.

16 Claims, 70 Drawing Sheets

(51) Int. Cl.

| | | |
|---|---|---|
| *A61K 9/70* | (2006.01) | |
| *A61K 47/34* | (2017.01) | |
| *A61P 35/04* | (2006.01) | |

(56) References Cited

U.S. PATENT DOCUMENTS

| | | | |
|---|---|---|---|
| 8,017,143 | B2 | 9/2011 | Shin et al. |
| 8,043,355 | B2 | 10/2011 | Shin et al. |
| 9,301,926 | B2 * | 4/2016 | Indolfi .................. A61L 31/148 |
| 10,610,346 | B2 | 4/2020 | Schwartz |
| 10,888,530 | B2 | 1/2021 | Schwartz et al. |
| 2005/0271701 | A1 | 12/2005 | Cottone et al. |
| 2007/0178138 | A1 * | 8/2007 | Pal .......................... A61P 19/02 |
| | | | 604/500 |
| 2008/0051882 | A1 | 2/2008 | Rubin |
| 2008/0167724 | A1 | 7/2008 | Ruane et al. |
| 2009/0099646 | A1 | 4/2009 | Matsuda et al. |
| 2010/0021519 | A1 | 1/2010 | Shenoy |
| 2011/0045055 | A1 | 2/2011 | Hingston et al. |
| 2011/0264190 | A1 | 10/2011 | McClain et al. |
| 2012/0128732 | A1 | 5/2012 | Trieu et al. |
| 2012/0150282 | A1 | 6/2012 | Adden et al. |
| 2012/0323311 | A1 | 12/2012 | McClain |
| 2013/0084322 | A1 | 4/2013 | Wu |
| 2013/0142875 | A1 | 6/2013 | Shemi et al. |
| 2013/0209538 | A1 | 8/2013 | Venkatraman et al. |
| 2013/0236498 | A1 | 9/2013 | Mangiardi |
| 2013/0280316 | A1 | 10/2013 | Pal et al. |
| 2014/0308336 | A1 | 10/2014 | Indolfi et al. |
| 2016/0175491 | A1 | 6/2016 | Indolfi et al. |
| 2022/0054719 | A1 | 2/2022 | Indolfi et al. |
| 2023/0149299 | A1 | 5/2023 | Indolfi et al. |

FOREIGN PATENT DOCUMENTS

| | | | |
|---|---|---|---|
| EP | 2238993 | A2 | 10/2010 |
| EP | 1997525 | B1 | 11/2011 |
| JP | 2007-313009 | A | 12/2007 |
| JP | 2016-516780 | A | 6/2016 |
| JP | 2020-536955 | A | 12/2020 |
| JP | 2021-511191 | A | 5/2021 |
| WO | 2008070996 | A1 | 6/2008 |
| WO | 2012/021108 | A1 | 2/2012 |
| WO | 2014/036290 | * | 3/2014 |
| WO | 2014036290 | A1 | 3/2014 |
| WO | 2019067991 | A1 | 4/2019 |
| WO | 2021151156 | A1 | 8/2021 |
| WO | 2023/091976 | * | 5/2022 |
| WO | 2022177993 | A1 | 8/2022 |
| WO | 2023091976 | A1 | 5/2023 |

OTHER PUBLICATIONS

International Search Report and Written Opinion for International Application No. PCT/US2023/070726 mailed Oct. 16, 2023, 10 pages.

International Preliminary Report on Patentability for International Application No. PCT/US2023/070726 mailed on Feb. 6, 2025, 5 pages.

International Preliminary Report on Patentability for PCT Application No. PCT/US2022/079996, mailed on May 30, 2024, 6 pages.

Lu et al., "Effects of Amphiphilic PCL-PEG-PCL Copolymer Addition on 5-Fluorouracil Release from Biodegradable PCL Films for Stent Application," International Journal of Pharmaceutics, 2011, 419:77-84.

Ranganath, "The Use of Submicron/Nanoscale PLGA Implants to Deliver Paclitaxel with Enhanced Pharmacokinetics and Therapeutic Efficacy in Intracranial Glioblastoma in Mice," Biomaterials, 2010, 31: 5199-5207.

Database WPI, week 201335; AN 2013-BC3395, CN 1027227944A, Oct. 17, 2012, XP00272811 (18 pages).

PCT International Search Report and Written Opinion for PCT Application No. PCT/US2014/033671 mailed Aug. 12, 2014 (12 pages).

Chung, M. J. et al., "Safety evaluation of self-expanding metallic biliary stents eluting gemcitabine in a porcine model," Journal of Gastroenterology and Hepatology 27 (2012) 261-267.

ClinicalTrials.gov, "Patency and Safety of the Drug Eluting Covered Biliary Stent Comparing to the Common Covered Biliary Stent (MIRA-cover)," (available at http://clinicaltrials.gov/ct2/show/study/ NCT01512563) last updated Jan. 15, 2012.

Conroy, T. et al.,"Folfirinox versus Gemcitabine for Metastatic Pancreatic Cancer," The New England Journal of Medicine, 364:1817-25 (2011).

Guo, S.R. et al., "In vivo evaluation of 5-fluorouracil-containing self-expandable nitinol stent in rabbits: Efficiency in long-term local drug delivery," J Pharm Sci. Jul. 2010; 99(7):3009-18.

Hair, Clark D. et al., "Future developments in biliary stenting," Clinical and Experimental Gastroenterology 2013:6 91-99.

Han, Young-Min et al., "Polyurethane-Covered Self-Expandable Nitinol Stent for Malignant Biliary Obstruction: Preliminary Results," Cardiovasc Intervent Radial (2002) 25:381-382.

Indolfi, Laura et al., Study—"Design of a Drug Eluting Stent for treatment of pancreatic malignancy," Abstract, Society for biomaterials (2013).

Lee et al., "The Effect on Porcine Bile Duct of a Metallic Stent Covered with a Paclitaxel-Incorporated Membrane," Gastrointest. Endosc. 61 (2):296-301, Feb. 2005.

Ligorio, Matteo et al., "A novel drug-eluting platform for localized treatment of pancreatic cancer," Abstract, American Association for Cancer Research, Annual Meeting 2014, Apr. 5-9, 2014.

Si, Jang et al., "Porcine feasibility and safety of a new paclitaxel-eluting biliary stent with a Pluronic-containing membrane," Endoscopy 2012; 44:825-831.

Taewoong Medical, Taewoong Niti-STM biliary stents (available at http://www.stent.net/new/sub.php?localNum=2&pageNum=1 &subNum=1 &subNum2=2) accessed Oct. 23, 2013.

Caves et al., "The Evolving Impact of Microfabrication and Nanotechnology on Stent Design," Journal of Vascular Surgery, 2006, pp. 1363-1368.

Jang et al., "Efficacy of a Metallic Stent Covered with a Paclitaxel-Incorporated Membrane Versus a Covered Metal Stent for Malignant Biliary Obstruction: A Prospective Comparative Study," Dig. Dis. Sci., 2013, 58:865-871.

Fredenberg et al. "The mechanisms of drug release in poly9lactic-co-glycolic acid)-based drug delivery systems—A review." Int'l J. Pharmaceutics, vol. 415, Issues 1-2, pp. 34-52 (Aug. 2011 ).

"Flexible", Merriam_Webster Dictionary, available at https://www. merriam-webster.com/dictionary/flexible, accessed on Oct. 31, 2023.

Jackon, J.K., et al., "Characterization of perivascular poly(lactic-co-glycolic acid) films containing paclitaxel," International Journal of Pharmaceutics 283 (2004) 97-109 (Year: 2004).

Lu, L., et al., "In vitro degradation of thin poly(DL-lactic-co-glycolicacid) films," J. Biomed. Mater. Res., 46: 236-244 (1999) (Year: 1999).

Liu, R., et al., "Prevention of Local Tumor Recurrence Following Surgery Using Low-Dose Chemotherapeutic Polymer Films", Ann Surg Oneal (2010) 17:1203-1213 (Year: 2010).

Chun, H.J., et al., "Gastrointestinal and biliary stents", J. Gastroenterology and Hepatology 25 (2010) 234-243 (Year: 2010).

International Preliminary Report on Patentability for International Application No. PCT/US2023/070726 mailed Feb. 6, 2025, 5 pages.

International Search Report and Written Opinion mailed Feb. 20, 2024, directed to International Application No. PCT/US2023/ 077767, 13 pages.

Australian New Zealand Clinical Trials Registry. (Jul. 8, 2021) "A Phase 1 Study of PTM-101 as Neoadjuvant Therapy for Borderline Resectable or Locally Advanced Pancreatic Ductal Adenocarcinoma (PDAC)," located at www.anzctr.org.au/Trial/Registration/TrialReview. aspx?id=38152&isReview=true, visited on Apr. 3, 2023. (6 pages).

BioSpace. (Oct. 6, 2021) "PanTher Therapeutics Doses First Two Patients in Phase 1 Trial of PTM-101 for Treatment of Pancreatic Cancer," located at www.biospace.com/article/releases/panther-

(56) References Cited

OTHER PUBLICATIONS therapeutics-doses-first-twopatients-in-phase-1-trial-of-ptm-101-for-treatment-of-pancreatic-cancer/, visited Apr. 3, 2023. (5 pages).

Businesswire. (Aug. 2021 ). "PanTher Therapeutics Receives Ethics Approval to Initiate Phase 1 Clinical Trial of 3 PTM-101 in Australia; Announces Appointment of Chief Medical Officer"; Establishes Clinical Advisory Board, Press Release.

Indolfi et al. (Mar. 2016) "A Tunable Delivery Platform to Provide Local Chemotherapy for Pancreatic Ductal Adenocarcinoma," located at pubmed.ncbi.nlm.nih.gov/27082874, visited on Apr. 3, 2023. (2 pages).

Indolfi et al., U.S. Office Action dated Apr. 18, 2019, directed to U.S. Appl. No. 15/055,012; 14 pages.

Indolfi et al., U.S. Office Action dated Apr. 29, 2015, directed to U.S. Appl. No. 14/250,025; 10 pages.

Indolfi et al., U.S. Office Action dated Aug. 13, 2018, directed to U.S. Appl. No. 15/055,012; 17 pages.

Indolfi et al., U.S. Office Action dated Dec. 20, 2019, directed to U.S. Appl. No. 15/055,012; 23 pages.

Indolfi et al., U.S. Office Action dated May 5, 2023, directed to U.S. Appl. No. 17/520,891; 10 pages.

Indolfi et al., U.S. Office Action dated Oct. 23, 2020, directed to U.S. Appl. No. 15/055,012; 20 pages.

Indolfi, et al., U.S. Office Action dated Apr. 5, 2017, directed to U.S. Appl. No. 15/055,012; 13 pages.

Indolfi, et al., U.S. Office Action dated Oct. 27, 2017, directed to U.S. Appl. No. 15/055,012; 19 pages.

International Search Report and Written Opinion mailed Feb. 15, 2023, directed to International Application No. PCT/US2022/079996; 11 pages.

Lashof-Sullivan et al. "Targeted and Sustained Drug Delivery Therapy for Localized Pancreatic Cancer: In Vivo Validation in Porcine Models," American Association for Cancer Research Pancreatic Symposium, Sep. 7, 2019, Boston, Massachusetts; 1 page.

Lashof-Sullivan et al. (May 2020) "Novel Targeted and Sustained Drug Delivery Therapy for Localized Pancreatic Cancer: Validation in Porcine Models and Minimally Invasive Surgical Feasibility in Human Cadavers," located at ascopubs.org/doi/abs/10.1200/JCO.2020.38.15_suppl.e16747, visited on Apr. 3, 2023. (4 pages).

Mack et al., "A biodegradable filament for controlled drug delivery," Jour. Cont. Release, 2009, vol. 139, issue 3, pp. 205-211 (Year: 2009).

Vieira et al., "Natural-based plasticizers and biopolymer films: A review", Eur. Poly. Jour., 2011, vol. 47, issue 3, pp. 254-263 (Year: 2011).

Johnson and Johnson®, "Contact Lens Checklist", 2018, pp. 1-4. (Year: 2018).

International Search Report and Written Opinion for Application No. PCT/US2023/077896, mailed Mar. 1, 2024, 11 pages.

* cited by examiner

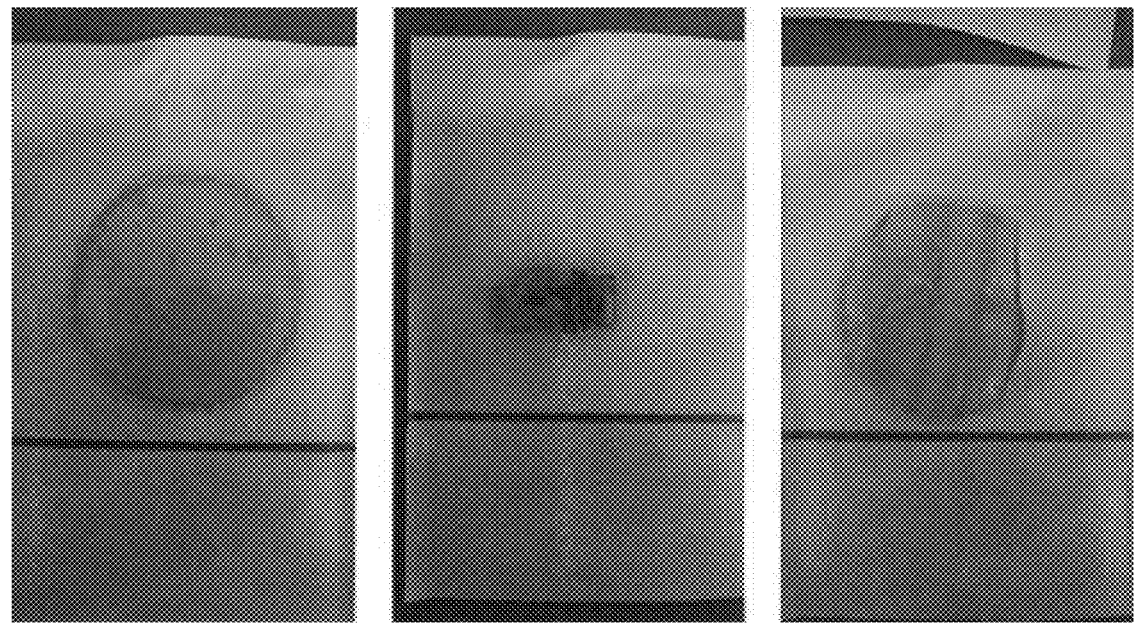
FIG. 6A                    FIG. 6B                    FIG. 6C

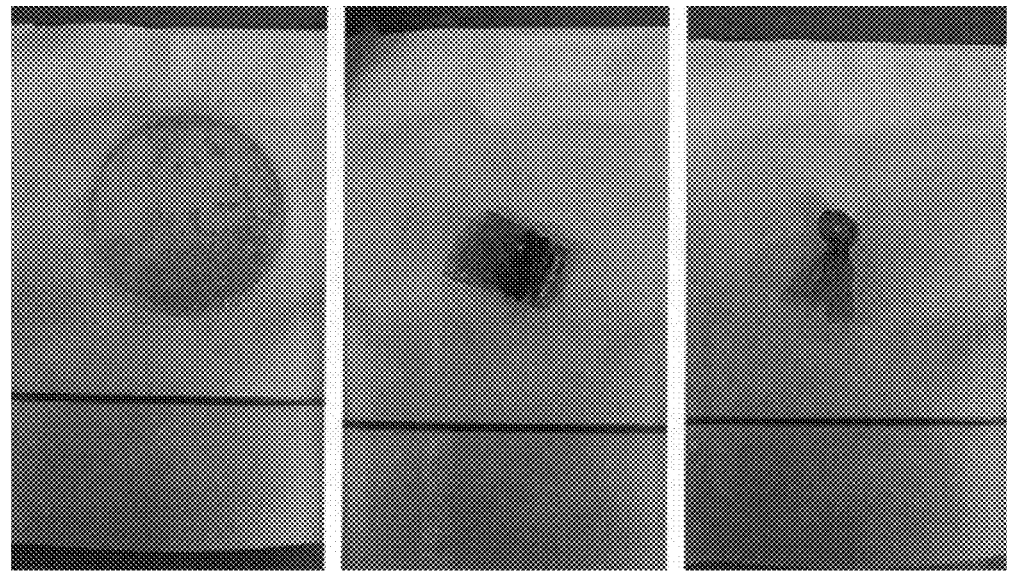
FIG. 7A                    FIG. 7B                    FIG. 7C

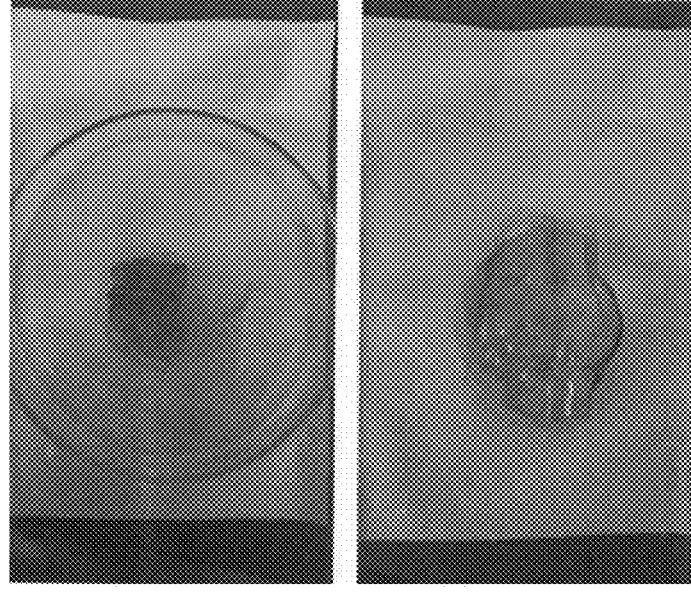
FIG. 9A                    FIG. 9B

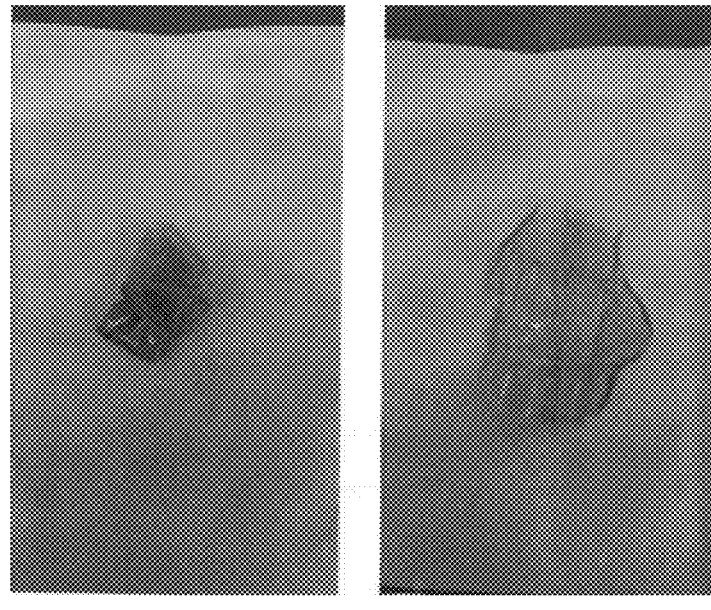
FIG. 10A                    FIG. 10B

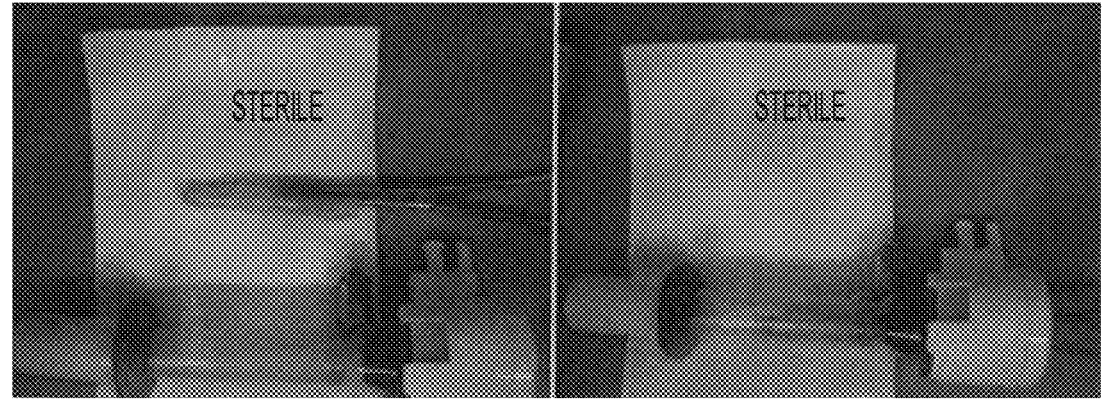
FIG. 15C                    FIG. 15D

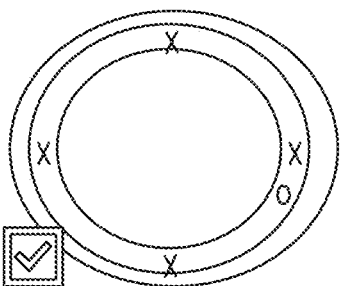
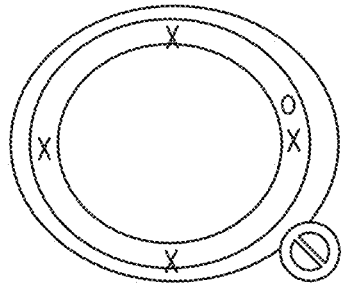
FIG. 16A                              FIG. 16B

| Disc no. | Time in fridge (weeks) | Average thickness (mm) | Standard deviation |
|---|---|---|---|
| 2 | 0 | 0.530 | 0.194 |
| 7 | 0 | 0.553 | 0.155 |
| 4 | 4 | 0.536 | 0.131 |
| 3 | 11 | 0.501 | 0.140 |

| Disc no. | Time in fridge (weeks) | Outer diameter (mm) | Std. deviation | Inner diameter (mm) | Std. deviation |
|---|---|---|---|---|---|
| 2 | 0 | 6.2 | 0 | 5.67 | 0.116 |
| 7 | 0 | 6.2 | 0 | 5.887 | 0.035 |
| 4 | 4 | 6.3 | 0 | 5.7 | 0 |
| 3 | 11 | 6.2 | 0 | 5.64 | 0.051 |

Dry thickness versus wet thickness measured at different time points

| time (days) | Avg. thickness (mm) | std. deviation |
|---|---|---|
| 0 | 0.479 | 0.026 |
| 1 | 0.472 | 0.039 |
| 7 | 0.536 | 0.031 |
| 14 | 0.551 | 0.181 |

Dry versus wet diameters measured at different time points

☐ outer diameter     ▨ inner diameter

| time (days) | Outer diameter | Inner diameter |
|---|---|---|
| 0 | 6.2 | 5.56 |
| 1 | 6.5 | 5.89 |
| 7 | 6.3 | 5.71 |
| 14 | 6.3 | 5.65 |

| | 5 day samples | |
|---|---|---|
| Before Testing | After removal from solution | Dry |
| 9.17-15 | | |
| 10.17-05 | | |
| 12.17-06 | | |

FIG. 23C

| | 2 week samples | |
|---|---|---|
| Before Testing | After removal from solution | Dry |
| 9.17-13 | | |
| 8.17-01 | | |
| 13.17-01 | | |

FIG. 23E

|  | 3 week samples |  |
|---|---|---|
| Before Testing | After removal from solution | Dry |
| 9.17-08  |  |  |
| 11.17-11 |  |  |
| 13.17-06 |  |  |

| | 4 week samples | |
|---|---|---|
| Before Testing | After removal from solution | Dry |
| 9.17-14 | | |
| 12.17-01 | | |
| 13.17-03 | | |

FIG. 23G

| | 6 week samples | |
|---|---|---|
| Before Testing | After removal from solution | Dry |
| 3.17-02 | | |
| 10.17-07 | | |
| 14.17-03 | | |

FIG. 23H

| | 8 week samples | |
|---|---|---|
| Before Testing | After removal from solution | Dry |
| 10.17-09  | | |
| 11.17-12 | | |
| 13.17-08 | | |

| | 10 week samples | |
|---|---|---|
| Before Testing | After removal from solution | Dry |
| 9.17-02 | | |
| 9.17-05 | | |
| 10.17-10 | | |

FIG. 23J

◎ Live tumor cells     ◎ Dead tumor cells     • Active agent

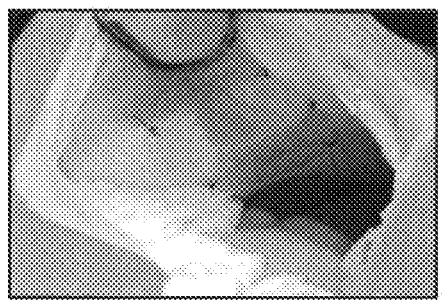   
FIG. 27A                    FIG. 27B

| Animal Number | Body Weight on Day 0 (kg) | Body Condition Score Day 0 | Body Weight at Necropsy (kg) | Body Condition Score at Necropsy | % Body Weight Change |
|---|---|---|---|---|---|
| | 55.1 | 3.0 | 71.9 | 3.0 | 30% |
| | 53.0 | 3.0 | 66.8 | 3.0 | 26% |
| | 47.8 | 3.0 | 59.1 | 3.0 | 24% |

| Animal Number | Body Weight on Day 0 (kg) | Body Condition Score Day 0 | Body Weight at Necropsy (kg) | Body Condition Score at Necropsy | % Body Weight Change |
|---|---|---|---|---|---|
| | 43.7 | 3.0 | 58.2 | 3.0 | 25% |
| | 41.6 | 3.0 | 52.2 | 3.0 | 20% |
| | 45.1 | 3.0 | 56.0 | 3.0 | 19% |

FIG. 28

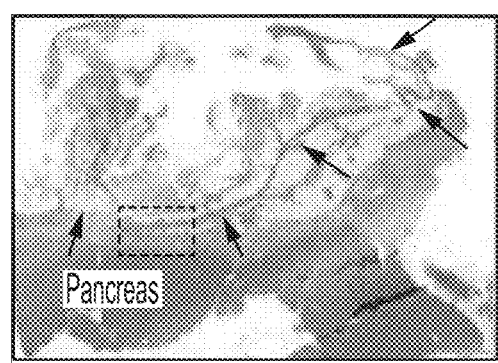
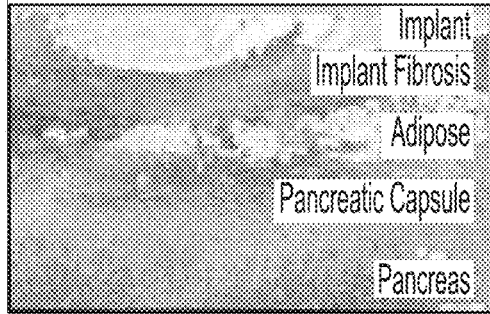
FIG. 30
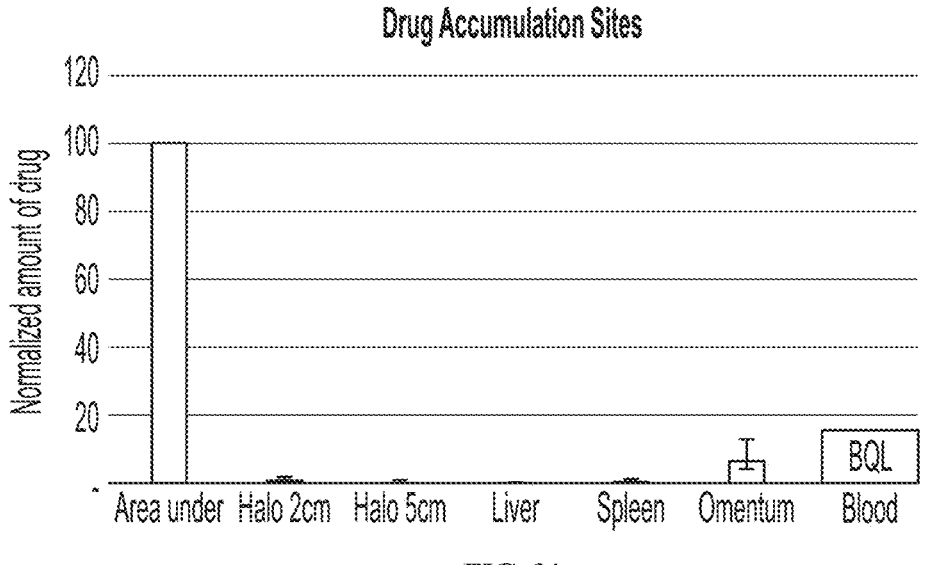
FIG. 31

| Disc | Weight (g) |
|---|---|
| 05 | 1.78009 |
| 01 | 1.90827 |
| 04 | 1.89975 |
| Positive Control | 0.10467 |

Cumulative Drug Release

| Time from Implant | T (mm) Transversal | AP (mm) Orthogonal | Volume (mm3) | ΔT (%) | ΔAP (%) | ΔV (%) |
|---|---|---|---|---|---|---|
| Baseline | 58 | 37 | 38,262 | 0% | 0% | 0% |
| Implant | | | | | | |
| 2 weeks | 56 | 27 | 33,992 | -3% | -27% | -11% |
| 9 weeks | 51 | 27 | 15,772 | -12% | -27% | -59% |
| 15 weeks | 29 | 27 | 12,307 | -50% | -27% | -68% |
| 23 weeks | 29 | 27 | 10,560 | -50% | -27% | -72% |

| Time from Implant | T (mm) Transversal | AP (mm) Orthogonal | Volume (mm3) | ΔT (%) | ΔAP (%) | ΔV (%) |
|---|---|---|---|---|---|---|
| Baseline | 64 | 49 | 49,633 | 0% | 0% | 0% |
| Implant | | | | | | |
| 3 weeks | 67 | 41 | 59,336 | 5% | -16% | 19% |
| 11 weeks | 73 | 41 | 49,522 | 14% | -16% | -0.2% |
| 17 weeks | 80 | 41 | 53,333 | 25% | -16% | 7.4% |

| Time from Implant | T (mm) Transversal | AP (mm) Orthogonal | Volume (mm3) | ΔT (%) | ΔAP (%) | ΔV (%) |
|---|---|---|---|---|---|---|
| Baseline | 30 | 24 | 13,579 | - | - | - |
| Implant | | | | | | |
| 2 weeks | 45 | 18 | 12,318 | 0% | -25% | -9.2% |
| 11 weeks | 40 | 18 | 8,853 | -11% | -25% | -34% |
| 16 weeks | 40 | 19 | 8,059 | -11% | -21% | -40% |
| 24 weeks | 40 | 20 | 8,881 | -11% | -16% | -34% |

FIG. 54

| | Baseline | Day 2 | Day 7 | Day 14 | Day 21 | Day 28 | 3 Month | 6 Month |
|---|---|---|---|---|---|---|---|---|
| Pt-001 | 39 | 35 | 30 | 26 | 28 | 42 | 33 | 39 |
| Pt-002 | 337 | 443 | 517 | 408 | 475 | 712 | 593 | 509 |
| Pt-003 | 501 | 483 | 643 | | 317 | 871 | 1622 | |

METHODS OF TREATING PANCREATIC CANCER

CROSS-REFERENCE TO RELATED APPLICATION

This application claims the benefit of U.S. Provisional Application No. 63/384,145 filed Nov. 17, 2022, the entire contents of which are incorporated herein by reference.

FIELD OF THE DISCLOSURE

This relates to implantable drug delivery devices for treating pancreatic cancer. Specifically, this relates to implantable and biodegradable drug delivery devices that deliver active pharmaceutical ingredients to local pancreatic cancer sites.

BACKGROUND OF THE DISCLOSURE

Most of the work being done in the cancer space is based on new ways to use or package existing systemic chemotherapies. In other words, most researchers are either testing chemotherapies that have been approved in other cancers, or testing new IV delivery methods such as liposomes. However, the major limit of existing chemotherapy effectiveness is due to systemic off-target toxicity. For example, only 1-5% of a chemotherapy dose via systemic administration actually reaches the tumor site. In fact, even some of the most promising currently available chemotherapies are not tolerable in the long term for most patients.

SUMMARY OF THE DISCLOSURE

Applicant has discovered an implantable and biodegradable drug delivery device capable of delivering an active pharmaceutical ingredient (API) directly to the target tissue in the patient. Since the drug delivery devices disclosed herein utilize a local delivery method, these devices can sidestep the problem of systemic side effects and can more directly provide site-specific treatment without having to perform subsequent removal surgeries due to their biodegradable nature. Specifically, the drug devices disclosed herein can be flexibly applied via open and minimally invasive surgery, allow for unidirectional, multidirectional, or omni-directional delivery of APIs via a multilayer configuration, act as a barrier to tumor ingrowth and prevent systemic drug leakage, provide tunable release profiles and degradation rates, and/or consent adaptable design translatable to solid tumors.

The drug delivery devices can be flexible such that it can be placed onto target tissue (e.g., a peritumoral area of an organ) in a patient using standard open, laparoscopic, endoscopic, percutaneous, or robotic surgical equipment. In addition, the flexible drug delivery device can pliably conform with the underlying topography of the targeted tissue site. In some embodiments, multiple drug delivery devices can be placed onto target tissue of a patient. In some embodiments, a second drug delivery device can be placed onto target tissue of a patient after the first drug delivery device has already degraded.

Specifically, the drug delivery devices disclosed herein can include at least two layers. One of the layers can include the API and a biodegradable polymer and a second layer can include another biodegradable polymer that degrades slower than the first biodegradable polymer. When the device is placed directly on tissue (i.e., when the API layer is facing the tissue), the API layer(s) can degrade thereby releasing the API towards the target tissue. In some embodiments, the non-API layer can prevent the API from being released away from the target tissue onto non-target tissue. In some embodiments, the non-API layer can prevent the drug delivery device from being released from the target tissue (i.e., the non-API layer can hold the drug delivery device in place).

In some embodiments, the second layer can degrade more slowly than the first layer such that the second layer can continue to prevent the API from being released away from the target tissue and/or retain the drug delivery device on the target tissue site. As such, the second layer may not degrade completely until the drug is completely released. Accordingly, the drug delivery device can be inserted in a patient to target specific tissue without having to perform a subsequent surgery to remove the device as it is wholly or mostly absorbed by the patient's body.

The drug delivery devices disclosed herein can provide clinically relevant delivery of an API directly to tissue (e.g., a tumor) with good tolerance and minimal systemic exposure of the API. This device can be used as a neoadjuvant therapy (and/or adjuvant therapy) for treatment of cancer that may improve complete resection rates, reduce the risk of local recurrence, and/or improve survival of patients.

In some embodiments, a method of treating pancreatic cancer includes implanting a drug delivery device in a peritumoral area of the pancreas of a patient, wherein the drug delivery device comprises: a first layer comprising API, solvent, and at least 70 wt. % of a first biodegradable polymer; and a second layer on a side of the first layer, the second layer comprising solvent and at least 85 wt. % of a second biodegradable polymer; releasing the API from the drug delivery device into the tumor of the pancreas by in vivo degradation of the first biodegradable polymer, wherein a size of the tumor is reduced after implantation of the drug delivery device.

In some embodiments, a method of stabilizing pancreatic cancer includes implanting a drug delivery device in a peritumoral area of the pancreas of a patient, wherein the drug delivery device comprises: a first layer comprising API, solvent, and at least 70 wt. % of a first biodegradable polymer; and a second layer on a side of the first layer, the second layer comprising solvent and at least 85 wt. % of a second biodegradable polymer; releasing the API from the drug delivery device into the tumor of the pancreas by in vivo degradation of the first biodegradable polymer, wherein a change in volume of the tumor, largest dimension of the tumor, and/or the anterior/posterior diameter of the tumor orthogonal to the drug delivery device is ±10% after implantation of the drug delivery device.

In some embodiments, a volume of the tumor is reduced by at least 10% after implantation of the drug delivery device. In some embodiments, the volume of the tumor is reduced by at least 40% after implantation of the drug delivery device. In some embodiments, the volume of the tumor is reduced by at least 70% after implantation of the drug delivery device. In some embodiments, a largest dimension of the tumor is reduced by 11% after implantation of the drug delivery device. In some embodiments, the largest dimension of the tumor is reduced by at least 50% after implantation of the drug delivery device. In some embodiments, an anterior/posterior diameter of the tumor orthogonal to the drug delivery device on the tumor is reduced by 15% after implantation of the drug delivery device. In some embodiments, the anterior/posterior diameter of the tumor orthogonal to the drug delivery device on the tumor is reduced by at least 25% after implantation of the drug delivery device. In some embodiments, the anterior/ posterior diameter is in the direction of API release from the drug delivery device. In some embodiments, any method includes administering systemic chemotherapy after implantation of the drug delivery device. In some embodiments, the drug delivery device improves tumor penetration of systemic chemotherapy. In some embodiments, a clinical outcome after implantation of the drug delivery device is RECIST partial response, RECIST complete response, or RECIST stable disease. In some embodiments, the patient's blood does not have any API during treatment of pancreatic cancer. In some embodiments, the tumor is pancreatic ductal adenocarcinoma. In some embodiments, the drug delivery device improves the quality of life of the patient. In some embodiments, the drug delivery device reduces pain of the patient. In some embodiments, the drug delivery device locally controls the pancreatic cancer. In some embodiments, the drug delivery device increases the progression-free survival (PFS) of the patient. In some embodiments, the drug delivery device converts unresectable tumors into resectable tumors. In some embodiments, the drug delivery device increases the resection rate of the pancreatic cancer in the patient. In some embodiments, the drug delivery device downstages the pancreatic cancer. In some embodiments, the drug delivery device increases the overall survival of the patient. In some embodiments, the drug delivery device decreases a risk of metastasis of the patient. In some embodiments, the drug delivery device prevents metastasis of the patient. In some embodiments, the volume of the tumor is reduced by at least 5% two weeks after implantation of the drug delivery device. In some embodiments, the largest dimension of the tumor is reduced by at least 3% two weeks after implantation of the drug delivery device. In some embodiments, the anterior/posterior diameter of the tumor orthogonal to the drug delivery device on the tumor is reduced by at least 5% two weeks after implantation of the drug delivery device. In some embodiments, an amount of CA 19-9 protein in blood of the patient is reduced by at least 20% two weeks after implantation of the drug delivery device. In some embodiments, any method includes administering systemic chemotherapy at least one week after implantation of the drug delivery device. In some embodiments, the change in volume of the tumor, largest dimension of the tumor, or the anterior/posterior diameter of the tumor orthogonal to the drug delivery device is ±10% after implantation of the drug delivery device. In some embodiments, the change in volume of the tumor, largest dimension of the tumor, or the anterior/posterior diameter of the tumor orthogonal to the drug delivery device is ±5% after implantation of the drug delivery device. In some embodiments, the first layer comprises 7.5-11 wt. % API. In some embodiments, the API is paclitaxel. In some embodiments, the solvent comprises acetone and the first layer comprises 3-11 wt. % acetone. In some embodiments, the second layer comprises 3-11 wt. % acetone. In some embodiments, the first biodegradable polymer comprises poly(lactic-co-glycolic acid) (PLGA) 50:50 and the second biodegradable polymer comprises PLGA 75:25. In some embodiments, the pancreatic cancer is non-immediately resectable pancreatic cancer, non-metastatic pancreatic cancer, borderline resectable pancreatic cancer, resectable pancreatic cancer, locally advanced pancreatic cancer, metastatic pancreatic cancer, or metastatic spread to the pancreas.

Additional advantages will be readily apparent to those skilled in the art from the following detailed description. The examples and descriptions herein are to be regarded as illustrative in nature and not restrictive.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

BRIEF DESCRIPTION OF THE DRAWINGS

The invention will now be described, by way of example only, with reference to the accompanying drawings.

FIG. 6A illustrates an image of film 4 disclosed herein before oven testing.

FIG. 6B illustrates an image of film 4 disclosed herein prepared for oven testing.

FIG. 6C illustrates an image of film 4 disclosed herein after 20 minutes at room temperature testing.

FIG. 7A illustrates an image of film 5 disclosed herein before oven testing.

FIG. 7B illustrates an image of film 5 disclosed herein prepared for oven testing.

FIG. 7C illustrates an image of film 5 disclosed herein after 20 minutes at 40° C. oven testing.

FIG. 9A illustrates an image of film 6 disclosed herein prepared for its second oven testing.

FIG. 9B illustrates an image of film 6 disclosed herein after 20 minutes at 42° C. for its second oven testing.

FIG. 10A illustrates an image of film 6 disclosed herein prepared for its third oven testing.

FIG. 10B illustrates an image of film 6 disclosed herein after 20 minutes at 45° C. for its third oven testing.

FIG. 15C illustrates another image of a rolled up drug delivery device for implantation in accordance with some embodiments disclosed herein.

FIG. 15D illustrates an image of a rolled up drug delivery device in a trocar for implantation in accordance with some embodiments disclosed herein.

FIG. 16A illustrates proper orientation of a drug delivery device with prolene suture (O) clockwise from fixation/cardinal suture X in accordance with some embodiments disclosed herein.

FIG. 16B illustrates improper orientation of a drug delivery device with prolene suture (O) counter clockwise from fixation/cardinal suture X in accordance with some embodiments disclosed herein.

FIG. 23C illustrates the degradation of a sample film after 5 days in a buffer solution in accordance with some embodiments disclosed herein.

FIG. 23E illustrates the degradation of a sample film after 2 weeks in a buffer solution in accordance with some embodiments disclosed herein.

FIG. 23G illustrates the degradation of a sample film after 4 weeks in a buffer solution in accordance with some embodiments disclosed herein.

FIG. 23H illustrates the degradation of a sample film after 6 weeks in a buffer solution in accordance with some embodiments disclosed herein.

FIG. 23I illustrates the degradation of a sample film after 8 weeks in a buffer solution in accordance with some embodiments disclosed herein.

FIG. 23J illustrates the degradation of a sample film after 10 weeks in a buffer solution in accordance with some embodiments disclosed herein.

FIG. 27A illustrates an image of a drug delivery device implanted on a porcine abdominal wall in accordance with some embodiments disclosed herein.

FIG. 27B illustrates an image of a drug delivery device implanted on a porcine pancreas in accordance with some embodiments disclosed herein.

FIG. 28 illustrates the weight gain from the porcine studies in accordance with some embodiments disclosed herein. Animals with implants on just the abdominal wall (left) and on both the pancreas and abdominal wall (right) gained weight over the 30 day period. A body condition of three indicates normal condition: Tube shape with slight rounding of the sides; Ribs, hips and backbone palpated with firm pressure.

FIG. 30 illustrates the histology of the pancreas from the porcine studies in accordance with some embodiments disclosed herein. Low magnification view of pancreas and implant cross section (top) and higher magnification views of boxed areas (bottom) showing a thin capsule and fibrosis.

FIG. 31 illustrates the drug accumulation in tissue after 30 days in the porcine studies showing drug primarily accumulates under the implant in accordance with some embodiments disclosed herein.

FIG. 54 illustrates tumor volumetric reduction of the three patients from a clinical trial of a drug delivery device in accordance with some embodiments disclosed herein.

In the Figures, like reference numbers correspond to like components unless otherwise stated.

DETAILED DESCRIPTION OF THE DISCLOSURE

Described herein are exemplary embodiments of biodegradable drug delivery devices that can be implanted in a patient to locally deliver a controlled therapeutically effective amount of an API. Specifically, the drug delivery devices disclosed herein can be configured to provide controlled release of a therapeutically effective amount of an API directly to a target tissue site (e.g., a pancreatic tumor) by in vivo degradation of a biodegradable polymer layer containing the API.

In some embodiments, the drug delivery device can be a film or patch having multiple biodegradable layers. In some embodiments, the drug delivery device can include at least one biodegradable layer. At least one layer can include an API which can be released in vivo by polymer biodegradation. In some embodiments, a second layer can be free of any API. This non-API layer can be on a side of an API layer and prevent any API from being released toward the non-API layer. In other words, the non-API layer can help ensure that the API from the API layer during in vivo degradation is being released away from the non-API backing layer towards the targeted tissue, not toward non-targeted tissue. In addition, this non-API layer can hold the drug delivery device in place during the degradation of the API layer. In some embodiments, the targeted tissue can be cancerous tissue/cells or peritumoral tissue/cells on an organ. For example, the targeted tissue can be cancerous or peritumoral tissue/cells on a pancreas.

Figure 1:
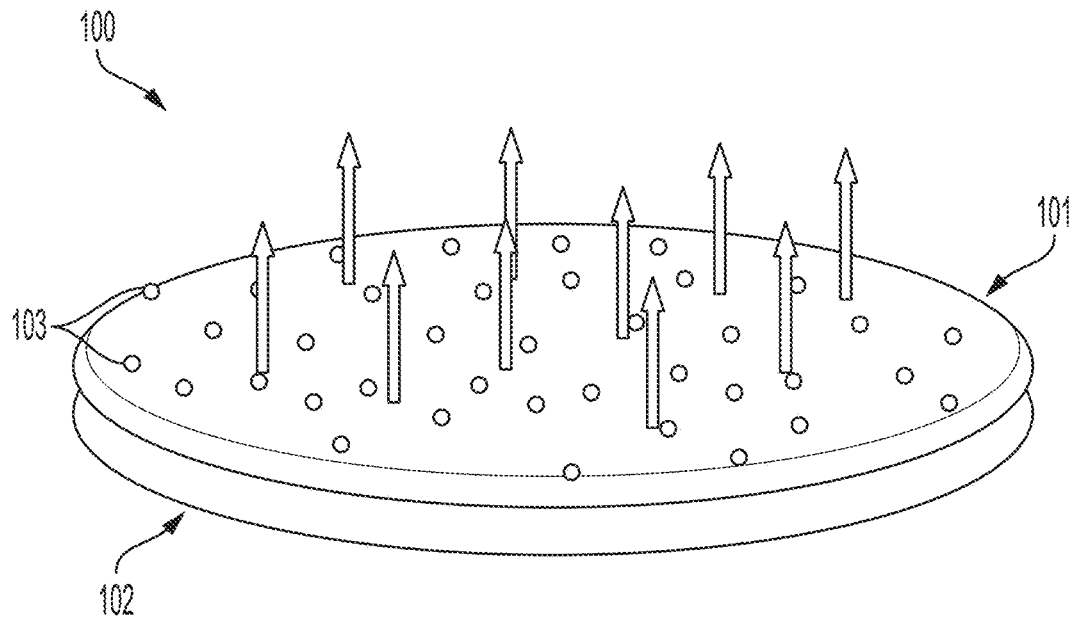
FIG. 1 illustrates a drug delivery device in accordance with some embodiments disclosed herein.

FIG. 1 illustrates drug delivery device 100 that includes API layer 101 and non-API backing layer 102. The API-containing layer can include API 103 embedded within and/or on the surface of API layer 101. In use, the API layer would face the targeted tissue such that the API is released toward the targeted tissue during degradation as shown by the arrows in FIG. 1. Non-API backing layer 102 can prevent API from being released away from the targeted tissue onto non-targeted tissue.

Although FIG. 1 illustrates the drug delivery device as a disc, the drug delivery devices disclosed herein can come in many shapes, sizes, and geometries. In some embodiments, the drug delivery device can be circular, square, rectangular, oval, triangular, diamond shaped, polygon shaped (e.g., pentagon, hexagon, octagon, etc.), arced, trapezoidal, star shaped, or a variety of other shapes and sizes. In some embodiments, the drug delivery device can be tubular, cylindrical, cone shaped, pyramidal, triangular prism shaped, cube shaped, spherical, rectangular prism shaped, or a variety of other shapes and sizes.

In some embodiments, the drug delivery devices can be made by a solvent casting method. As described in more detail below, at least one biodegradable polymer and at least one API can be dissolved in a solvent and cast in a mold. When dry, a second layer having at least one biodegradable polymer can be cast on top of the first layer and then dried to form the device. This process can be repeated for as many additional API and/or non-API layers as necessary. In some embodiments, the drug delivery device can be made via a continuous process. In some embodiments, the drug delivery devices disclosed herein can be made by continuous processes such as those employed by the polymer film production industry (e.g., extrusion, continuous film evaporation, etc.).

API Layer

In some embodiments, a drug delivery device can include at least one API containing layer. In some embodiments, an API layer can include at least one active pharmaceutical ingredient (API) and at least one biodegradable polymer. In some embodiments, an API layer can include more than one API. As explained above, an API layer can be configured to provide controlled release of the API by in vivo degradation of the biodegradable polymer at the target tissue site. In some embodiments, an API layer can also include one or more pharmaceutically acceptable excipients.

In some embodiments, the biodegradable polymer can be any suitable biodegradable polymer known in the art. For example, the biodegradable polymers can include synthetic polymers selected from poly(amides), poly(esters), poly(anhydrides), poly(orthoesters), polyphosphazenes, pseudo poly(amino acids), poly(glycerol-sebacate), copolymers thereof, and mixtures thereof. In addition, the biodegradable polymers may be formed from poly(lactic acids), poly(glycolic acids), poly(lactic-co-glycolic acids), poly(caprolactones), and mixtures thereof. In some embodiments, the biodegradable polymer can be poly(lactic-co-glycolic acid) (PLGA). In some embodiments, the PLGA can be PLGA with various lactic acid to glycolic acid ratios such as PLGA 50:50, PLGA 60:40, PLGA 65:35, PLGA 70:30, PLGA 75:25, PLGA 80:20, PLGA 85:15, PLGA 90:10, or other various ratios of PLGA. In some embodiments, the biodegradable polymer in an API containing layer includes PLGA 50:50.

PLGA can undergo degradation by hydrolysis or biodegradation through cleavage of its backbone ester linkages into oligomers followed by monomers. The lactide-glycolide ratio dictates the degradation rate of the PLGA in aqueous media (e.g., water and water containing environments such as inside a human or animal's anatomy). In general, the higher lactic acid content or lactide content, the lower the degradation behavior of the PLGA as lactide has hydrophobic properties which can prevent water from hydrolyzing the ester bonds in PLGA. As such, PLGA 50:50 degrades faster in water-containing environments than PLGA 65:35, which degrades faster than PLGA 75:25.

In some embodiments, an API containing layer includes at least about 50 wt. %, at least about 60 wt. %, at least about 70 wt. %, at least about 73 wt. %, at least about 75 wt. %, at least about 80 wt. %, at least about 85 wt. %, or at least about 90 wt. % biodegradable polymer. In some embodiments, an API containing layer includes at most about 95 wt. %, at most about 90 wt %, at most about 85 wt. %, at most about 80 wt. %, at most about 77 wt. %, or at most about 75 wt. % biodegradable polymer. In some embodiments, an API containing layer includes about 60-95 wt. %, about 70-95 wt. %, about 75-90 wt. %, about 75-89 wt. %, or about 79-89 wt. % biodegradable polymer.

In some embodiments, the API may be an active pharmaceutical ingredient for the treatment of human or veterinary diseases. In some embodiments, the API can be a chemotherapeutic agent such as any drug formulation effective to treat cancer by inhibiting the growth, invasiveness of malignant cells, and/or inducing cytotoxicity by apoptosis or necrosis of malignant cells. The chemotherapeutic agent can be a taxane or platinum drug. In some embodiments, the chemotherapeutic agent includes an MEK inhibitor, a KRAS inhibitor, a PI3K inhibitor, a Hedgehog inhibitor, a Wnt inhibitor, or a combination thereof. In some embodiments, the chemotherapeutic agent can interfere with the mTOR or NfKb pathways. In some embodiments, the chemotherapeutic agent includes STING agonist compounds. In some embodiments, the chemotherapeutic agent can interfere with the STING pathway. In some embodiments, the chemotherapeutic agent includes genetic material such as mRNA, siRNA, etc. In some embodiments, the chemotherapeutic agent can be siRNA-Alnylam type therapies. In some embodiments, the API can include a vaccinal antigen. In some embodiments, the API can be an mRNA vaccinal antigen such as an mRNA cancer vaccinal antigen.

The API may be a single active pharmaceutical ingredient, such as a single chemical entity, or it may be a mixture of several active pharmaceutical ingredients. The active pharmaceutical ingredient may be of any of the many categories of active pharmaceutical ingredients. The active pharmaceutical ingredient may be selected from, but is not limited to, the group consisting of paclitaxel, gemcitabine, nab-paclitaxel, 5-fluorouracil, oxaliplatin, irinotecan, docetaxel, vinorelbine, etoposide, mitomycin-C, cisplatin/carboplatin, fluorouracil, methotrexate, TAS-102, or combinations thereof. In some embodiments, the API is paclitaxel. In some embodiments, the paclitaxel is from Phyton Biotech.

In some embodiments, the API can be an API for targeted therapy such as bevacizumab, ramucirumab, erlotinib, afatinib, gefitinib, osimertinib, dacomitinib, crizotinib, ceritinib, alectinib, brigatinib, lorlatinib, dabrafenib, trametinib, sunitinib, regorafenib, or combinations thereof. In some embodiments, the API can be an API for immunotherapies such as nivolumab, pembrolizumab, atezolizumab, durvalumab, ipilimumab, or combinations thereof.

APIs may include salts, esters, hydrates, solvates and derivatives of any of the foregoing active ingredients. Suitable derivatives are those that are known to skilled persons to possess the same activity as the active ingredient though the activity level may be lower or higher. In some embodiments, the API can be in the form of microspheres. In some embodiments, the microspheres can release the API. In some embodiments, the API is encapsulated within microspheres.

When present, an API is employed in the formulation in a therapeutically effective amount that is necessary to provide the dosage required, typically for producing at least one physiological effect as established by clinical studies. One of ordinary skill in the art can readily determine an appropriate amount of an active pharmaceutical ingredient to include in the drug delivery device made according to the present disclosure.

In some embodiments, an API containing layer includes at least about 1 wt. %, at least about 2 wt. %, at least about 3 wt. %, at least about 5 wt. %, at least about 7 wt. %, at least about 8 wt. %, at least about 9 wt. %, at least about 10 wt. %, at least about 11 wt. %, or at least about 15 wt. % API. In some embodiments, an API containing layer includes at most about 30 wt. %, at most about 20 wt. %, at most about 15 wt. %, at most about 12 wt. %, at most about 11 wt. %, at most about 10 wt. %, at most about 9 wt. %, at most about 8 wt. %, at most about 7 wt. %, or at most about 5 wt. % API. In some embodiments, an API containing layer includes about 1-15 wt. %, about 5-15 wt. %, about 7-12 wt. %, about 8-12 wt. %, or about 7.5-11 wt. % API. In some embodiments, an API containing layer can include about 1-500 mg, about 25-450 mg, about 30-400 mg, about 40-350 mg, about 50-300 mg, about 60-250 mg, about 70-200 mg, about 80-150 mg, about 85-125 mg, about 90-105 mg, about 95-105 mg, or about 100 mg API.

To prepare an API layer in some embodiments of the drug delivery devices disclosed herein, a solution of a biodegradable polymer and an API can be formed. Specifically, an amount of biodegradable polymer can be dissolved in a solvent. The biodegradable polymer/solvent solution can be stirred and/or heated to help dissolve the polymer in the solvent. In some embodiments, the solvent can be acetone, chloroform, tetrahydrofuran, ethyl acetate, methyl acetate, xylene, toluene, methyl ethyl ketone, methylene chloride, isopropyl alcohol, methyl isobutyl ketone, methyl propyl ketone, trichloroethylene, other substitutes for acetone, or combinations thereof. In some embodiments, the biodegradable polymer and solvent solution can be about 0.1-0.3 g biodegradable polymer, about 0.15-0.25 g biodegradable polymer, about 0.175-0.225 g biodegradable polymer, about 0.19-0.21 g biodegradable polymer, about 0.198-0.202 g biodegradable polymer, or about 0.2 g biodegradable polymer per 1 mL solvent. In other words, 20 g biodegradable polymer in 100 mL of solvent would be a biodegradable polymer and solvent solution of 0.2 g biodegradable polymer per 1 mL solvent. The above concentrations can also be true for the biodegradable polymer/API solution discussed below. For example, the biodegradable polymer/API solution can have about 0.1-0.3 g biodegradable polymer, about 0.15-0.25 g biodegradable polymer, about 0.175-0.225 g biodegradable polymer, about 0.19-0.21 g biodegradable polymer, about 0.198-0.202 g biodegradable polymer, or about 0.2 g biodegradable polymer per 1 mL solvent.

After the biodegradable polymer is dissolved in the solvent, the API can be added to the solution. In some embodiments, the API and biodegradable polymer can be added simultaneously to the solvent. In some embodiments, the API can be added to the solvent prior to the addition of the biodegradable polymer. In some embodiments, the API can be added to a solvent to form a first solution, the biodegradable polymer can be added to a solvent to form a second solution, and the first and second solutions can be combined to form the biodegradable polymer/API solution. In some embodiments, the API can be in the form of microspheres when incorporating the API to a biodegradable polymer layer. In some embodiments, the microspheres can help prevent the API from dissolving and/or deteriorating in the polymer/solvent solution.

In some embodiments, the biodegradable polymer/API solution can have about 0.01-0.05 g API, about 0.01-0.04 g API, about 0.015-0.035 g API, about 0.02-0.03 g API, about 0.023-0.027 g API, or about 0.025 g API per 1 mL solvent. The above concentrations are also true for an API and solvent solution (without the biodegradable polymer). The biodegradable polymer/API solution can be stirred and/or heated until the API is well mixed and/or dissolved in the solvent.

After the biodegradable polymer/API solution is formed, the solution can be added to a mold. The mold can be any container used to give shape to the API layer when it is formed. As such, the mold can be circular, square, rectangular, oval, triangular, diamond shaped, polygon shaped (e.g., pentagon, hexagon, octagon, etc.), arced, trapezoidal, star shaped, or a variety of other shapes and sizes. Besides shape, the mold can also dictate the size (i.e., width, length, diameter, etc.) of the layer.

Accordingly, if the drug delivery device is to be circular in shape, the biodegradable polymer/API solution can be added to a circular mold. In some embodiments, the mold can be an evaporation dish, a petri dish, or the like. In addition, the amount added to the mold can depend on the desired thickness and/or API concentration of the API layer. In addition, the amount added to the mold can depend on the desired API release rate of the API layer. In some embodiments, about 1-20 mL, about 1-10 mL, about 4-6 mL, or about 5 mL of the biodegradable polymer/API solution can be added to the mold.

Once in the mold, biodegradable polymer/API solution can be dried. This drying can cause solvent to evaporate, thereby leaving a solidified layer that includes biodegradable polymer, API, and some remaining solvent. Remaining solvent in the layer can be important because it allows the layer(s) to retain flexibility and not crack during subsequent folding/rolling. As such, an API layer can also include a small amount of solvent, which will be discussed in further detail below. In some embodiments, the biodegradable polymer/API solution can be dried in air, nitrogen, or other gases at room temperature (e.g., 20-25° C.) in the mold. In some embodiments, the biodegradable polymer/API solution can be dried in an environment with a humidity of less than about 30%, less than about 25%, less than about 20%, less than about 15%, less than about 10%, less than about 5%, or less than 1%. In some embodiments, the drying can be for about 1-6 days, about 1-4 days, about 1-3 days, or about 1.5-2.5 days.

Non-API Layer

In some embodiments, a drug delivery device can include at least one non-API containing layer. In some embodiments, a non-API layer can be free from an API. In some embodiments, the non-API layer can include at least one biodegradable polymer. As explained above, in some embodiments, a non-API layer can act as a backing layer to an API layer and can help prevent the API from being released away from the target tissue site onto non-targeted tissue. In some embodiments, the non-API layer can include a biodegradable polymer with a slower degradation rate than the biodegradable polymer in an API layer. As explained below, PLGA 50:50 can be the biodegradable polymer in the API layer and PLGA 75:25 can be the biodegradable polymer in the second layer as PLGA 75:25 degrades slower than the PLGA 50:50. In some embodiments, the non-API layer can include a biodegradable polymer with the same or faster degradation rate than the biodegradable polymer in an API layer. In some embodiments, a non-API layer can also include one or more pharmaceutically acceptable excipients.

For example, the biodegradable polymer in the API layer can degrade over the course of about 4 weeks releasing the API towards the targeted tissue. The biodegradable polymer in the non-API layer can degrade in a longer period of time (e.g., 10 weeks). Thus, in some embodiments, the non-API backing layer can be used to hold the drug delivery device in its targeted location (e.g., on a tumor) while the API layer degrades to release the API. After the API layer completely degrades and the API has been completely released to the targeted tissue, the non-API layer can completely degrade to be absorbed by the body of the patient. In some embodiments, a portion of the non-API layer can degrade while the API layer is degrading, but the degradation rate of the non-API layer can be slower than the API layer's degradation rate such that the non-API layer can prevent any API from being released away from the target tissue site and/or hold the drug delivery device into place at the target tissue site. Thus, in some embodiments, the non-API layer allows for unidirectional delivery of the API towards the target tissue site.

In some embodiments, the biodegradable polymer can be any suitable biodegradable polymer known in the art. As explained above, a biodegradable polymer in a non-API layer has a slower degradation rate than a biodegradable polymer in the API layer. For example, the biodegradable polymers can include synthetic polymers selected from poly(amides), poly(esters), poly(anhydrides), poly(orthoe-sters), polyphosphazenes, pseudo poly(amino acids), poly(glycerol-sebacate), copolymers thereof, and mixtures thereof. In addition, the biodegradable polymers may be formed from poly(lactic acids), poly(glycolic acids), poly(lactic-co-glycolic acids), poly(caprolactones), and mixtures thereof. In some embodiments, the biodegradable polymer can be poly(lactic-co-glycolic acid) (PLGA). In some embodiments, the PLGA can be PLGA with various lactic acid to glycolic acid ratios such as PLGA 50:50, PLGA 60:40, PLGA 65:35, PLGA 70:30, PLGA 75:25, PLGA 80:20, PLGA 85:15, PLGA 90:10, or other various ratios of PLGA. In some embodiments, the biodegradable polymer in a non-API containing layer includes PLGA 75:25.

In some embodiments, a non-API containing layer includes at least about 70 wt. %, at least about 75 wt. %, at least about 80 wt. %, at least about 85 wt. %, at least about 90 wt. %, or at least about 95 wt. % biodegradable polymer. In some embodiments, a non-API containing layer includes at most about 99.9 wt. %, at most about 99 wt. %, at most about 98 wt %, at most about 97 wt. %, at most about 95 wt. %, or at most about 90 wt. % biodegradable polymer. In some embodiments, a non-API containing layer includes about 80-99.9 wt. %, about 85-98 wt. %, about 86-97 wt. %, or about 88-96 wt. % biodegradable polymer.

To prepare a non-API layer for the drug delivery device, a second solution of a biodegradable polymer can be formed. Specifically, an amount of biodegradable polymer can be dissolved in a solvent. The second biodegradable polymer/solvent solution can be stirred and/or heated to help dissolve the polymer in the solvent. In some embodiments, the solvent can be acetone, chloroform, tetrahydrofuran, ethyl acetate, methyl acetate, xylene, toluene, methyl ethyl ketone, methylene chloride, isopropyl alcohol, methyl isobutyl ketone, methyl propyl ketone, trichloroethylene, other substitutes for acetone, or combinations thereof. In some embodiments, the biodegradable polymer and solvent solution can be about 0.1-0.3 g biodegradable polymer, about 0.15-0.25 g biodegradable polymer, about 0.175-0.225 g biodegradable polymer, about 0.19-0.21 g biodegradable polymer, about 0.198-0.202 g biodegradable polymer, or about 0.2 g biodegradable polymer per 1 mL solvent. In other words, 20 g biodegradable polymer in 100 mL of solvent would be a biodegradable polymer and solvent solution of 0.2 g biodegradable polymer per 1 mL solvent.

In some embodiments, after the second biodegradable polymer solution is formed, the solution can be added to the mold containing the API layer. As such, the second biodegradable polymer solution can be added over the API layer in the mold such as a covering or coating over the API layer. The amount added to the mold can depend on the desired thickness (and degradation rate) of the non-API layer. In some embodiments, about 1-20 mL, about 1-10 mL, about 4-6 mL, or about 5 mL of the biodegradable polymer second solution can be added to the mold with the API layer. In some embodiments, the non-API biodegradable solution can be added to the mold first to form the non-API layer (in a similar manner to the API layer as explained above with respect to the API layer) and then an API layer can be formed on top of the non-API layer in the mold.

Once in the mold, second biodegradable polymer solution can be dried. In some embodiments, this drying can cause solvent to evaporate, thereby leaving a second solidified layer on a side of the first solidified API layer. The second layer can be adhered to the first layer via a solvent welding process. In other words, the second layer can adhere to the first layer because the first layer may dissolve slightly when the second layer is applied and can redry with the second layer to form a solid second layer on a side of the solid first layer. This second layer can include biodegradable polymer (having a slower degradation rate than the biodegradable polymer of the first API layer) and some remaining solvent. As such, a non-API layer can also include a small amount of solvent, which will be discussed in further detail below. In some embodiments, the non-API biodegradable polymer solution can be dried in air, nitrogen, or other gases at room temperature (e.g., 20-25° C.) in the mold. In some embodiments, the non-API biodegradable polymer solution can be dried in an environment with a humidity of less than about 30%, less than about 25%, less than about 20%, less than about 15%, less than about 10%, less than 5%, or less than about 1%. In some embodiments, the drying can be for about 1-6 days, about 1-4 days, about 1-3 days, or about 1.5-2.5 days. The layers of the drug delivery device can have uniform consistency and be homogeneous.

The above process of preparing an API layer and a non-API layer adhered to the API layer can be repeated for additional layers as well as other API layers and non-API layers adhered to a side of the API layer, other API layers, the non-API layer, and/or other non-API layers. In other words, the drug delivery devices disclosed herein can include any number of API layers and non-API layers in any order such as API/non-API, non-API/API, API/non-API/API, non-API/API/non-API, API/API/non-API, non-API/API/API, API/non-API/API/non-API, API/API/non-API/non-API, API/API/API/non-API, non-API/API/non-API/API, non-API/API/API/non-API configurations and so on. These additional API layers and/or non-API layers can have a composition of any API layer or non-API layer disclosed herein and be made by the same process as any API layer or non-API layer disclosed herein.

In some embodiments, the drug delivery device can include more than one API layer. In some embodiments, the drug delivery device can include a non-API layer sandwiched between two API layers. In some embodiments, the drug delivery device can include two API layers on top of one another and then a non-API layer on a side of one of the API layers. For example, in some embodiments, the drug delivery device can include a second API layer on a side of the first API layer and a non-API layer on a side of the second API layer opposite the first API layer. In some embodiments, the second API layer can have the same composition (i.e., API) as the first API layer. In some embodiments, there may be more than two API layers before a non-API layer. These API layers can have the same or different composition or the same or different API. Furthermore, these additional layers can be added to the drug delivery device by the same methods disclosed herein.

In some embodiments, the drug delivery device can include more than one non-API layer. In some embodiments, the drug delivery device can include an API layer sandwiched between two non-API layers. For example, in some embodiments, the drug delivery device can include a first non-API layer on a side of the API layer and a second non-API layer on a side of the API layer opposite the first non-API layer. In some embodiments, the second non-API layer can have the same composition as the first non-API layer. In some embodiments, the second non-API layer can have a different composition as the first non-API layer. In some embodiments, the second non-API layer can degrade faster, slower, or the same as the API layer. In some embodiments, the first non-API layer can degrade faster, slower, or the same as the API layer. In some embodiments, first non-API layer can degrade faster, slower, or the same as the second non-API layer. In some embodiments, there may be more than two non-API layers before a API layer. Furthermore, these additional layers can be added to the drug delivery device by the same methods disclosed herein.

In some embodiments, the drug delivery device can include a second API layer on a side of the first API layer configured to degrade at a slower rate than the first API layer, and a non-API layer configured to degrade at a slower rate than the second API layer on side of the second API layer opposite the first API layer. In other words, a first solution of a first biodegradable polymer and a first API can be added to a mold and dried to form a first layer. Next, a second solution of a second biodegradable polymer (having a degradation rate slower than the first biodegradable polymer) and a second API can be added over the first layer in the mold and dried to form a second layer. Next, a third solution of a third biodegradable polymer (having a degradation rate slower than the second biodegradable polymer) can be added over the second layer in the mold and dried to form a third non-API layer. For example, the drug delivery device can include a first layer with an API and PLGA 50:50, a second layer with the same or different API and PLGA 65:35, and a non-API layer containing PLGA 75:25. The first PLGA 50:50 layer would degrade first releasing the first API, then the second PLGA 65:35 layer would degrade releasing the second API, and finally the non-API PLGA 75:25 layer would degrade.

Figure 2:
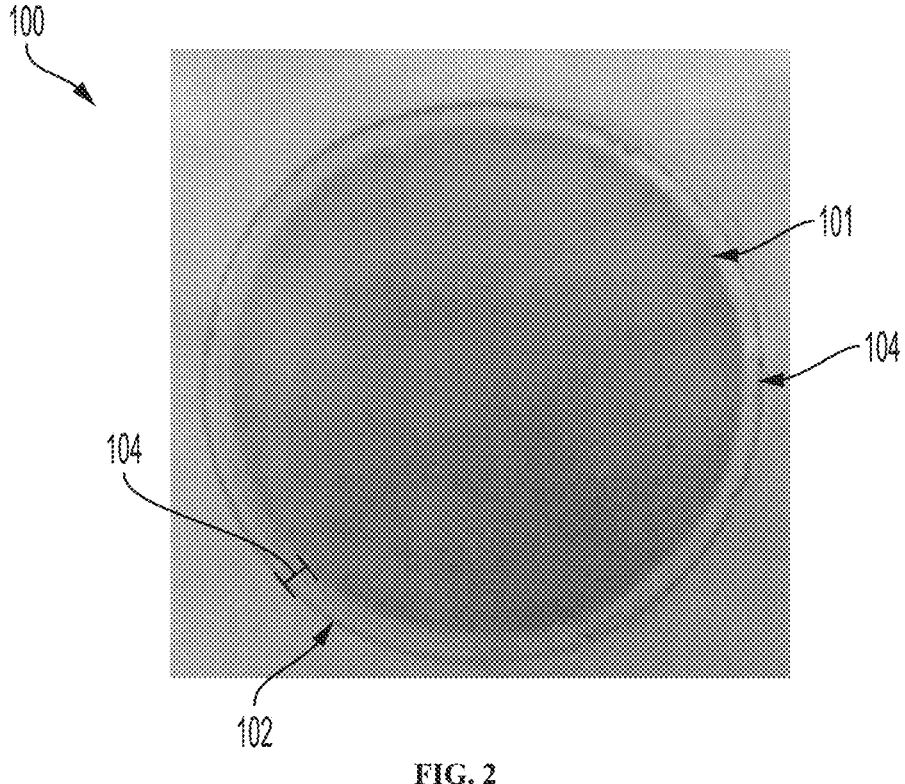
FIG. 2 illustrates an image of a drug delivery device showing the portion of the non-API layer that extends beyond the API layer in accordance with some embodiments disclosed herein.

After the desired amount of API and non-API layers have been added and dried in the mold, the drug delivery film can be removed from the mold. In some embodiments, an outer perimeter of the first layer (e.g., an API layer) can be inset relative to an outer perimeter of a second layer (e.g., non-API layer) formed on top of the first layer such that a portion of the second layer extends beyond the first layer. This is shown in FIG. 2 which illustrates an image of a drug delivery device having an API layer 101 and non-API layer 102, wherein a portion of the non-API layer extends beyond the first layer acting as a border, rim, or edge 104 around the API layer.

There are many ways to form this border around the API layer. In some embodiments, because the composition (and viscosity) of the non-API layer is different from the API layer, the non-API layer can adhere and climb the edges or sides of the mold (e.g., evaporation dish) when added to the mold. Thus, during drying, a portion of the non-API layer can form on the edges or sides of the mold and not directly on the API layer. This portion that forms on the edges or sides of the mold can be the border, rim, or edge shown around the API layer.

Oven Drying

Because the drug delivery devices disclosed herein can be placed directly onto target tissue areas using minimally invasive standard surgical techniques such as open, laparoscopic, endoscopic, percutaneous, or robotic surgery, the drug delivery device should be flexible enough to be used with standard surgical equipment (e.g., a trocar used in laparoscopic surgery, a catheter in endoscopic surgery, a bronchoscope, robotic bronchoscope, etc.). In some embodiments, the drug delivery devices can be rolled and/or folded to be inserted through a 3 mm to 12 mm (e.g., 3, 5, 8, 10, 12 mm trocar) and larger trocar. Thus, once inside the patient, the drug delivery device can be unfolded to be placed onto the target tissue site (e.g., tumor) using standard surgical equipment. In some embodiments, the drug delivery device is placed on the target tissue such that it covers the targeted tissue and is adhered to tissue adjacent to the targeted tissue. For example, if the targeted tissue is a tumor of an organ, the drug delivery device can be placed on the organ to cover the tumor area with the API layer (i.e., the API layer is in contact with the tumor or peritumoral area) of the drug delivery device and the device can be adhered to non-tumor portions of the organ.

In initial studies, Applicant discovered that when some drug delivery devices were inserted inside a patient, the high internal temperature caused the device to adhere to itself or melt or flow such that it could not be properly unfolded to be placed on the target tissue site. Applicant discovered that at least part of the cause of this was that there was too much solvent left in the drug delivery device. Solvent can be important because it allows the layer(s) (and overall device) to retain flexibility and not crack during subsequent folding/rolling. However, too much solvent can cause the layer(s) to stick/adhere to themselves at warm temperatures. Accordingly, Applicant discovered a way to remove more solvent as well as a more optimal amount of solvent in the drug delivery device for it to be properly implantable in a patient (i.e., maintain proper flexibility/pliability for surgery, but not adhere/stick to itself).

Figures 3A, 3B, 3C:
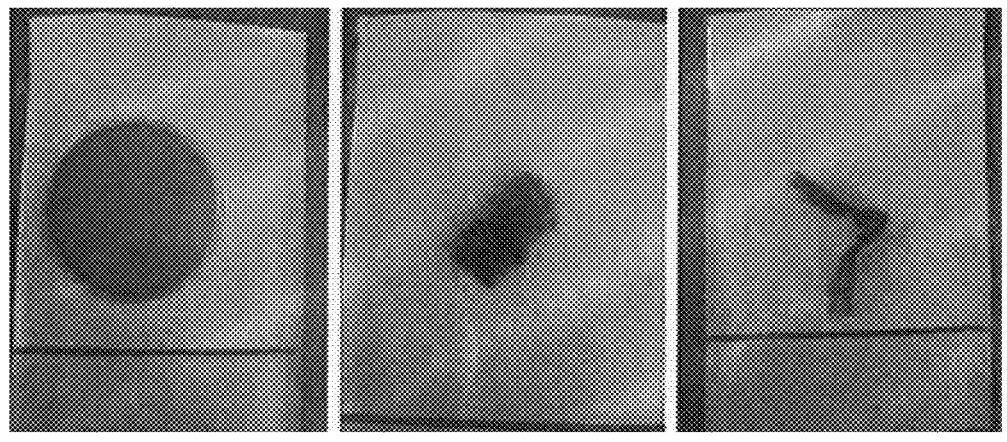
FIG. 3A illustrates an image of film 1 disclosed herein before oven testing.
FIG. 3B illustrates an image of film 1 disclosed herein prepared for oven testing.
FIG. 3C illustrates an image of film 1 disclosed herein after 20 minutes in a 45° C. oven testing.
Figures 4A, 4B, 4C:
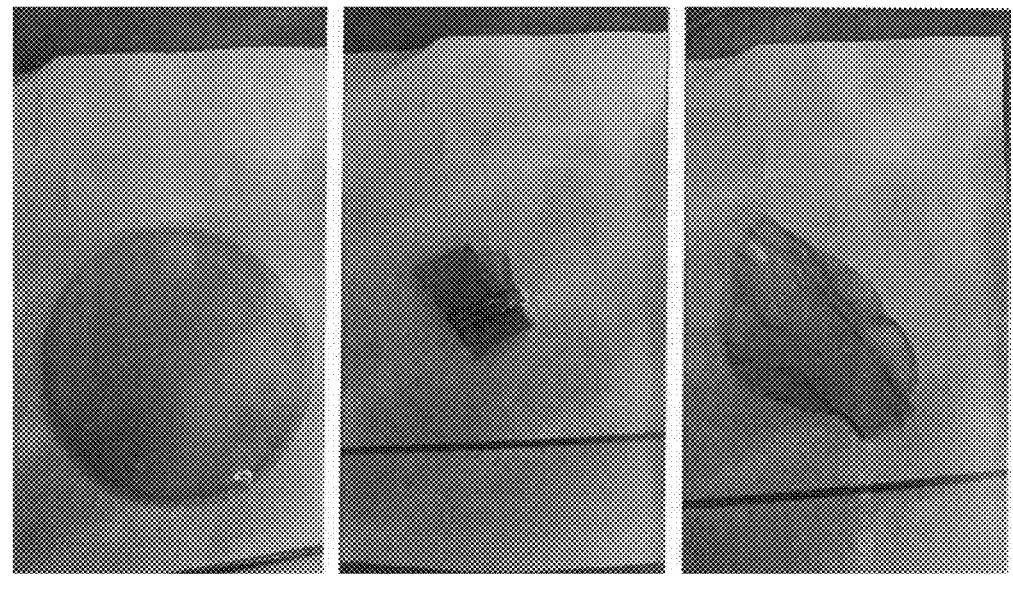
FIG. 4A illustrates an image of film 2 disclosed herein before oven testing.
FIG. 4B illustrates an image of film 2 disclosed herein prepared for oven testing.
FIG. 4C illustrates an image of film 2 disclosed herein after 20 minutes at 42° C. oven testing.
Figures 5A, 5B, 5C:
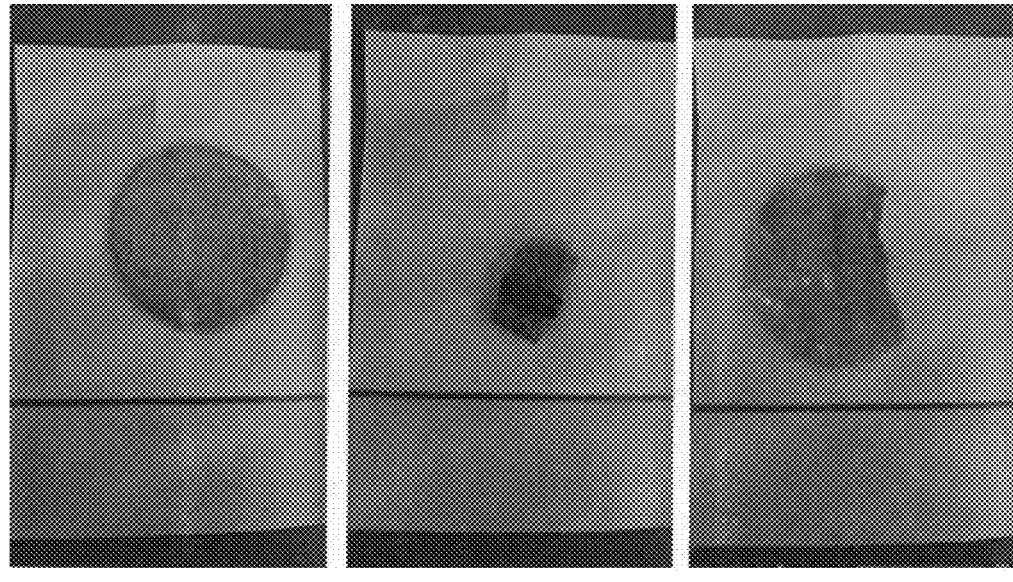
FIG. 5A illustrates an image of film 3 disclosed herein before oven testing.
FIG. 5B illustrates an image of film 3 disclosed herein prepared for oven testing.
FIG. 5C illustrates an image of film 3 disclosed herein after 20 minutes in a 37° C. oven testing.
Figures 8A, 8B, 8C:
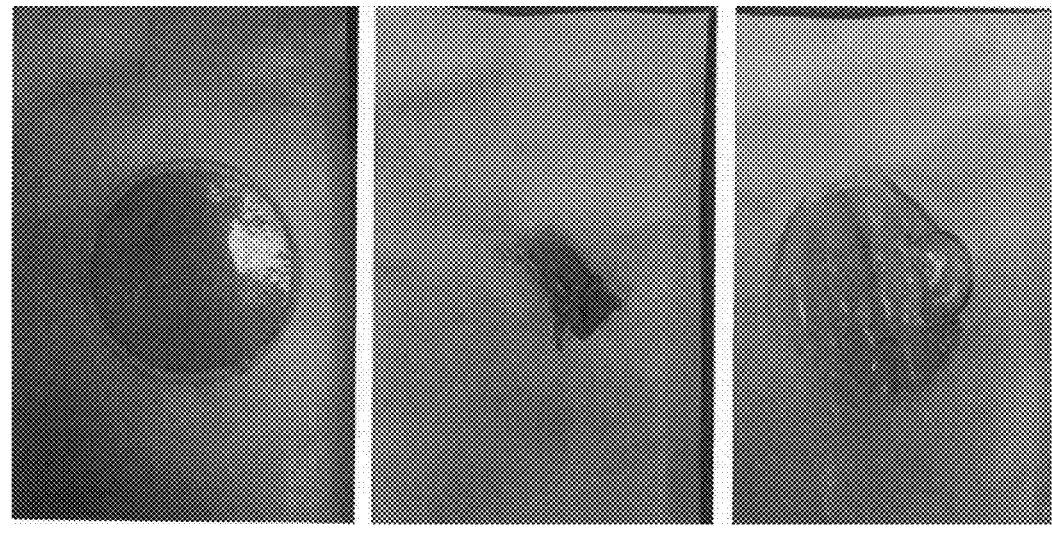
FIG. 8A illustrates an image of film 6 disclosed herein before oven testing.
FIG. 8B illustrates an image of film 6 disclosed herein prepared for oven testing.
FIG. 8C illustrates an image of film 6 disclosed herein after 20 minutes at 40° C. oven testing.

Specifically, six films containing a first layer of 0.8-1 g of PLGA 50:50 (and acetone) and a second layer on a side of the first layer made up of 0.8-1 g PLGA 75:25 (and acetone) were tested in an oven to determine whether manufacturing changes effected the tendency of the films to adhere to themselves. Film 1 was rolled up and folded once, and the shape was held in place using a rubber band while placed in an oven (HeraTherm high temp oven) for 20 minutes at 45° C. After 20 minutes, film 1 was completely adhered and could not be unrolled by any means as shown in FIGS. 3A-3C. Film 2 was rolled and folded in the same fashion as film 1 and placed in the oven for 20 minutes at 42° C. After 20 minutes, Film 2 could still be unfolded, but was partially stuck at areas that were most tightly wrapped as shown in FIGS. 4A-4C. Films 3, 4, and 5 were tested to confirm that the test results were consistent with results obtained during method development. Film 3 was folded the same way as previous tests, and placed in the oven at 37° C. for 20 minutes, film 4 was similarly folded but held at room temperature for 20 minutes, and film 5 was similarly folded and placed in the oven at 40° C. for 20 minutes. Film 3 could not be fully opened after 20 minutes at 37° C. because some areas did adhere as shown in FIGS. 5A-5C. This occurred at a lower temperature than was seen in previous batches. Film 4 showed no signs of sticking as shown in FIGS. 6A-6C. Film 5 was fully adhered and could not be opened at all as shown in FIGS. 7A-7C.

Film 6 was dried in a Binder Convection oven at 40° C. for 3 days following initial manufacture. Film 6 felt stiffer at room temperature after removal from the oven suggesting that there may have been additional solvent removal. Film 6 was rolled and folded and placed in an oven at 40° C. for 20 minutes. After removal, because it did not stick, film 6 was retested at 42° C. for 20 minutes and finally 45° C. for 20 minutes. Film 6 did not adhere to itself at all during any of the tests as shown in FIGS. 8A-8C, 9A-9B, and 10A-10B. As such, films that were not dried may not perform appropriately at temperatures that could be experienced when the drug delivery device is implanted in human/animal trials. However, Applicant discovered that the addition of an oven drying step could remove enough excess solvent such that the drug delivery device may not have performance issues even at 45° C., a temperature outside the range that would be expected clinically.

Accordingly, after removal of the drug delivery device from the mold (or in some embodiments while still in the mold), the drug delivery device can be placed in an oven for additional drying. In some embodiments, the drug delivery device is placed in an oven at at least about 30° C., at least about 35° C., at least about 36° C., at least about 37° C., at least about 38° C., at least about 39° C., at least about 40° C., or at least about 42° C. In some embodiments, the drug delivery device is placed in an oven at at most about 50° C., at most about 45° C., at most about 42° C., at most about 40° C., at most about 39° C., at most about 38° C., at most about 37° C., or at most about 36° C. In some embodiments, the drug delivery device is placed in an oven at 30-45° C., 32-45° C., 35-45° C., 35-42° C., 35-41° C., 36-40° C., 37-39° C., or 38° C. In some embodiments, the drug delivery device is placed in an oven for about 1-5 days, about 2-4 days, about 2.5-3.5 days, about 2.75-3.25 days, about 68-80 hours, or about 3 days.

Thus, the drug delivery device can have a solvent content of less than about 12 wt. % or about 1-15 wt. %, about 2-12 wt %, or about 3-11 wt. %. In some embodiments, an API-layer of the drug delivery device can have at least about 1 wt. %, at least about 2 wt. %, at least about 3 wt. %, at least about 3.5 wt. %, at least about 5 wt. %, at least about 7 wt. %, or at least about 10 wt. % solvent. In some embodiments, an API layer of the drug delivery device can have at most about 15 wt. %, at most about 12 wt. %, at most about 10 wt. %, or at most about 5 wt. % solvent. In some embodiments, an API layer of the drug delivery device can have about 1-15 wt. %, about 2-12 wt %, about 3-11 wt. %, or about 3.5-10 wt. % solvent. In some embodiments, a non-API layer of the drug delivery device can have at least about 1 wt. %, at least about 2 wt. %, at least about 3 wt. %, at least about 3.5 wt. %, at least about 5 wt. %, at least about 7 wt. %, or at least about 10 wt. % solvent. In some embodiments, a non-API layer of the drug delivery device can have at most about 15 wt. %, at most about 12 wt. %, at most about 11 wt. %, at most about 10 wt. %, or at most about 5 wt. % solvent. In some embodiments, a non-API layer of the drug delivery device can have about 1-15 wt. %, about 2-12 wt %, about 3-11 wt. %, or about 3.5-11 wt. % solvent. The amount of solvent in the drug delivery device can be measured by gas chromatography.

In some embodiments, the drug delivery device can be sterilized such as by e-beam radiation. In addition, the drug delivery device can be sealed in a pouch such as a Tyvek pouch to be sterilized and stored in a fridge.

Orientation Indicator and Suturing

Figure 11A:
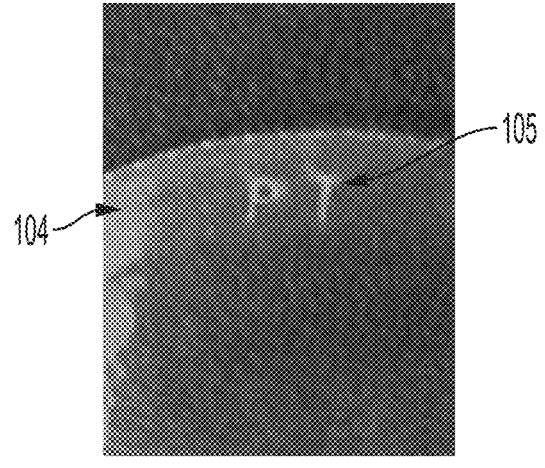
FIG. 11A illustrates an image of a drug delivery device showing the orientation identifier in accordance with some embodiments disclosed herein.
Figure 11B:
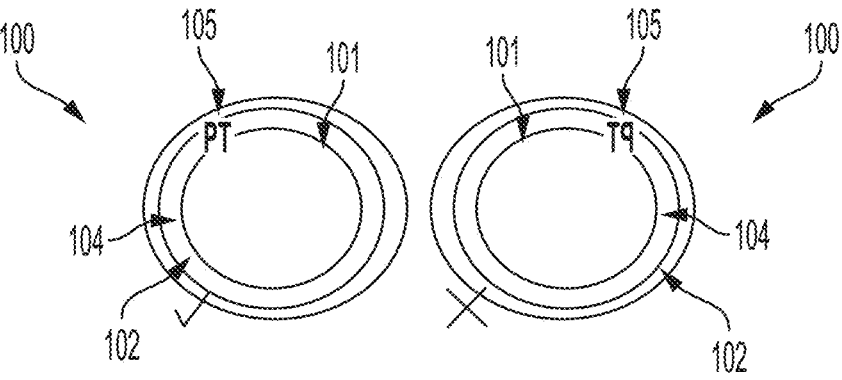
FIG. 11B a drug delivery device properly (left with check mark) and improperly (right with X) oriented in accordance with some embodiments disclosed herein.

As explained above, an outer perimeter of an API layer can be inset relative to an outer perimeter of a non-API layer such that a portion of a non-API layer extends beyond the first layer as shown in FIG. 2. Because the biodegradable polymers utilized in the layers can have similar colors and/or similar transparency, it can be difficult for someone to identify which side of the drug delivery device has the API layer and the non-API layer. As such, in some embodiments, a non-API layer can be marked with an orientation identifier. In some embodiments, the portion (i.e., the rim) of the non-API layer that extends beyond the API layer can include the orientation identifier. In some embodiments, an API layer can be marked with an orientation identifier. In some embodiments, the orientation identifier can be applied with a jewelry stamp. In some embodiments, there are more than one orientation identifiers. These orientation identifiers can be applied at multiple locations on the non-API or API layer. The orientation identifier can be any type of identification mark such as letter(s), number(s), words, images, shapes, etc. In some embodiments, the orientation identifier is a stamp on a layer. For example, FIG. 11A illustrates an image of a drug delivery device showing the orientation identifier 105 (e.g., "PT"). Thus, a surgeon can identify the orientation identifier in the patient during operation to know which side of the drug delivery device has the drug containing layer. For example, when the API layer is oriented away from the reader (i.e., towards the target tissue), the orientation identifier (e.g., "PT") is also oriented properly as shown in FIG. 11B. In other words, when the drug delivery device is placed correctly on the targeted tissue site with the API layer side against the targeted tissue, the orientation identifier (e.g., the "PT") can be legible and in the correct orientation for the surgeon to distinguish the orientation identifier.

Figure 12:
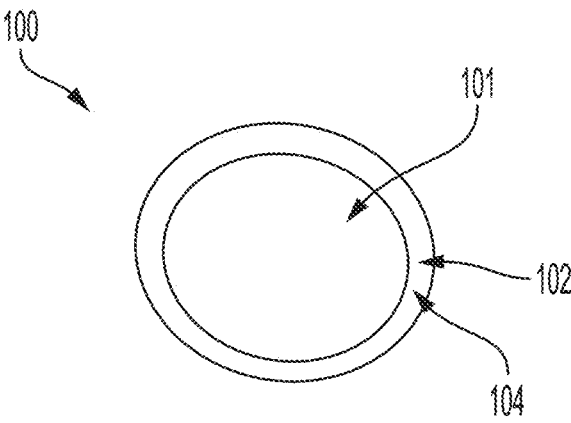
FIG. 12 illustrates another view of a drug delivery device in accordance with some embodiments disclosed herein.
Figure 13A:
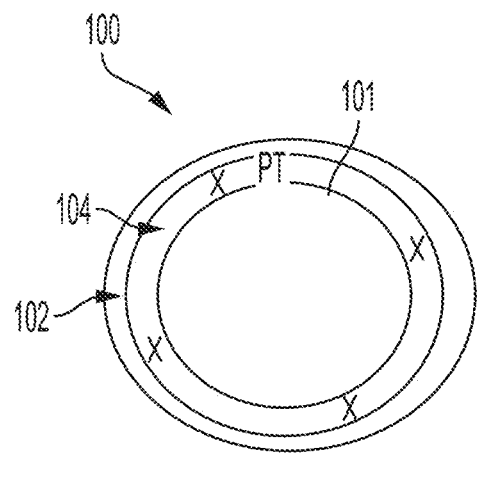
FIG. 13A illustrates locations (X) for attaching sutures (e.g., fixation/cardinal sutures) to a drug delivery device in accordance with some embodiments disclosed herein.
Figure 13B:
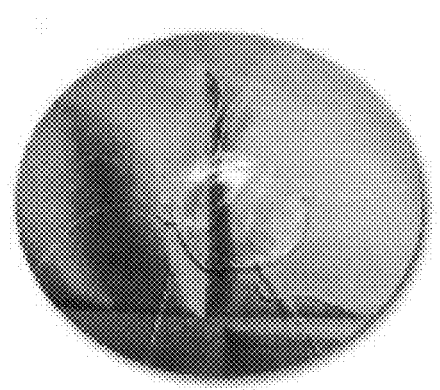
FIG. 13B illustrates an image of a drug delivery device with sutures attached ready to be implanted in accordance with some embodiments disclosed herein.
Figure 14A:
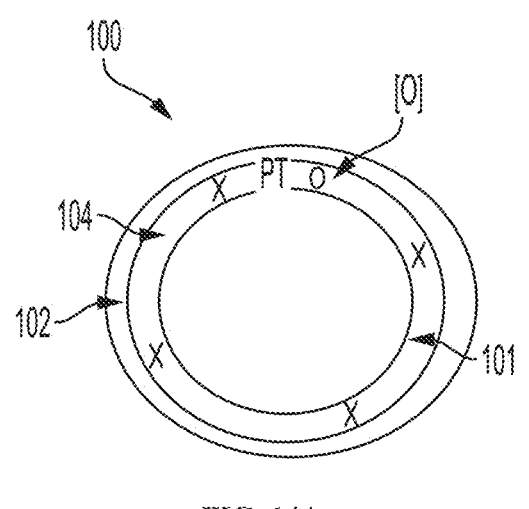
FIG. 14A illustrates an example location ([0]) for attaching an orientation identifying suture (e.g., prolene suture) to a drug delivery device in accordance with some embodiments disclosed herein.
Figure 14B:
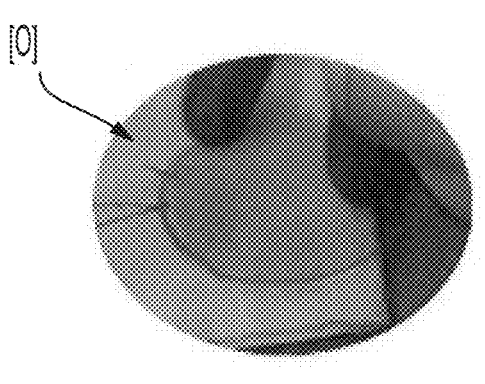
FIG. 14B illustrates an image of a drug delivery device with an orientation identifying suture (e.g., prolene suture) in accordance with some embodiments disclosed herein.
Figure 15A:
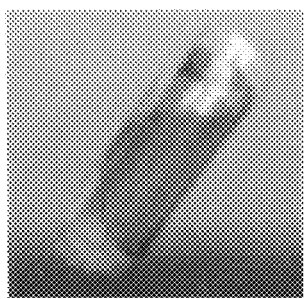
FIG. 15A illustrates a rolled up drug delivery device for implantation in accordance with some embodiments disclosed herein.
Figure 15B:
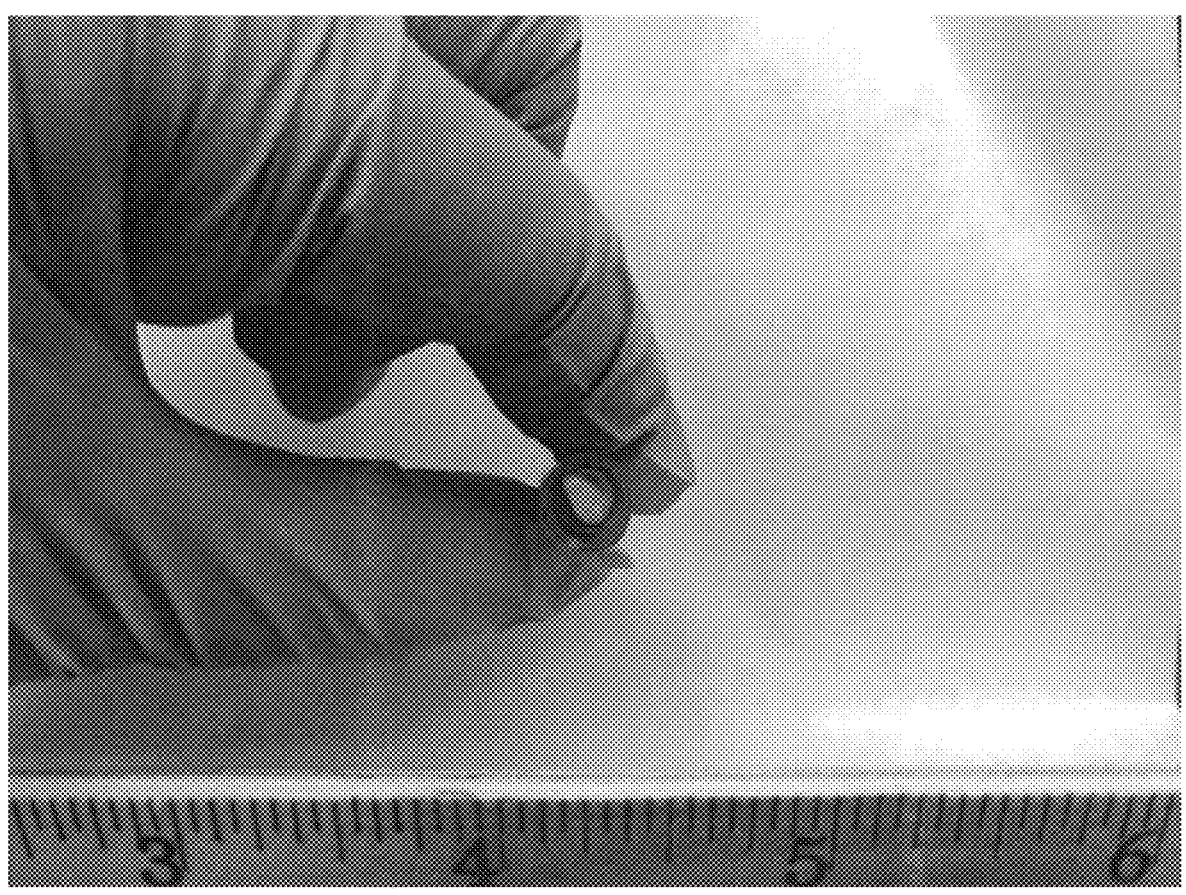
FIG. 15B illustrates an image of a rolled up drug delivery device for implantation in accordance with some embodiments disclosed herein.

Besides also having an orientation identifier, the portion of the non-API layer that extends beyond the API layer can also be used to suture the drug delivery device to the targeted tissue in the patient. FIG. 12 provides another example of the non-API layer with a rim 104 extending beyond the API-layer. For example, after locating the orientation identifier of the drug delivery device and orienting the drug delivery device properly, resorbable sutures such as 3-0 Vicryl with SH needle attached or equivalent can be attached to the portion of the non-API layer (i.e., the rim) that extends beyond the API layer. In addition, one can also use Lapra-Ty® and absorbable suture clips. As such, once the suture is in place, clips can be placed to fix them without needing to tie knots, thereby possibly reducing time to place the patch on the targeted tissue. In some embodiments, the sutures can be placed at approximately evenly spaced locations around the rim. For example, four sutures can be placed at four approximately evenly spaced locations around the rim representing the four cardinal directions. FIGS. 13A and 13B illustrate images showing location for attaching four sutures (FIG. 13A) and a sample of the sutured drug delivery device ready to be implanted (FIG. 13B). This technique can allow surgeons to implant more quickly by avoiding the added work of suturing through the patch in the body. In some embodiments, another suture (e.g., a different color suture such as Prolene or equivalent) can be placed near one of the cardinally placed sutures as another orientation identifier. For example, a different color suture can be placed clockwise near a cardinally placed suture as another orientation identifier as shown in FIGS. 14A-B. This orientation identifying suture may not be used for fixation to the target tissue. Prior to attaching the sutures, if the implant feels cool or stiff, it can be warmed by the hands or submerged in warm saline prior to attaching the sutures.

In some embodiments, drug delivery device can include anatomical marker(s). In some embodiments, an API layer and/or a non-API layer can include an anatomical marker(s). In some embodiments, the anatomical marker can be adhered or connected to the drug delivery device. In some embodiments, the anatomical marker(s) can be adhered or connected to an API layer and/or a non-API layer. The anatomical marker can be used by a physician to identify the drug delivery device in the patient using a wide variety of imaging techniques. The physician can then monitor the progress and/or location of the drug delivery device with respect to the tumor. In some embodiments, the anatomical marker can be a radiopaque marker, x-ray markers, lead markers, or similar marker(s).

Implantation

Next, the suture prepared drug delivery device can be folded and/or rolled into a tubular (e.g., cigar) shape just under the diameter (3 mm to 12 mm (e.g., 3, 5, 8, 10, 12 mm)) trocar (with sutures and intact needle already tied on). In some embodiments, the drug delivery devices can be folded and/or rolled just under 3 mm to 12 mm (e.g., 3, 5, 8, 10, 12 mm trocar) depending on the trocar being utilized. For example, if a 10 mm trocar is used during surgery, the suture prepared drug delivery device can be rolled into a tubular shape just under 10 mm in diameter. In some embodiments, the drug side can be on the inside or the outside of the tubular roll. FIGS. 15A-D illustrates a rolled drug delivery device. Prior to rolling, if the implant feels cool or stiff, it can be warmed by the hands or submerged in warm saline prior to rolling.

After being rolled, the drug delivery device can be inserted through the intended trocar port. The drug delivery device will typically unfurl and become flat once through the trocar. However, the drug delivery device can also be flattened out using typical surgical tools such as laparoscopic bowel graspers. Once flattened, the drug delivery device can be guided onto the targeted tissue. Once on the target area, a camera can be utilized to make sure that the drug delivery device is properly oriented. In other words, a surgical camera can be utilized to make sure that the API layer is facing towards the targeted tissue. A surgeon can look for an orientation identifier on the drug delivery device to determine proper orientation. For example, when the drug delivery device is placed correctly on the targeted tissue with the API layer against the targeted tissue, the "PT" can be legible and in the correct orientation for the surgeon to distinguish the orientation identifier. As such, the orientation identifier can be visible during open, laparoscopic, endoscopic, or robotic surgery. In some embodiments, the surgeon can use the camera to view the suture orientation identifier on the drug delivery product to confirm that the non-API layer is facing away from the targeted tissue. For example, returning to FIG. 14A, if the surgeon sees that the suture orientation identifier is oriented as if in a mirror image, counterclockwise, the surgeon can flip the drug delivery device over such that the suture orientation identifier is clockwise from the fixation suture prior to suturing in place. FIGS. 16A-16B illustrate this point. Failure to confirm proper orientation could result in release of the API to non-target sites.

Figure 17:
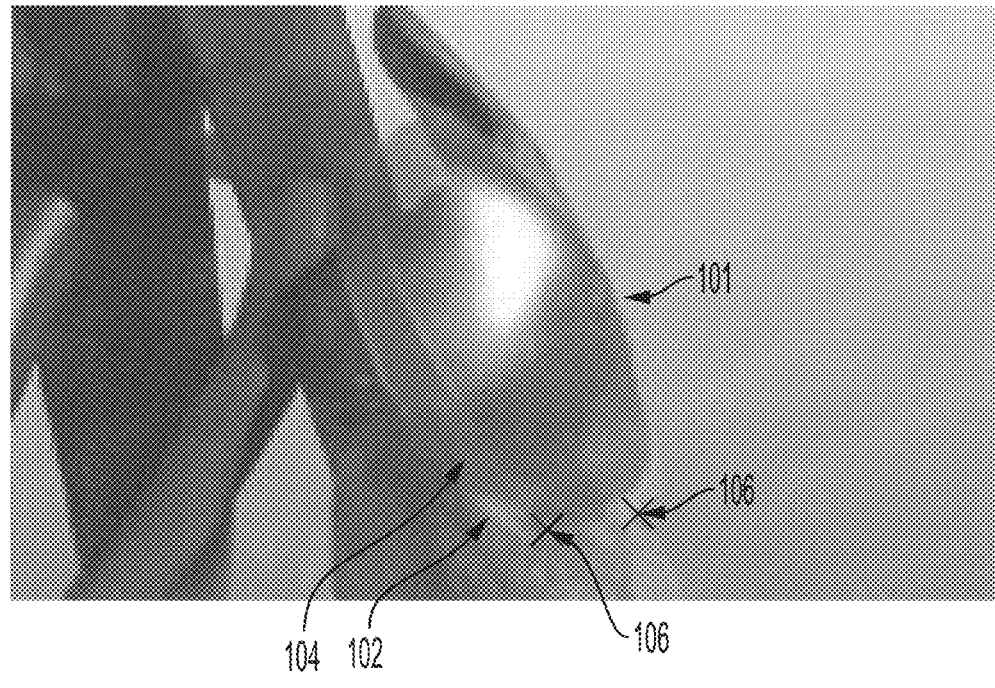
FIG. 17 illustrates an example of a drug delivery device sutured in place in accordance with some embodiments disclosed herein.

Once the correct placement and orientation of the drug delivery device is confirmed, the drug delivery device can be sutured in place. For example, the drug delivery device can be sutured in place one at a time with the previously attached sutures to the area around the targeted tissue and/or the targeted tissue itself. FIG. 17 illustrates an example of a drug delivery device sutured in place by sutures 106.

Drug Delivery Device Properties

In some embodiments, the drug delivery devices disclose herein can be transparent, medium to light brown with a clear rim indicating two sides. The drug delivery devices may have no visible foreign particulate matter on the surface or cracks. In addition, the orientation indicator can be clearly marked on the clear rim to allow the surgeon to distinguish the non-API side from the API side.

In some embodiments, the drug delivery device can be circular in nature if it was formed from a circular mold such as an evaporation dish or a petri dish. In some embodiments, the diameter of the drug delivery device can be at least about 1 cm, at least about 3 cm, at least about 5 cm, or at least about 6 cm. In some embodiments, the diameter of the drug delivery device can be at most about 10 cm, at most about 8 cm, at most about 7 cm, or at most about 6 cm. In some embodiments, the diameter of the drug delivery device can be about 3-9 cm, about 4-8 cm, about 5-7 cm, about 5.5-6.5 cm, or about 6.1-6.3 cm.

In some embodiments, an outer perimeter of an API layer can be inset relative to an outer perimeter of a non-API layer such that a portion (i.e., the rim) of a non-API layer extends beyond the API layer by an average of about 0.1-10 mm, about 0.5-8 mm, or about 1-5 mm around the perimeter of the API layer. This can be measured by a micrometer, average of n=5 measurements at 5 randomly selected points around the non-API layer's rim of the drug delivery device.

Figure 18A:
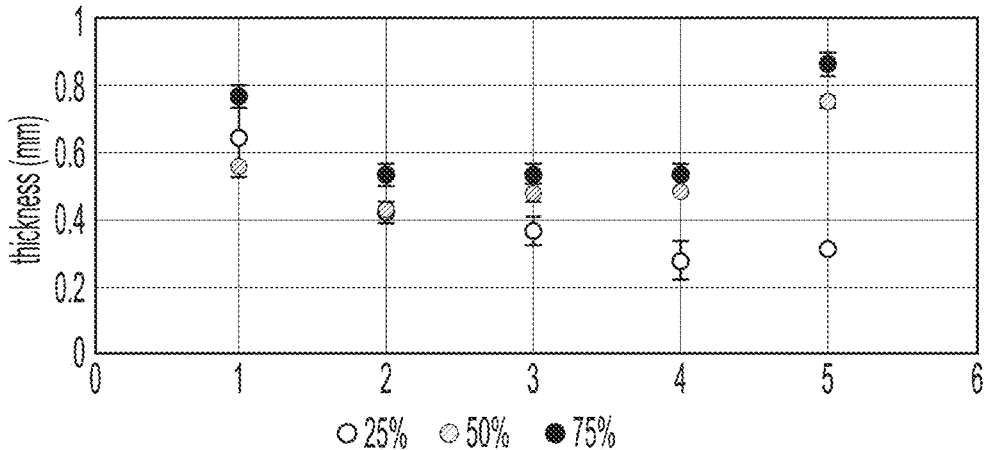
FIG. 18A illustrates the thickness measured at 3 different points on a first example film before refrigeration in accordance with some embodiments disclosed herein.
Figure 18B:
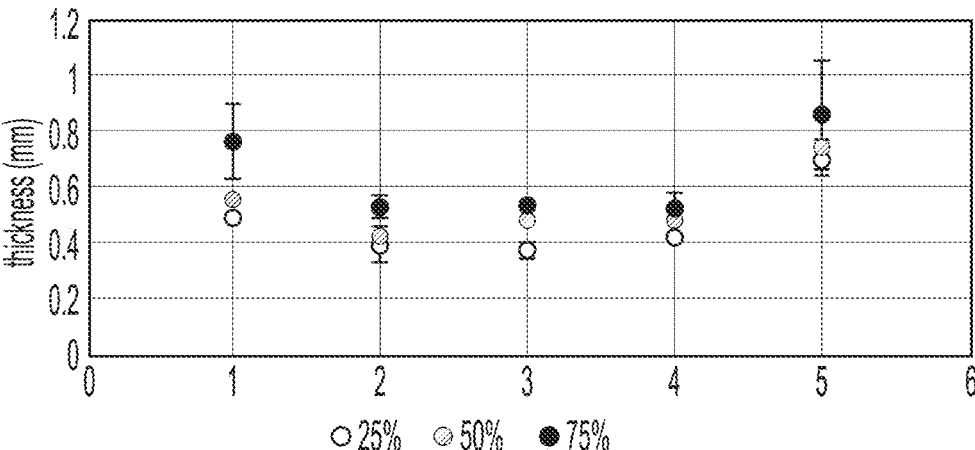
FIG. 18B illustrates the thickness measured at 3 different points on a second example film before refrigeration in accordance with some embodiments disclosed herein.
Figure 18C:
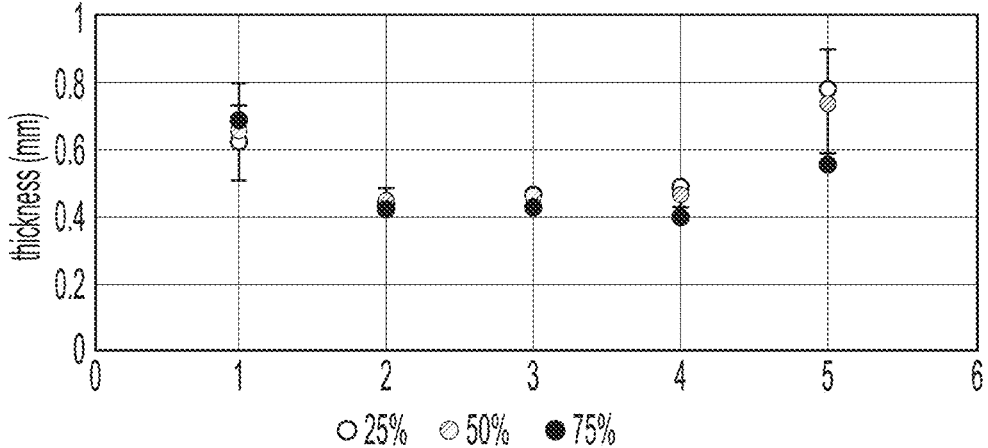
FIG. 18C illustrates the thickness measured at 3 different points on third example film after 4 weeks of refrigeration in accordance with some embodiments disclosed herein.
Figure 18D:
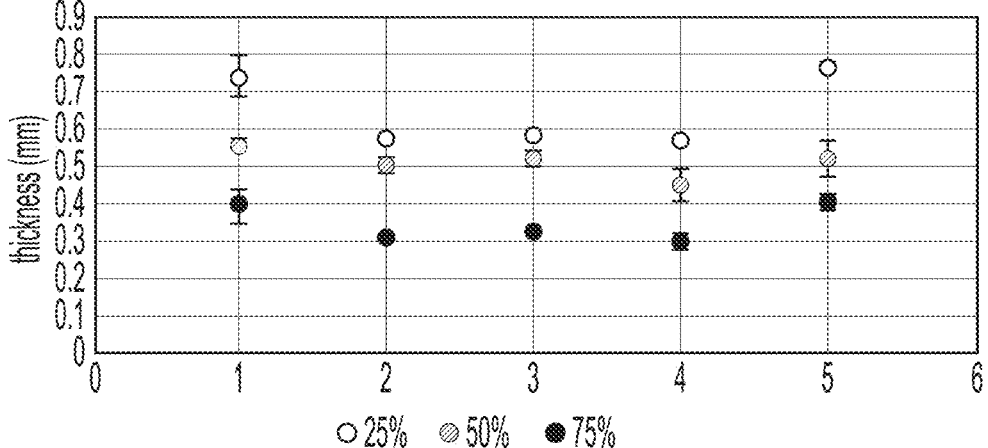
FIG. 18D illustrates the thickness measured at 3 different points on a fourth example film after 11 weeks refrigeration in accordance with some embodiments disclosed herein.
Figure 19:
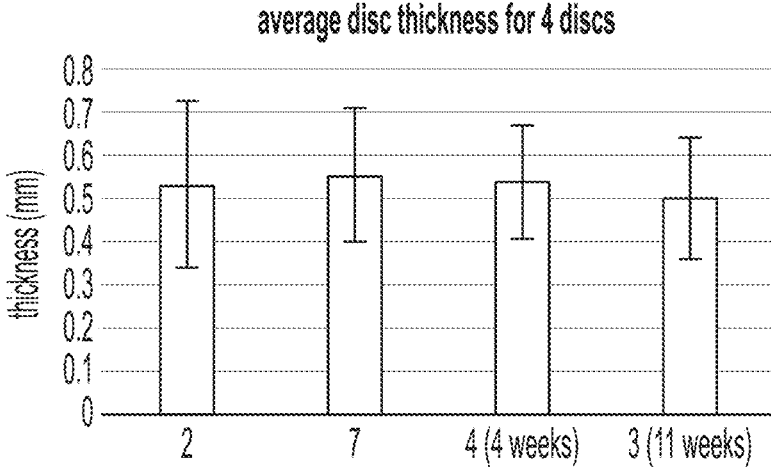
FIG. 19 illustrates the average thickness for the four example films measured in accordance with some embodiments disclosed herein.

The thicknesses of films were measured by the following protocol: (1) the API (first layer) layer was facing down; (2) the devices were oriented so that three lines at 25%, 50%, and 75% down the device could be determined consistently; (3) the micrometer was calibrated to zero when fully closed (not forcefully tightened); (4) using the micrometer, the devices were measured at 5 different points along each line; (5) step 4 was repeated 3 times so that a total of 15 measurements were available for each line. Four films containing a first layer of 0.8-1 g of PLGA 50:50, and 40-100 mg acetone and a second layer on a side of the first layer made up of 0.8-1 g PLGA 75:25 and 40-100 mg acetone) were tested. FIG. 18A illustrates the thickness measured at 3 different points on the first device before refrigeration, FIG. 18B illustrates the thickness measured at 3 different points on second device before refrigeration, FIG. 18C illustrates the thickness measured at 3 different points on the third device after 4 weeks of refrigeration, and FIG. 18D illustrates the thickness measured at 3 different points on the fourth device after 11 weeks of refrigeration. The refrigeration temperature was about 2-8° C. FIG. 19 illustrates the average thickness for the four example devices measured in accordance with some embodiments disclosed herein.

In some embodiments, the average thickness of the drug delivery device can be at least 10 microns, at least 25 microns, at least 50 microns, at least 100 microns, at least 200 microns, at least 300 microns, at least 400 microns, at least 500 microns, at least 550 microns, at least 600 microns, at least 750 microns, at least 1000 microns, at least 1500 microns, at least 2000 microns, at least 2500 microns, at least 3000 microns, at least 3500 microns, at least 4000 microns, at least 4500 microns, or at least 5000 microns. In some embodiments, the drug delivery device can be at most 5000 microns, at most 4500 microns, at most 4000 microns, at most 3500 microns, at most 3000 microns, at most 2500 microns, at most 2000 microns, at most 1500 microns, at most 1000 microns, at most 900 microns, at most 750 microns, at most 600 microns, at most 500 microns, at most 300 microns, at most 200 microns, or at most 100 microns. In some embodiments, the average thickness of the drug delivery device can be about 100-1500 microns, about 200-900 microns, about 300-900 microns, about 400-800 microns, about 430-730 microns, about 500-600 microns, or about 580 microns.

In some embodiments, the average thickness of an API and/or non-API layer can be at least 1 micron, at least 10 microns, at least 25 microns, at least 50 microns, at least 100 microns, at least 250 microns, at least 300 microns, at least 400 microns, at least 500 microns, at least 750 microns, at least 1000 microns, at least 1500 microns, at least 2000 microns, at least 2500 microns, at least 3000 microns, at least 3500 microns, at least 4000 microns, or at least 4500 microns. In some embodiments, the average thickness of an API and/or non-API layer can be at most 5000 microns, at most 4500 microns, at most 4000 microns, at most 3500 microns, at most 3000 microns, at most 2500 microns, at most 2000 microns, at most 1500 microns, at most 1000 microns, at most 750 microns, at most 600 microns, at most 500 microns, at most 400 microns, at most 350 microns, at most 300 microns, at most 250 microns, at most 200 microns, at most 150 microns, at most 100 microns, at most 50 microns, at most 25 microns, or at most 10 microns. In some embodiments, the average thickness of an API and/or non-API layer can be about 50-500 microns, about 100-450 microns, about 150-450 microns, about 200-400 microns, about 215-365 microns, about 250-300 microns, or about 290 microns. In some embodiments, the thickness of the drug delivery device can be selected based on the desired degradation/API release kinetics. The average thickness can be measured by a micrometer, average of n=5 measurements at 5 randomly selected points on the drug delivery device.

Figures 20A, 20B:
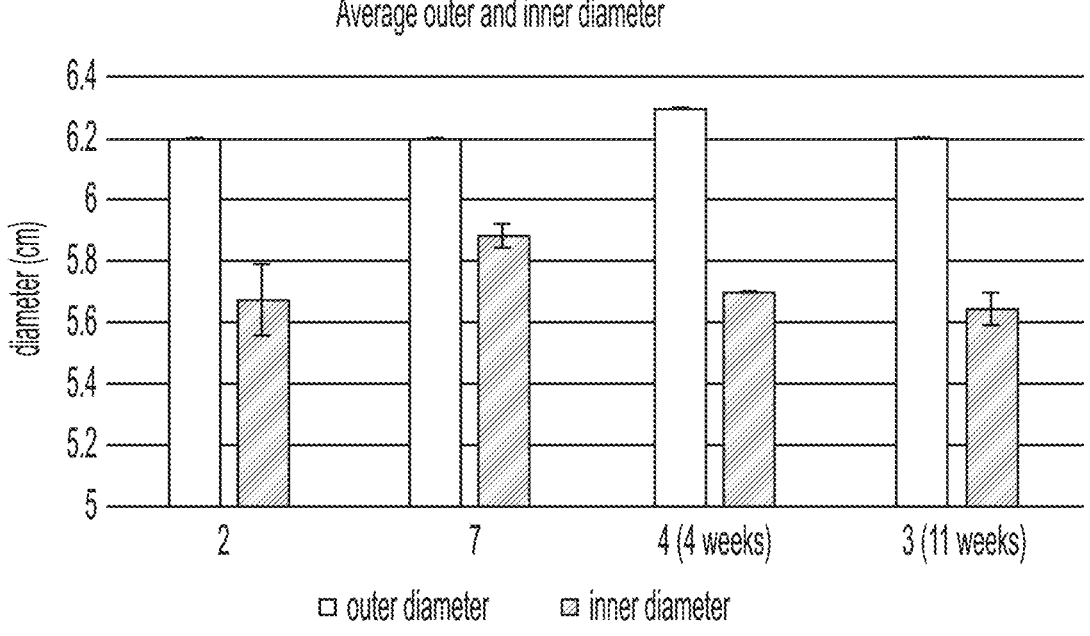
FIG. 20A illustrates the diameters for the four example films measured in accordance with some embodiments disclosed herein.
FIG. 20B illustrates the average diameters for the four example films measured in accordance with some embodiments disclosed herein.

The diameter of the drug delivery device can be measured by the following protocol: (1) the outer diameter (i.e., diameter of the non-API layer) can be measured by placing the ruler along the diameter, which included the external rim of the non-API layer, and reading the ruler carefully; (2) step 1 was repeated 15 times, moving the device each time, so as to have a total of 15 readings; (3) the inner diameter (i.e., diameter of the API layer) was measured similarly, except that the external rim was not included in the measurement. FIGS. 20A-20B illustrates the diameters and average diameters for the four example devices measured in accordance with some embodiments disclosed herein. Accordingly, the average thickness and diameters of the drug delivery devices do not change significantly under the intended storage condition (e.g., about 2-8° C.) over a period of time.

Figure 21A:
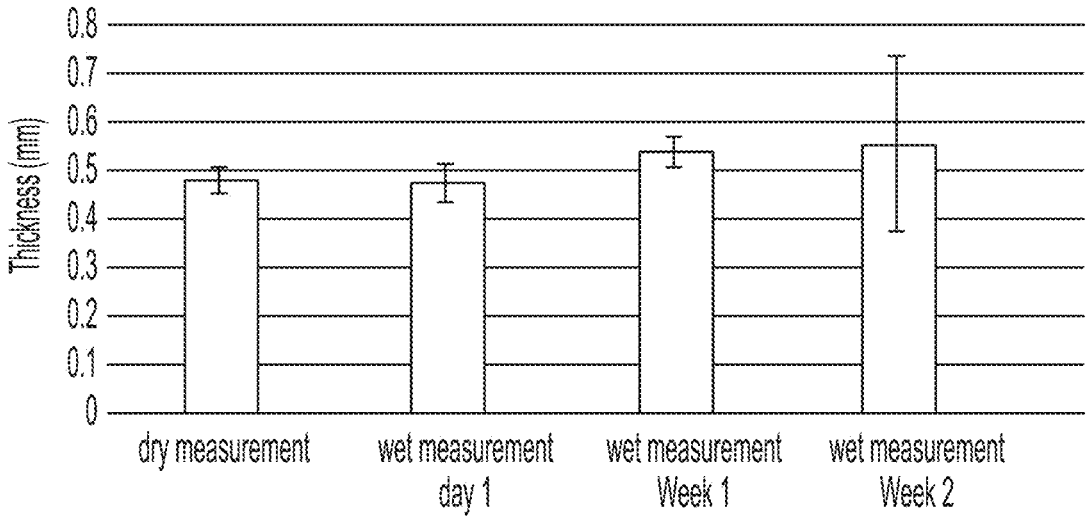
FIG. 21A illustrates the thicknesses of the three samples measured dry vs. wet in accordance with some embodiments disclosed herein.
Figure 21B:
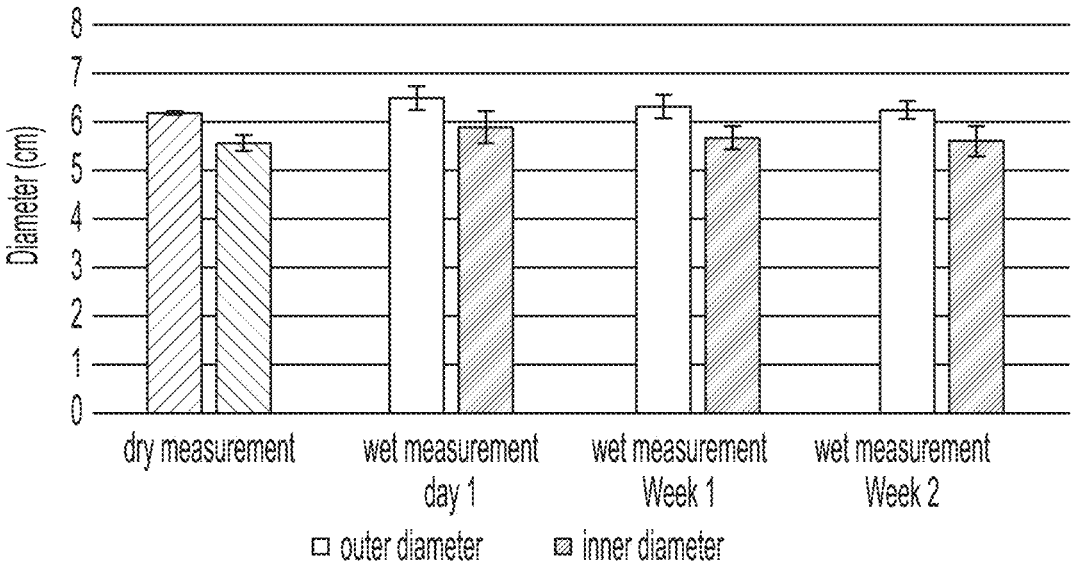
FIG. 21B illustrates the diameters of the three samples measured dry vs. wet in accordance with some embodiments disclosed herein.

The diameters and thicknesses of 3 films containing a first layer of 0.8-1 g of PLGA 50:50 and 40-100 mg acetone and a second layer on a side of the first layer made up of 0.8-1 g PLGA 75:25 and 40-100 mg acetone) were tested to compare their dry vs. wet measurements. The films were measured at Day 0 (before being placed in buffer solution) and then measured again after being placed in 60 mL of Sorenson's buffer after 1 day, 7 days, and 14 days. FIG. 21A illustrates the average thickness for the films measured dry vs. wet and FIG. 21B illustrates the average diameters for the films measured dry vs. wet.

Figure 22:
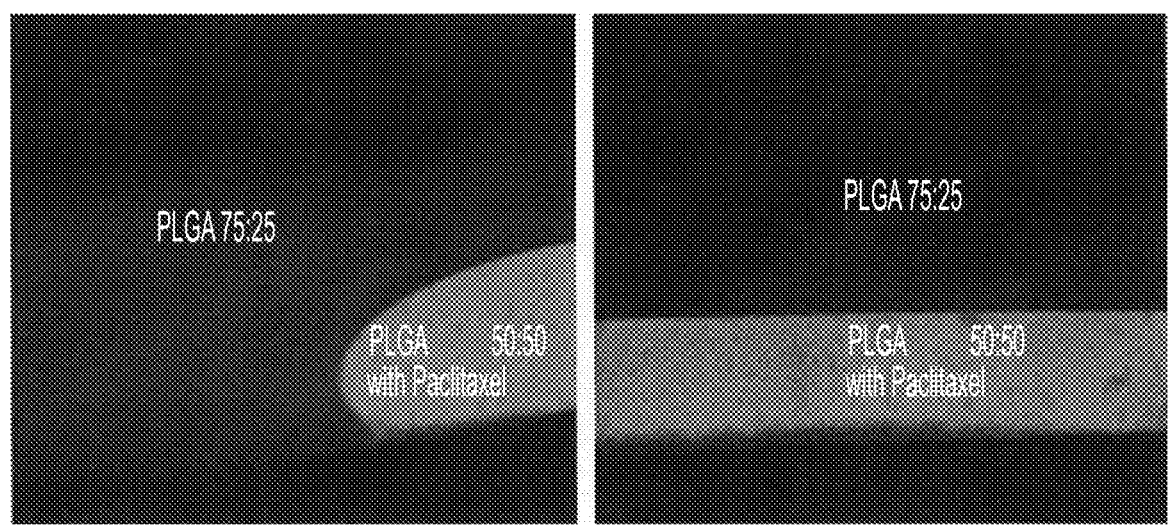
FIG. 22 illustrates a fluorescent viewed drug delivery device under a confocal microscope in accordance with some embodiments disclosed herein.

In order to determine if the API is contained only in the API layer as well as evenly distributed in the API layer, a drug delivery device containing a first layer of 0.8-1 g of PLGA 50:50, 100 mg paclitaxel, 300 micrograms fluorescently labeled paclitaxel, and 40-100 mg acetone and a second layer on a side of the first layer made up of 0.8-1 g PLGA 75:25 and 40-100 mg acetone was viewed under a confocal microscope as shown in FIG. 22. As seen in FIG. 22, it appears that the API and non-API layers are very distinct indicating that the paclitaxel can be contained only within the API layer and even distributed within the API layer. As such, the API layers of the drug delivery devices disclosed herein can have the API uniformly and homogeneously distributed throughout the layer.

Figure 23A:
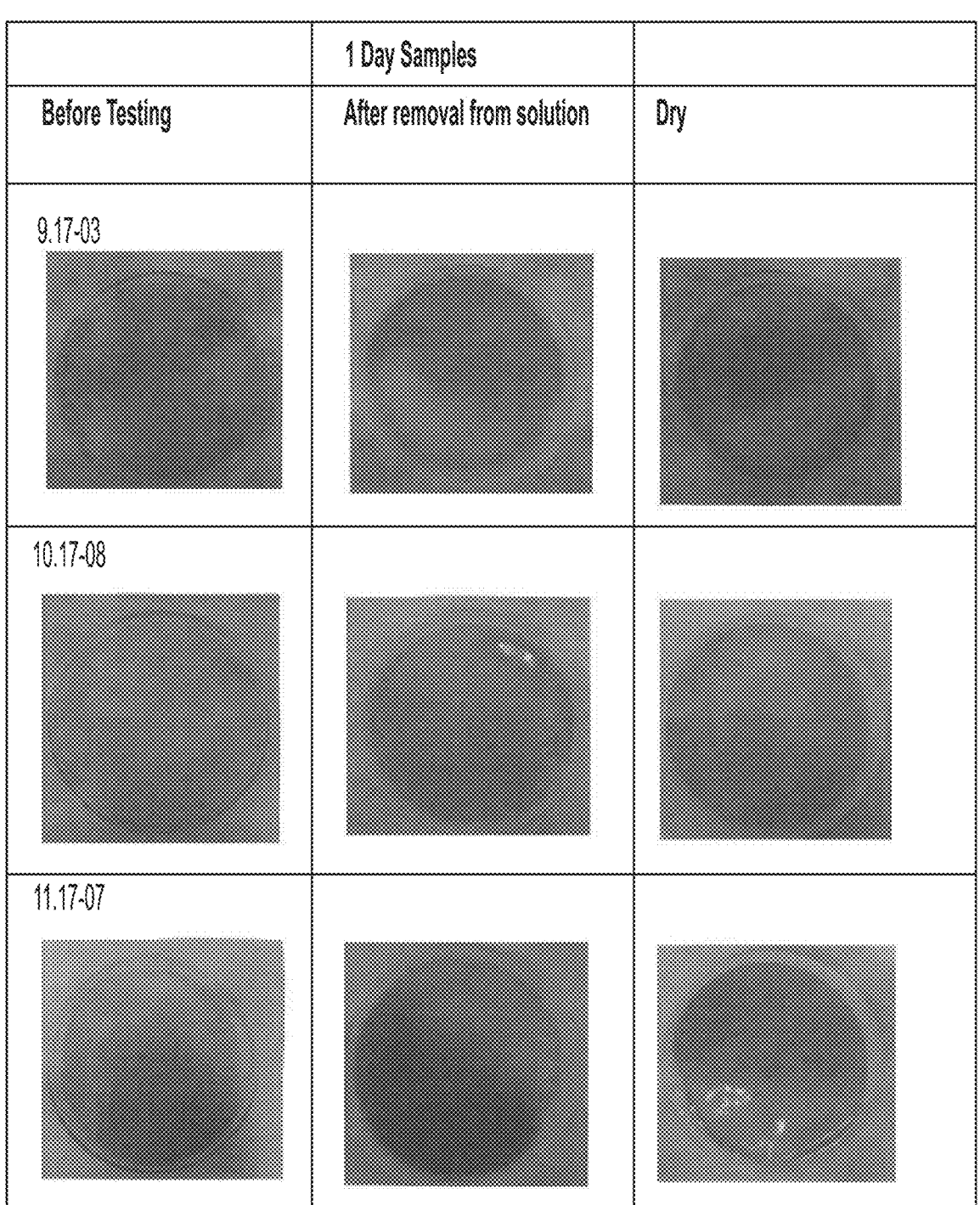
FIG. 23A illustrates the degradation of a sample film after 1 day in a buffer solution in accordance with some embodiments disclosed herein.
Figure 23B:
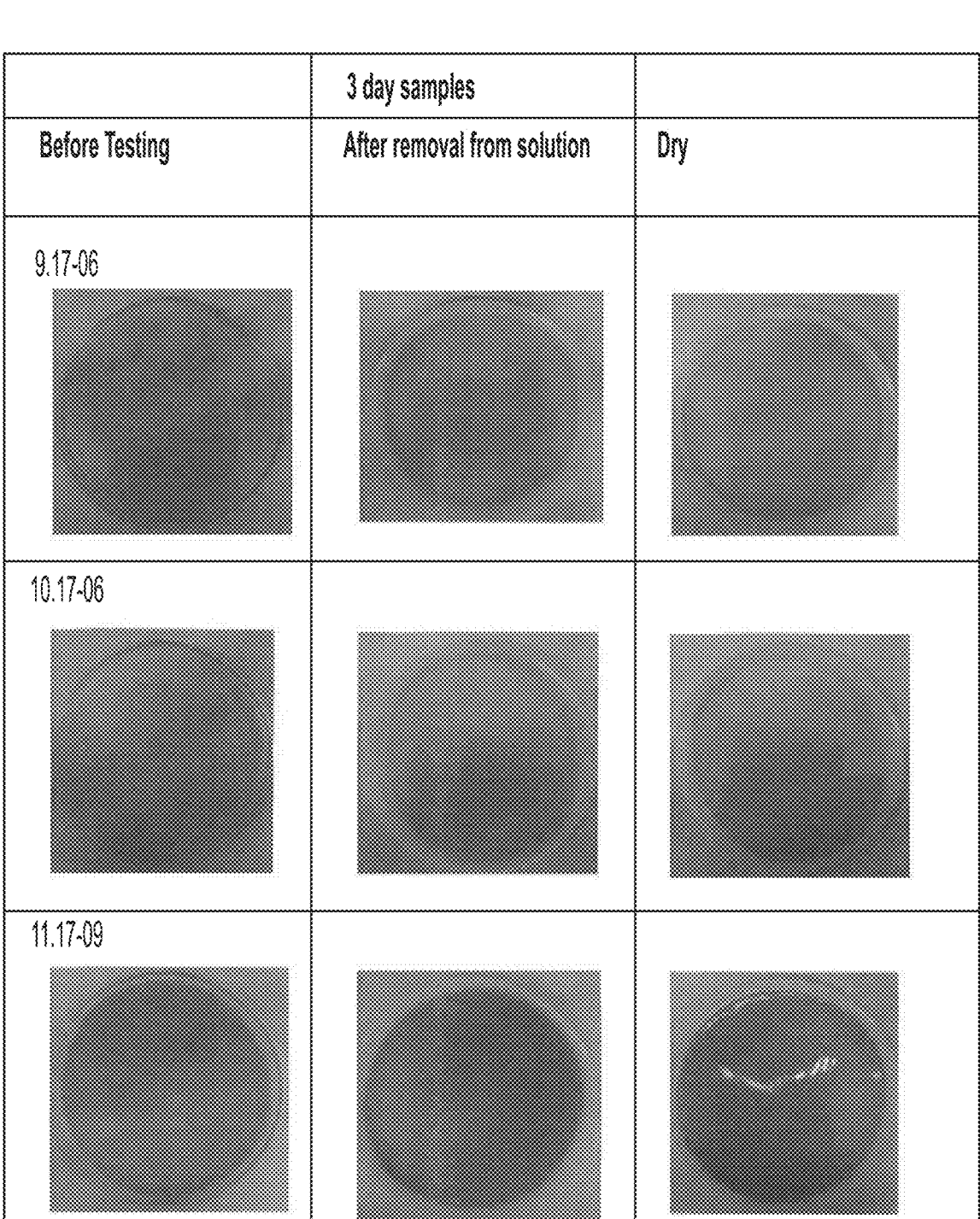
FIG. 23B illustrates the degradation of a sample film after 3 days in a buffer solution in accordance with some embodiments disclosed herein.
Figure 23D:
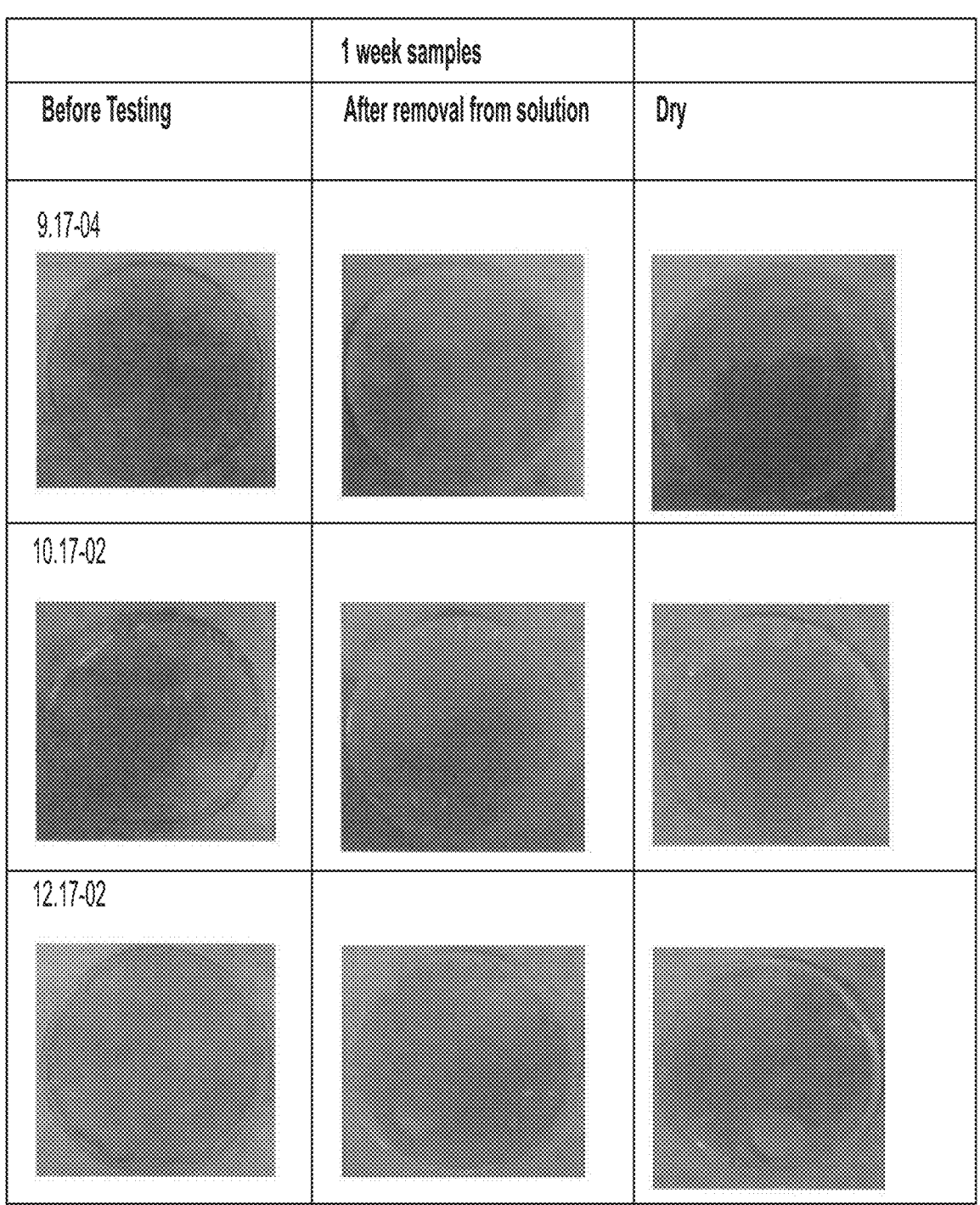
FIG. 23D illustrates the degradation of a sample film after 7 days in a buffer solution in accordance with some embodiments disclosed herein.
Figure 23F:
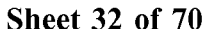
FIG. 23F illustrates the degradation of a sample film after 3 weeks in a buffer solution in accordance with some embodiments disclosed herein.
Figure 231:
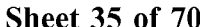
Figure 24:
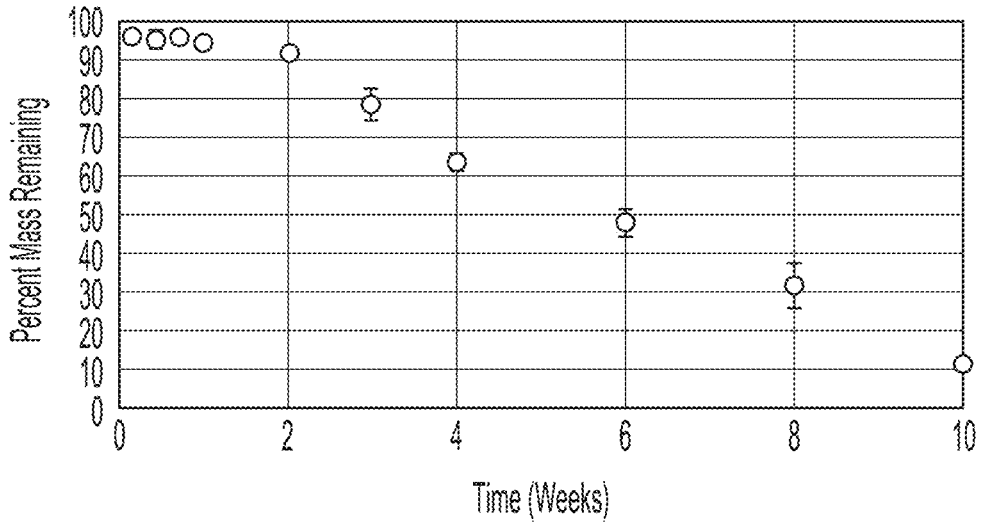
FIG. 24 illustrates a graph of percent mass remaining over time (dry mass/initial mass*100) for the samples tested for degradation rate in accordance with some embodiments disclosed herein.
Figure 25:
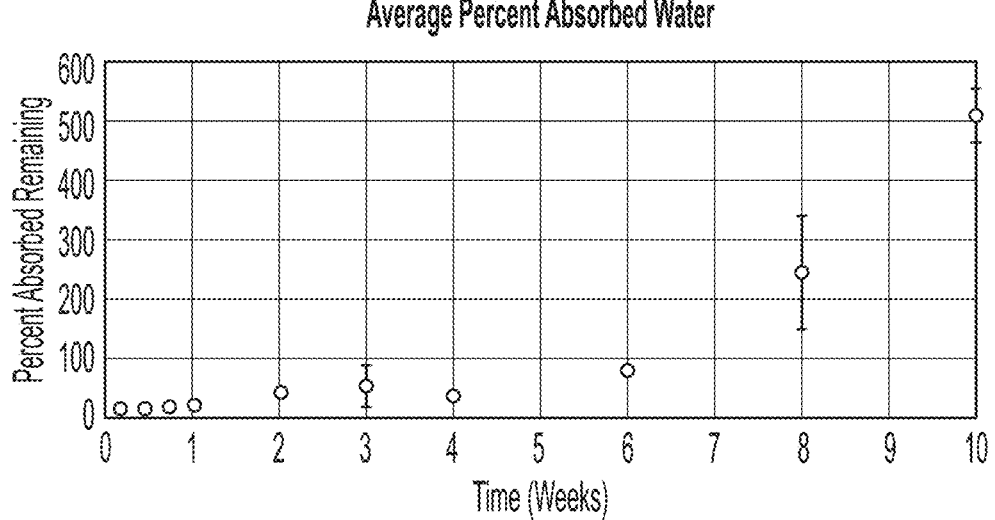
FIG. 25 illustrates a graph of percent of water absorbed by the disc over time ((wet mass–dry mass)/dry mass*100) for the samples tested for degradation rate in accordance with some embodiments disclosed herein.

A set of 30 films containing a first layer of 0.8-1 g of PLGA 50:50 (and acetone) and a second layer on a side of the first layer made up of 0.8-1 g PLGA 75:25 (and acetone) were degraded in vitro in aqueous media to determine the rate of degradation of the polymer and water absorbed by the polymer. The films were placed in 15 mL of Sorenson's buffer (0.2M, pH 7.4) and incubated at 37° C. on a shaker set to 50 rpm. Samples were removed, dried, and weighed at time points between 1 day and 10 weeks to establish mass loss at a variety of time points. Results of testing in these conditions demonstrated that the devices degrade slowly over the first week. At that point the rate of mass loss increases, and the devices lose mass in a linear fashion. As such, the layers of the drug delivery device (and the drug delivery device itself) can degrade substantially linearly or linearly. Only 10% of the initial polymer mass remains at 10 weeks. Images taken of the discs at different time points also show that the PLGA 50:50 degrades more quickly than the PLGA 75:25, and appears to be fully degraded by the 6 week time point indicating that the API would be fully released by 6 weeks. All test samples were weighed and imaged prior to testing. Then each was placed in 15 mL of Sorenson's buffer (pH 7.4). Sample containers were sealed with parafilm and placed on an incubating shaker set to 37° C. and 50 rpm. Sample pH was tested and titrated with 1.0 N NaOH back to the acceptable pH range (7.4+/−0.3) each week. Samples were removed at predetermined time points (1 day, 3 days, 5 days, 1 week, 2 weeks, 3 weeks, 4 weeks, 6 weeks, 8 weeks, and 10 weeks). Removed samples were imaged, weighed, and then placed in a petri dish covered with a kim wipe. The petri dish was then placed in a desiccator under vacuum for up to one week to dry. Dry samples were imaged a third time, and weighed. This allowed determination of polymer mass loss and water absorbed during testing. For the 8 and 10 week time points, the sample solution was also filtered through grade 1 filter paper to collect visible particulates in the solution. The filters were preweighed and placed in a petri dish with the intact portion of the sample to dry. The weight of the particulate matter was included in the remaining weight of the sample. Images of the degradation samples before degradation, after removal from solution, and after drying can be found in FIGS. 23A-J. Over the first week (FIGS. 23A-D), samples hydrated, but did not appear to change substantially in comparison with their initial appearance once they were dried. At two weeks (FIG. 23E), there were some changes in the appearance of the films, and at 3 weeks (FIG. 23F) it was clear that the PLGA was degrading enough that it could be seen. The PLGA 50:50 layer is typically light to medium brown in color and the PLGA 75:25 is typically clear or white. In FIG. 23F, it appears that the PLGA 50:50 layer is significantly degraded at the 3 week time point, and by 4 weeks (FIG. 23G), most of the PLGA 50:50 is gone, and in one sample, the PLGA 75:25 also started to degrade through. At 6 weeks (FIG. 23H), the remaining sample was very thin and brittle, which caused some samples to break when dried. At 8 and 10 weeks (FIGS. 23I-J) little intact sample remained, and particulate matter was collected from the solution by filtration (not pictured). FIG. 24 illustrates a graph of percent mass remaining over time (dry mass/initial mass*100). After a slow loss to about 90% mass remaining over the first two weeks, the samples degraded more rapidly over the following 8 weeks to approximately 10% mass remaining. FIG. 25 shows the percent of water absorbed by the disc over time ((wet mass−dry mass)/dry mass*100). Water appears to be absorbed slowly over the first two weeks, then increases rapidly as the polymer degrades. Thus, it appears that the film degrades slowly over the first two weeks, then degrades linearly after two weeks down to only 10% remaining at 10 weeks. The PLGA 50:50 appears to degrade first, and is almost fully degraded at 4 weeks, and fully degraded at 6 weeks. The PLGA 75:25 degrades to approximately 10% of the original mass of the device by 10 weeks.

In some embodiments, the drug delivery device can be configured to release the API according to a defined release kinetic profile. In some embodiments, the release of the API can be delayed (or only a sub-therapeutically effective amount of the API can be released during the delay period) after the device is implanted at the target tissue site such that the patient's body can recover from the implantation surgery prior to releasing the drug. The delay can allow for some healing at the implantation site before the release of the API, thereby potentially reducing risks associated with swelling, perforation, bleeding, infection, and other potential issues. In some embodiments, the API delay release period can be at least 1 day, at least 3 days, at least 7 days, at least 9 days, at least 10 days, at least 12 days, at least 14 days, at least 16 days, at least 18 days, or at least 21 days. In some embodiments, the API delay release period can be at most 28 days, at most 25 days, at most 21 days, at most 18 days, at most 15 days, at most 14 days, at most 12 days, at most 10 days, at most 8 days, at most 7 days, at most 5 days, or at most 3 days. In some embodiments, the API delay release period can be 1-28 days, 1-21 days, 1-14 days, or 7-14 days. After the delay period, the API can have a substantially linear or linear release rate.

Accordingly, an API layer with PLGA 50:50 can begin to release the API at the target tissue at approximately 1 week after implantation and the API can be fully released by 4 weeks after implantation. This can align well with the degradation data—it takes time for the polymer to hydrate, but at 4 weeks most of the PLGA 50:50 is gone, so most of the API will have been released. In addition, a non-API layer made with PLGA 75:25 can serve as a mechanism that forces the API to be released only from one face of the device. The PLGA 75:25 layer was thinned by 4-6 weeks, but only one sample formed a small hole before the PLGA 50:50 layer was completed degraded. This can prevent the API from leaking away from the targeted tissue site as well as anchor the device to the target site.

The degradation of biodegradable polymer in an API layer can control the release the API from the API layer during use. As such, degradation of an API layer in the drug delivery device can be tuned based on the biodegradable polymer in the API layer as well as the thickness of the API layer as the thicker the API layer the longer it will take to degrade. In some embodiments, the API layer can be configured to completely degrade within a period of at least 3 days, at least 5 days, at least 1 week, at least 2 weeks, at least 3 weeks, at least 3.5 weeks, at least 4 weeks, at least 30 days, at least 4.5 weeks, at least 5 weeks, at least 6 weeks, at least 2 months, at least 3 months, at least 4 months, at least 6 months, at least 8 months, or at least 10 months, after implantation. In some embodiments, the API layer can be configured to completely degrade within a period of at most 2 years, at most 1 year, at most 10 months, at most 8 months, at most 6 months, at most 4 months, at most 3 months, at most 2 months, at most 6 weeks, at most 5 weeks, at most 4.5 weeks, at most 30 days, at most 4 weeks, at most 3.5 weeks, at most 3 weeks, at most 2 weeks, or at most 1 week, after implantation. In some embodiments, the API layer can be configured to completely degrade within a period of about 3 days to 10 months, 1 week to 6 months, 1-6 weeks, about 2-6 weeks, about 3-5 weeks, about 3.5-4.5 weeks, or about 4 weeks (about 30 days), after implantation. "Completely degrade" or "fully degrade" used herein refers to a layer or device degrading to less than 10% of original mass within the time period. In some embodiments, the API can be released from an API layer at a rate of about at least 1 mg API/day. In some embodiments, the API can be released from the API layer at a rate of about 1-10 mg/day, about 1-5 mg/day, about 2-5 mg/day, or about 3-4 mg/day, after implantation. In some embodiments, the API can be released from the API layer at a rate of about 7-70 mg/week, about 7-35 mg/week, about 14-35 mg/week, or about 21-28 mg/week, after implantation. In some embodiments, the degradation profile of the API layer (and the API release profile) after implantation can include a delay period from about 1 day to 2 weeks. After the delay period, the degradation of the API layer (and the API release) can be substantially linear or linear.

Figures 32A, 32B:
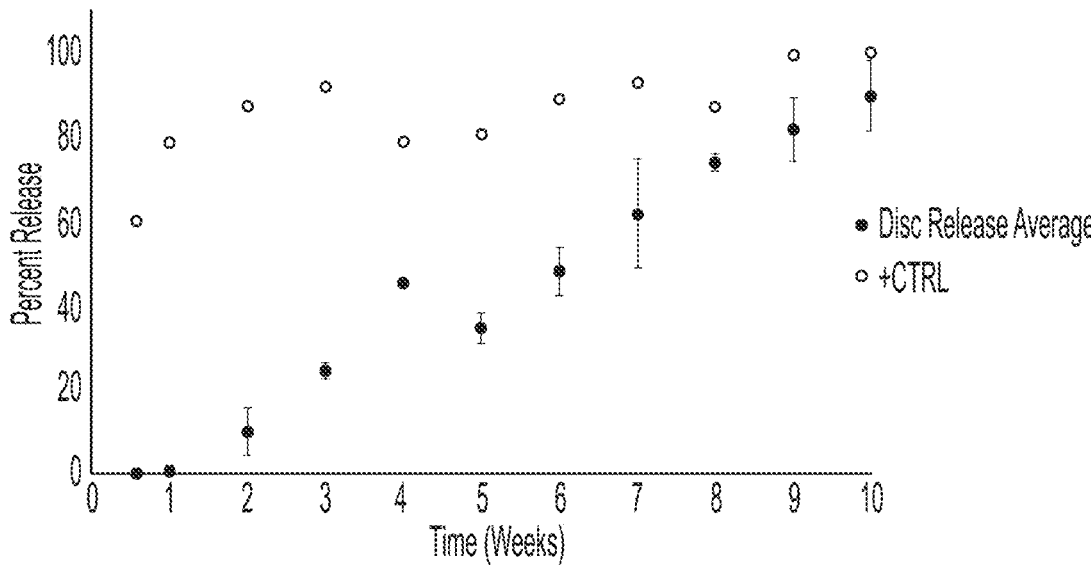
FIG. 32A illustrates the weight of the drug delivery devices without oven drying or sterilization tested for drug release rates in accordance with some embodiments disclosed herein.
FIG. 32B illustrates the cumulative drug release of drug delivery devices without oven drying or sterilization tested in accordance with some embodiments disclosed herein. Control is a single measurement—only 1× measurement per disc.
Figure 33:
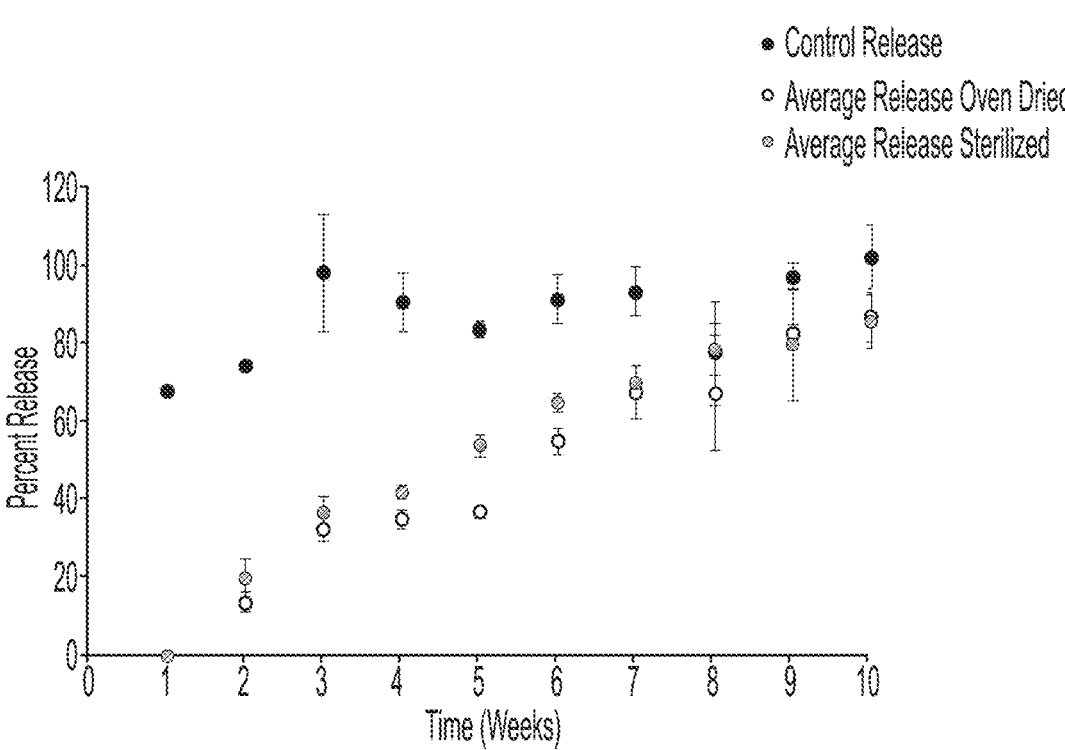
FIG. 33 illustrates the cumulative drug release of oven dried and sterilized drug delivery devices in accordance with some embodiments disclosed herein.
Figure 34:
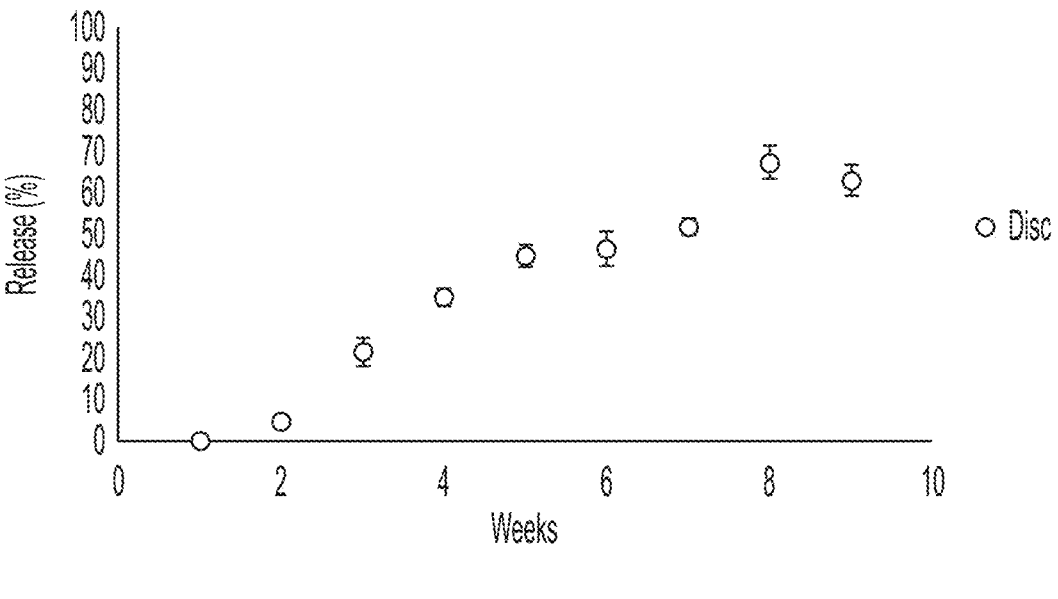
FIG. 34 illustrates cumulative drug release of a single drug delivery device with oven drying but no sterilization in accordance with some embodiments disclosed herein.

Drug release (i.e., API release) was tested in vitro in a paddle over disc (USP 5) apparatus (SOTAX). This setup is typically designed for transdermal patches, however because this setup is designed to measure unidirectional release from a patch, it was the most appropriate setup. Specifically, drug delivery devices containing a first layer of 0.8-1 g of PLGA 50:50, 100 mg paclitaxel, and 40-100 mg acetone and a second layer on a side of the first layer made up of 0.8-1 g PLGA 75:25 and 40-100 mg acetone) were placed in the SOTAX vessels with PLGA 50:50 side up in 900 mL of 1.75M sodium salicylate in 1×PBS. The water bath was set to 37° C. and the paddles were set to a stir rate of 100 rpm. No disc holder was placed in the vessel containing 104.67 mg paclitaxel as the control. The paclitaxel for the positive control (+CTRL) was weighed in a glass scintillation vial and added to the vessel dry. 2 mL samples were taken at the following time points: 4 days, 1 week, 2 weeks, 3 weeks, 4 weeks, 5 weeks, 6 weeks, 7 weeks, 8 weeks, 9 weeks, and 10 weeks. 2 mL of 1.75 sodium salicylate in 1×PBS was added after each sampling. Samples were analyzed by HPLC using a diode array detector at 229 nm. Expected concentrations of drug in each disc portion were based on an assumption of 100 mg of drug in each device. A calibration curve relating area under the curve of the paclitaxel peak (or peaks in response to temperature degradation) to the concentration as made prior to sample testing. A linear formula to calculate concentration for samples with concentrations within the range of the curve was made from the data. AUC of paclitaxel samples were then measured and concentration was calculated from the formula. If sample concentration fell above the range of the curve, samples were diluted to fall within the curve to ensure accuracy. The weights of the three drug delivery devices (i.e., discs without sterilization or oven drying) as well as the positive control are shown in FIG. 32A. FIG. 32B illustrates the average release of the drug from the three drug delivery devices as well as the drug content of the positive control over time. Additional samples were also tested that had been oven dried (three samples) and sterilized (2 samples) except this time 3 mL samples were taken instead of 2 mL samples. The samples oven dried were placed in the oven at 38° C. for 3 days and the sterilized samples were sterilized by e-beam radiation. The results of the oven dried and sterilized drug delivery devices drug release compared to the positive control are shown in FIG. 33 and FIG. 34 illustrates the drug release of an individual drug delivery device with oven drying and no sterilization. Results showed a 1-2 week delay of release of API, followed by steady linear release for 9 weeks.

In addition, degradation of a non-API layer in the drug delivery device can be tuned based on the biodegradable polymer in the non-API layer as well as the thickness of the non-API layer. In some embodiments, the non-API layer can be configured to degrade at a slower rate than an API layer such that the API is released toward the targeted tissue. In some embodiments, the non-API layer can be configured to degrade at the same rate as an API layer. In some embodiments, the non-API layer can be configured to degrade at a faster rate as an API layer. For example, in some embodiments, there may be a non-API layer on a side of the API layer that is tumor facing (and another non-API layer (i.e., a backing layer) on the other side of the API layer opposite the first non-API layer). This first non-API layer can degrade faster than the API layer such that there may be a delayed period for API release due to the degradation of the non-API layer (i.e., non-backing layer) first.

In some embodiments, the non-API layer can be configured to completely degrade within a period of at least 5 days, at least 1 week, at least 2 weeks, at least 3 weeks, at least 4 weeks, at least 5 weeks, at least 6 weeks, at least 8 weeks, at least 10 weeks, at least 11 weeks, at least 12 weeks, at least 4 months, at least 5 months, at least 6 months, at least 8 months, at least 10 months, or at least 1 year, after implantation. In some embodiments, the non-API layer can be configured to completely degrade within a period of at most 3 years, at most 2 years, at most 1 year, at most 10 months, at most 8 months, at most 6 months, at most 4 months, at most 3 months, at most 12 weeks, at most 11 weeks, at most 10 weeks, at most 8 weeks, at most 6 weeks, at most 5 weeks, at most 4 weeks, at most 3 weeks, or at most 2 weeks, after implantation. In some embodiments, the non-API layer can be configured to completely degrade within a period of about 1 week to 2 years, 1 week to 1 year, 1 week to 6 months, about 4-14 weeks, about 6-12 weeks, about 8-12 weeks, about 9-11 weeks, or about 10 weeks, after implantation.

As explained above, in order for the device to be implanted via open, laparoscopically, robotically, endoscopically, the drug delivery device can be flexible enough and/or small enough to be able to pass through a trocar or other working channel of an endoscope (e.g., robotic endoscope). A study was conducted to determine whether the surfaces of the device or the API content of the device is altered by passage through a trocar. Specifically, drug delivery devices containing a first layer of 0.8-1 g of PLGA 50:50, 90-105 mg paclitaxel, and 40-100 mg acetone and a second layer on a side of the first layer made up of 0.8-1 g PLGA 75:25 and 40-100 mg acetone) were passed through a 10 mm trocar 10 times. The samples were observed before and after, their thicknesses were measured before and after, and sample drug content was measured and compared with drug content of samples that have never been passed through a trocar. Some surface scratching was observed under microscope, but no differences in drug content were found. During handling, the drug delivery devices passed through the trocar easily. No differences were observed between the group of devices that was measured, weighed, and imaged, and the group of devices that was measured, weighed, imaged, and handled through the trocar. There were no visible changes, such as scratching of the surface, visible in the majority of the images. The clearest damage in any device appeared to have been caused to a control drug delivery device during micrometer measurements. There was no change to the dimensions or weight of the drug delivery devices. Finally, there was no difference in drug content between groups, which would have indicated drug content coming off in the trocar as measured by dissolving the device in acetonitrile and diluted 1000× for HPLC analysis in an Agilent HPLC.

Cancer Treatment

In some embodiments, the targeted tissue may be pancreatic tissue. For example, the targeted tissue may be cancerous tissue/cells (e.g., a tumor or tumors) on the pancreas. As such, the drug delivery devices disclosed herein can be used for treating tumors of the pancreas. Specifically, the various cancers that the drug delivery device can help treat include, but are not limited to, pancreatic ductal adenocarcinoma (PDAC). In some embodiments, the drug delivery devices can be used to treat resectable cancers and/or non-resectable cancers. In some embodiments, the drug delivery devices herein can be used to treat non-immediately resectable to non-metastatic cancers. In some embodiments, the drug delivery devices can be used to treat patients after cancers are resected to prevent recurrences. For example, the drug delivery devices can be used for treatment of patients with borderline resectable or locally advanced pancreatic adenocarcinoma. In some embodiments, the cancer in the pancreas treated by the drug delivery device can be a tumor in the pancreas of primary origin or metastatic spread to the pancreas. In some embodiments, the drug delivery devices can be used for treatment of patients with non-immediately resectable pancreatic cancer, non-metastatic pancreatic cancer, borderline resectable pancreatic cancer, resectable pancreatic cancer, locally advanced pancreatic cancer, metastatic pancreatic cancer, and/or metastatic spread to the pancreas.

In some embodiments, the drug delivery devices disclosed herein can be placed onto a peritumoral area of interest (API layer facing and in contact with peritumoral area of interest) and can biodegrade within the body of the patient in about 1 week to 2 years, about 1-52 weeks, about 1-26 weeks, about 1-24 weeks, about 1-20 weeks, about 1-15 weeks, about 4-12 weeks, about 6-12 weeks, about 8-12 weeks, about 9-11 weeks, or about 10 weeks of implantation. In some embodiments, the tumor may be on the inside of the organ (i.e., not on the surface) and the drug delivery device is placed on the peritumoral surface of the organ. As explained above, the drug delivery device can be placed directly onto a peritumoral area of interest (e.g., around a pancreatic tumor) using minimally invasive standard surgical techniques during routinely performed staging evaluations. In some embodiments, multiple drug delivery devices can be placed directly onto a peritumoral area of interest. In some embodiments, the drug delivery device can be rolled into a tube shape, inserted through surgical procedure, placed on the peritumoral area of interest, and sutured into place. In some embodiments, the size of the drug delivery device (e.g., diameter or surface area) can allow the surgeon to cover the targeted tissue site (e.g., the pancreatic head and neck and for the edges to drape over the region near the superior mesenteric artery and superior mesenteric vein).

Figure 26:
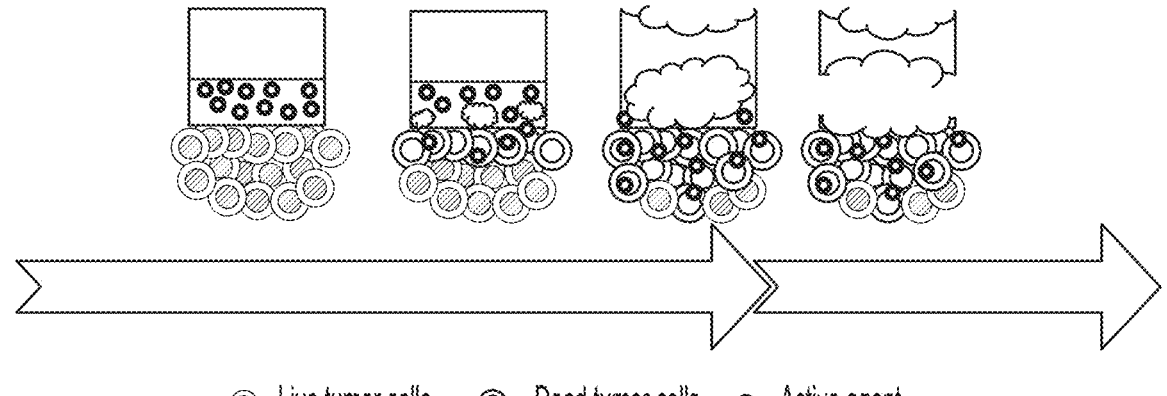
FIG. 26 illustrates an exemplary flowchart of how the drug delivery device can attack tumor cells in accordance with some embodiments disclosed herein. Specifically, an eluting layer can degrade and release drugs within the tumor (left arrow sequence) and then the backing layer can degrade (right arrow sequence).

In some embodiments, the degradation of the API layer can control the release of the API for a period of at least 3 days, at least 5 days, at least 1 week, at least 2 weeks, at least 3 weeks, at least 3.5 weeks, at least 4 weeks, at least 30 days, at least 4.5 weeks, at least 5 weeks, at least 6 weeks, at least 2 months, at least 3 months, at least 4 months, at least 6 months, at least 8 months, or at least 10 months, after implantation. In some embodiments, the degradation of the API layer can control the release of the API for a period of at most 2 years, at most 1 year, at most 10 months, at most 8 months, at most 6 months, at most 4 months, at most 3 months, at most 2 months, at most 6 weeks, at most 5 weeks, at most 4.5 weeks, at most 30 days, at most 4 weeks, at most 3.5 weeks, at most 3 weeks, at most 2 weeks, or at most 1 week, after implantation. In some embodiments, the degradation of the API layer can control the release of the API for a period of about 3 days to 10 months, 1 week to 6 months, 1-6 weeks, about 2-6 weeks, about 3-5 weeks, about 3.5-4.5 weeks, or about 4 weeks (about 30 days), after implantation. In some embodiments, the biodegradable polymer in the API layer can provide controlled and sustained release of the API over this period during which the cancer-facing side of the device is absorbed into the body. In some embodiments, the non-cancer-facing side (non-API layer) of the device, can help ensure that the drug delivery device maintains contact with the targeted tissue (e.g., tumor) during drug release and can help prevent release drug delivery device from the area of interest. This non-API layer can then completely degrade after the API layer has completely degraded and released the entirety of the API. FIG. 26 illustrates an exemplary flowchart of how drug delivery devices disclosed herein can attack live tumor cells in some embodiments. In some embodiments, a non-API layer can completely degrade at the same time or faster than the API layer.

Large animal (i.e., pigs) and human cadaver studies show that the drug delivery devices disclosed herein can be successfully deployed to the peritumoral pancreatic surface of the pancreas by a standard laparoscopic procedure. Specifically, two 30-day studies in porcine models were conducted to assess safety, toxicity, and biodistribution. Parameters included body weights, hematology, urinalyses, drug levels in the blood and at the implantation site, and histomorphologic evaluation of major organs. In both studies, the drug delivery device was designed to locally deliver paclitaxel over a 30 day period. In the first study, the drug delivery device was laparoscopically implanted onto the peritoneal surface to test feasibility and issue tolerance of paclitaxel. In the second study, the drug delivery device was placed directly onto the ventral surface of the healthy porcine pancreas in an open operation. This is shown in FIGS. 27A-27B. Blood samples for paclitaxel analysis were collected on Day 0 (prior to and post implantation), twice weekly thereafter, and on Day 31 (prior to necropsy), processed for plasma, stored frozen, and sent for paclitaxel level analysis. The animals were euthanized on Day 31, and a limited necropsy was performed. All frozen plasma and designated tissue samples were processed and analyzed for paclitaxel content by LC-MS according the appropriate laboratory methods and standard operating procedures at the test site. A protein precipitation extraction method was used for plasma and tissue samples, with homogenization of the tissue samples. For device testing, all samples were soaked 9:1 (v:w) of 0.5% formic acid in methanol and sonicated in an ice bath for 30 minutes. The solution was transferred into a new container on ice. The process was repeated two additional times. A final 9:1 v:w (rinse) was added and transferred to the final vial. Implant and tissue samples were paraffin-processed and stained with H&E for histomorphologic assessment. Light microscopy was used for characterization of the host response using standard nomenclature of pathology including type of inflammation, fibrosis, collagen deposition/content, and vascularity/vascular integration.

Figure 29:
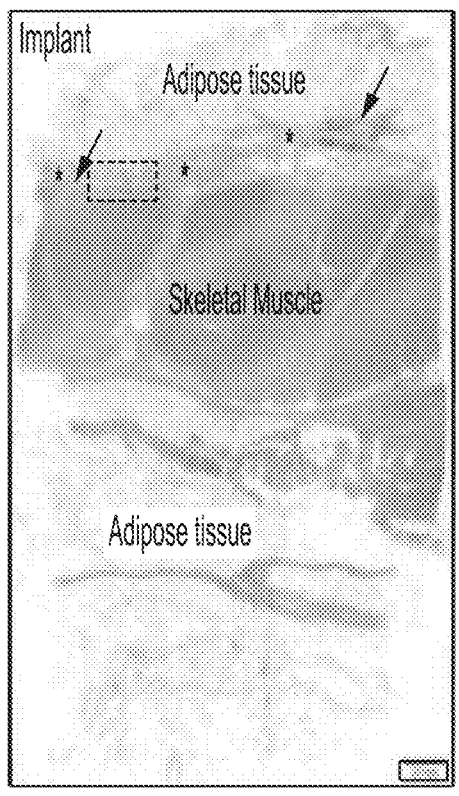
FIG. 29 illustrates the histology of the abdominal wall from the porcine studies in accordance with some embodiments disclosed herein. Abdominal wall underlying shows only mild hemorrhage (arrows) and necrosis in adipose tissue (asterisks).

The animals appeared healthy for the full 30 days in both studies, without showing debilitating effects usually associated with IV administration of chemotherapy (weight gain was expected in case of healthy pig not receiving chemo as shown in FIG. 28 while in case of chemo IV weight was expected to go down). After 30 days of paclitaxel release in vivo, the non-API backing layer was still present at the implant sites without signs of migration. The underlying tissue in the abdominal wall showed some visible redness, but histology showed minimal hemorrhage and necrosis as shown in FIG. 29. The underlying tissue in the pancreas showed some thin capsule and fibrosis but minimal effect on the surrounding structure as shown in FIG. 30. The drug was released and primarily accumulated beneath the drug delivery device at concentration up to 40 microM (as shown in FIG. 31). Serum paclitaxel levels were measured below quantitation limits throughout the 30 days of treatment, validating the ability of the drug delivery device to deliver the drug only at its intended site. As such, there does not appear to be any diffusion outside of the area of interest.

To validate the feasibility of minimally invasive surgical insertion, the drug delivery device disclosed herein was laparoscopically placed directly on the pancreas of three human cadavers. The drug delivery device was consistently and effectively placed during a minimally invasive surgery without substantial increase in procedure time. More specifically, the time up to pancreas visualization during the laparoscopic procedure took about 25 minutes and the amount of time for the drug delivery device placement and suturing on the pancreas took about 10-25 minutes, about 10-20 minutes, or about 15-20 minutes. As such, placing the drug delivery device at the target site only slightly increased the procedure time. The drug delivery device conformed fully to pancreatic tissue, allowing for close contact with the intended tissue for drug delivery, and can cover the areas of the pancreas where critical involvements of tumors with vasculature are commonly found.

Lastly, the drug delivery devices disclosed herein have been used in three patients for a Phase I Clinical Trial. The three patients were suffering from locally advanced pancreatic ductal adenocarcinoma (PDAC) and were treated with a drug delivery device in the shape of a circular patch containing a first layer of 1 g of PLGA 50:50, 90-105 mg paclitaxel, and 40-100 mg acetone and a second (backing layer) on a side of the first layer made up of 1 g PLGA 75:25 and 40-100 mg acetone.

Prior to implantation, the surgeons prepared each of the drug delivery devices by placing sutures at four evenly spaced locations around the edge of the second layer, approximate the four cardinal directions for the circular drug delivery device. The patch was placed via a trocar directly onto the pancreatic surface overlying the tumor using standard laparoscopic surgical equipment after a diagnostic laparoscopy confirmed the subjects were negative for visual metastatic disease. The implant procedure took between 18-32 minutes for all three patients treated to date. The device was oriented correctly on the pancreas and placed successfully in all cases with paclitaxel layer facing the pancreas. No adverse event or device malfunctions were reported during any of the procedures. Ease of preparation was rated as very easy for all procedures and placement was rated either very easy or not difficult.

Before implantation and at various time points after implantation, volumetric, transversal, and anterior/posterior measurements of the tumors were taken for each patient. Specifically, the transversal (T) measurement can be the length of the largest dimension of the tumor. The anterior/posterior (AP) dimension or diameter can be the length of the tumor orthogonal to the drug delivery device. In some embodiments, the anterior/posterior dimension or diameter can be the length of the tumor in the direction of drug release/delivery. In some embodiments, the anterior/posterior dimension can be the largest dimension of the tumor orthogonal to the drug delivery device. The transversal dimension can be measured manually by reader on the longest diameter tumor slice in CT software. The anterior-posterior diameter can be measured manually by reader on longest diameter tumor slice orthogonal to the drug delivery device in CT software. The volume of the tumor can be measured by lesion delineated on axial view by reader on each tumor slice calculated by 3D software.

In addition, the patients' blood can be tested for CA 19-9 using a standard lab test and for paclitaxel using a pharmacokinetic assay. Standard RECIST (Response Evaluation Criteria in Solid Tumors) measurements were used to determine clinical outcomes (e.g., partial response, remains unresectable, metastatic, primary stable/progress, stable disease, etc.).

All patients began modified FOLFIRINOX (oxaliplatin, Leucovorin, Fluorouracil, and Irinotecan) 21 days (±7 days) after device implantation. The third patient had their dose increased after the first cycle of treatment and the first patient also had radiotherapy approximately 7 months post device implantation to treat their tumor after systemic chemotherapy was completed.

This Phase I Clinical Trial demonstrated a local response in the initial cohort of patients, an excellent safety profile (e.g., well tolerated in all patients with no SAEs, no peritonitis, pancreatitis, infection, or hematologic toxicity as well as no detectable level of paclitaxel systemically), and minimal increase in operating room time for drug delivery device deployment (i.e., less than about 20 minutes).

Figures 35A, 35B:
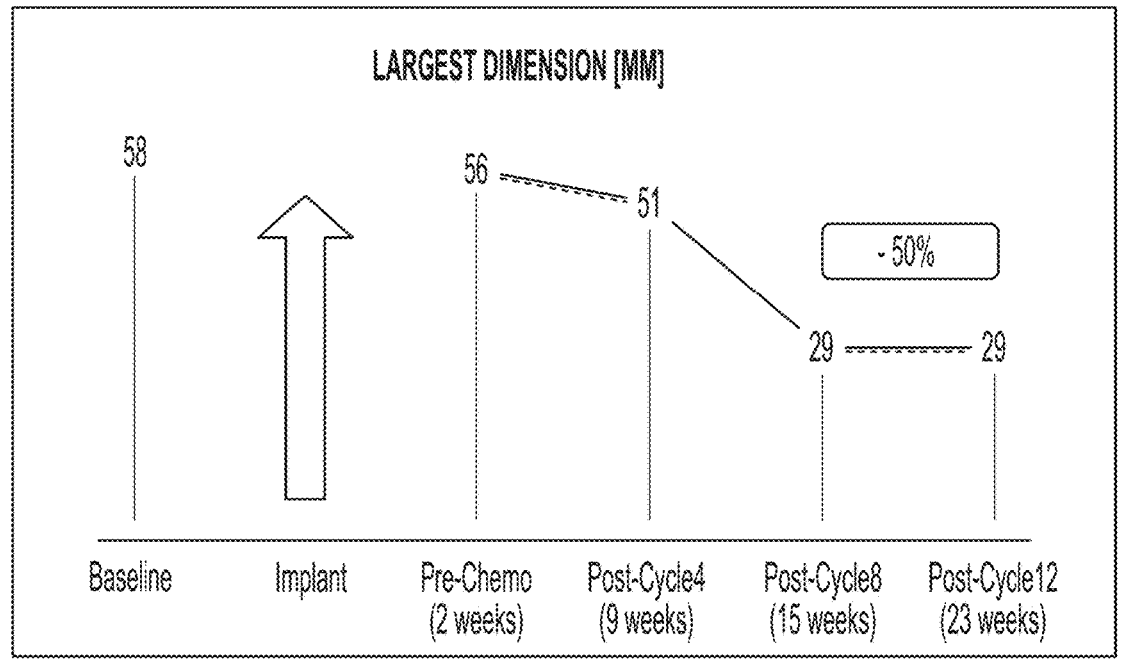
FIG. 35A illustrates a graph of the tumor's largest dimension in a first patient over time from a clinical trial of a drug delivery device in accordance with some embodiments disclosed herein.
FIG. 35B illustrates the tumor assessment from the first patient from a clinical trial of a drug delivery device in accordance with some embodiments disclosed herein.
Figure 36A:
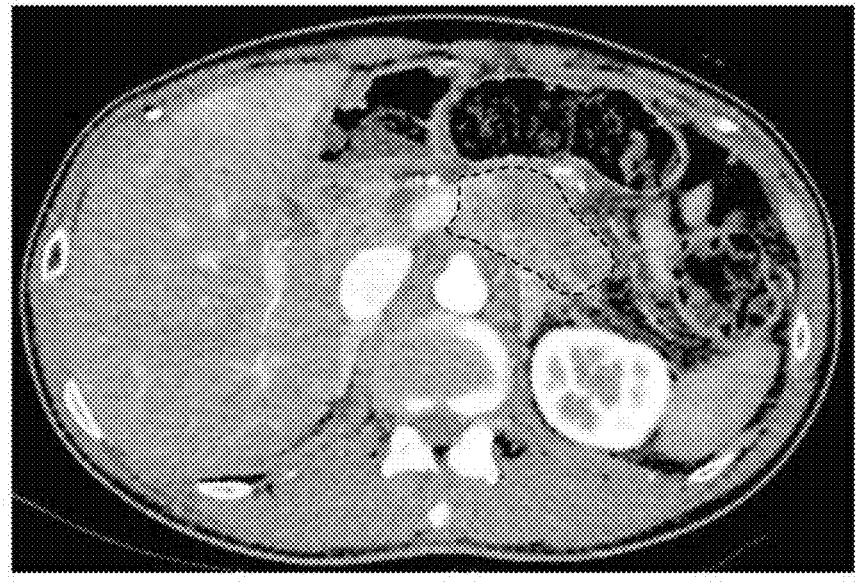
FIG. 36A illustrates a radiographical image from the tumor as dashed line of the first patient at baseline from a clinical trial of a drug delivery device in accordance with some embodiments disclosed herein.
Figure 36B:
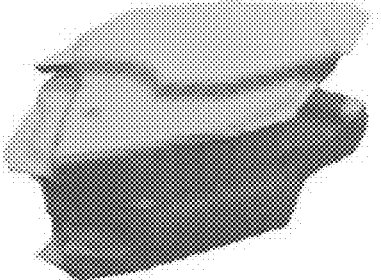
FIG. 36B illustrates a 3D rendering of the tumor of the first patient at baseline from a clinical trial of a drug delivery device in accordance with some embodiments disclosed herein.
Figure 37A:
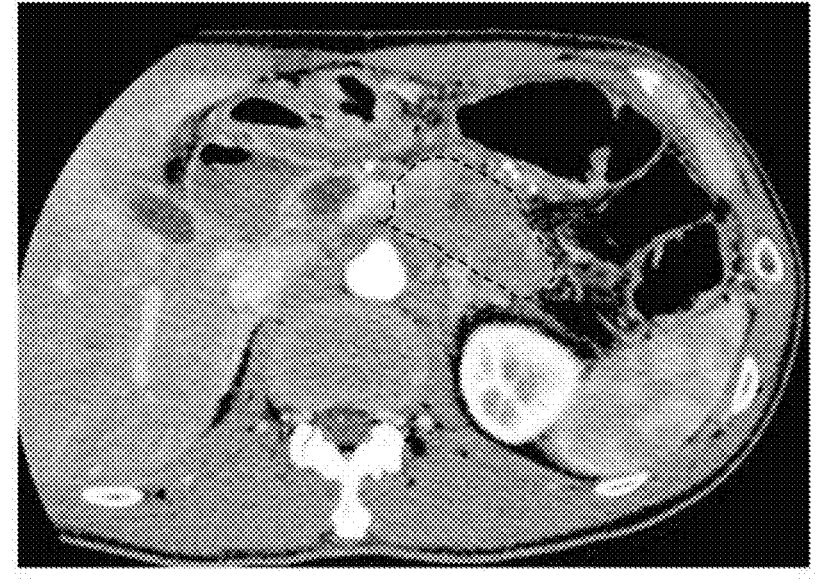
FIG. 37A illustrates a radiographical image from the tumor as dashed line of the first patient after 2 weeks post-implant pre-chemotherapy from a clinical trial of a drug delivery device in accordance with some embodiments disclosed herein.
Figure 37B:
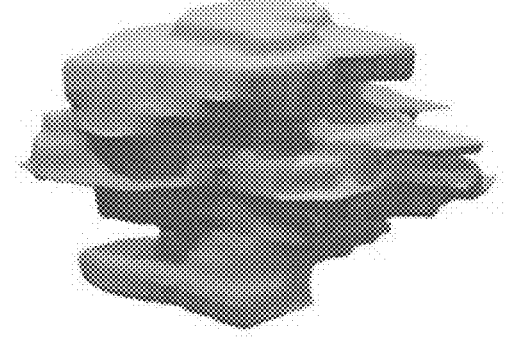
FIG. 37B illustrates a 3D rendering of the tumor of the first patient at 2 weeks post-implant pre-chemotherapy from a clinical trial of a drug delivery device in accordance with some embodiments disclosed herein.
Figure 38A:
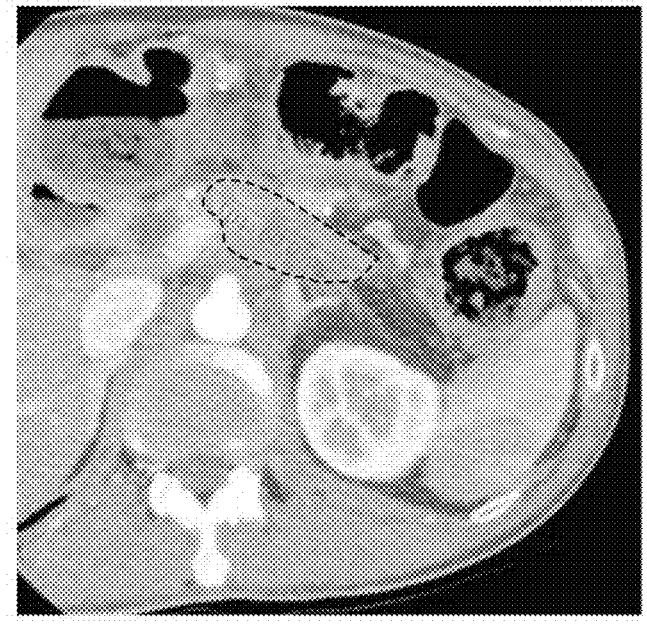
FIG. 38A illustrates a radiographical image from the tumor as dashed line of the first patient after 10 weeks post-implant pre cycle 5 of chemotherapy from a clinical trial of a drug delivery device in accordance with some embodiments disclosed herein.
Figure 38B:
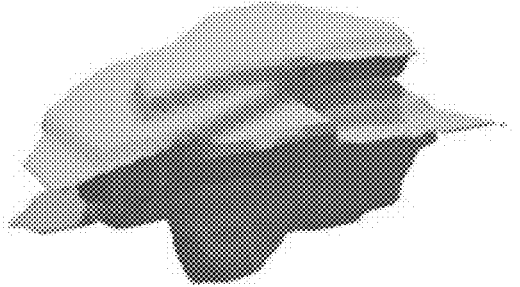
FIG. 38B illustrates a 3D rendering of the tumor of the first patient at 10 weeks post-implant pre cycle 5 of chemotherapy from a clinical trial of a drug delivery device in accordance with some embodiments disclosed herein.
Figure 39A:
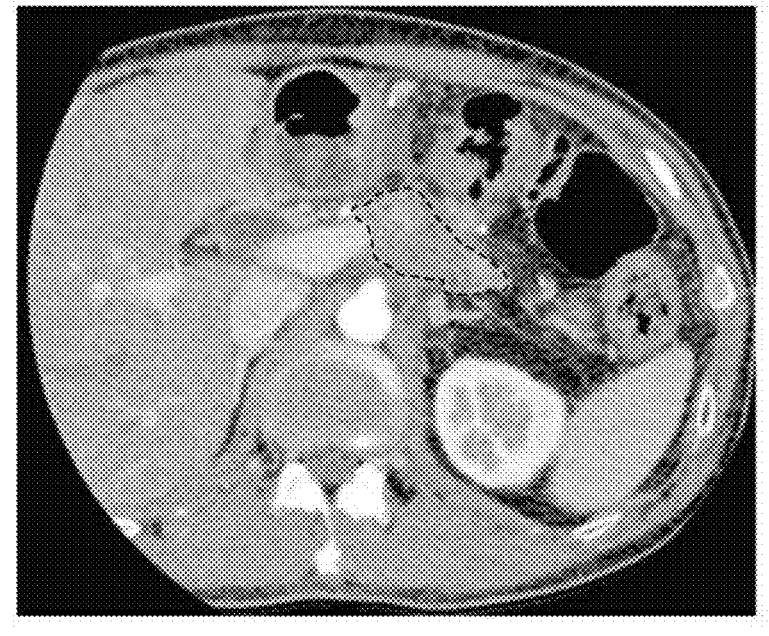
FIG. 39A illustrates a radiographical image from the tumor as dashed line of the first patient after 16 weeks post-implant pre cycle 9 of chemotherapy from a clinical trial of a drug delivery device in accordance with some embodiments disclosed herein.
Figure 39B:
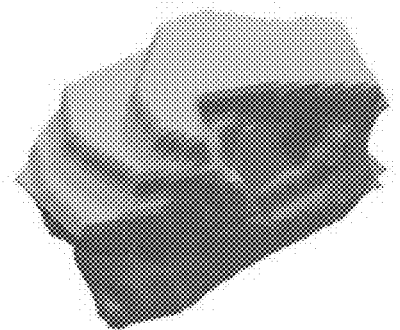
FIG. 39B illustrates a 3D rendering of the tumor of the first patient at 16 weeks post-implant pre cycle 9 of chemotherapy from a clinical trial of a drug delivery device in accordance with some embodiments disclosed herein.
Figure 40A:
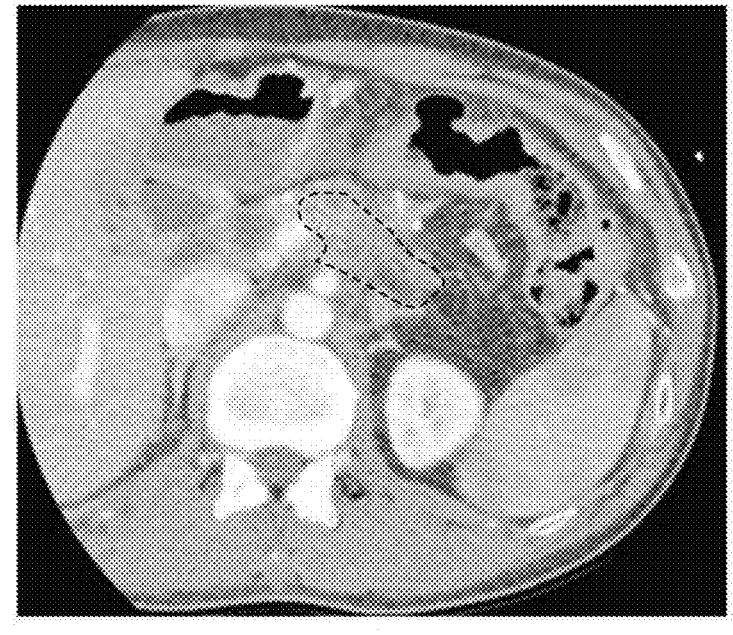
FIG. 40A illustrates a radiographical image from the tumor as dashed line of the first patient after 24 weeks post-implant pre cycle 12 of chemotherapy from a clinical trial of a drug delivery device in accordance with some embodiments disclosed herein.
Figure 40B:
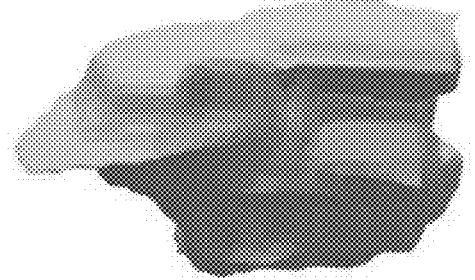
FIG. 40B illustrates a 3D rendering of the tumor of the first patient at 24 weeks post-implant pre cycle 12 of chemotherapy from a clinical trial of a drug delivery device in accordance with some embodiments disclosed herein.

The first patient had a locally advanced disease. The implantation procedure time took 25 minutes for the first patient and the clinical outcome was partial response, remains unresectable. FIG. 35A illustrates a graph of the tumor's largest dimension in the first patient over 23 weeks and FIG. 35B illustrates the data collected regarding tumor volume and size over 23 weeks. As shown by FIG. 35B, the volume of the first patient's tumor reduced by 11% in two weeks after implantation before systemic chemotherapy started and reduced by over 70% in 23 weeks after implantation. In addition, the largest dimension of the tumor saw a 50% decrease in 23 weeks after implantation and the anterior/posterior dimension of the tumor reduced by 27% in that same time period. FIGS. 36A-40B illustrate radiographical images of the tumor (as dashed line) of the first patient as well as 3D renderings of the tumor at baseline, 2 weeks post-implant pre-chemo, 10 weeks post-implant pre cycle 5, 16 weeks post-implant pre cycle 9, and 24 weeks post-implant pre cycle 12. The first patient's latest visit was after the 12 month mark and the clinical outcome was RECIST progressive disease.

Figures 41A, 41B:
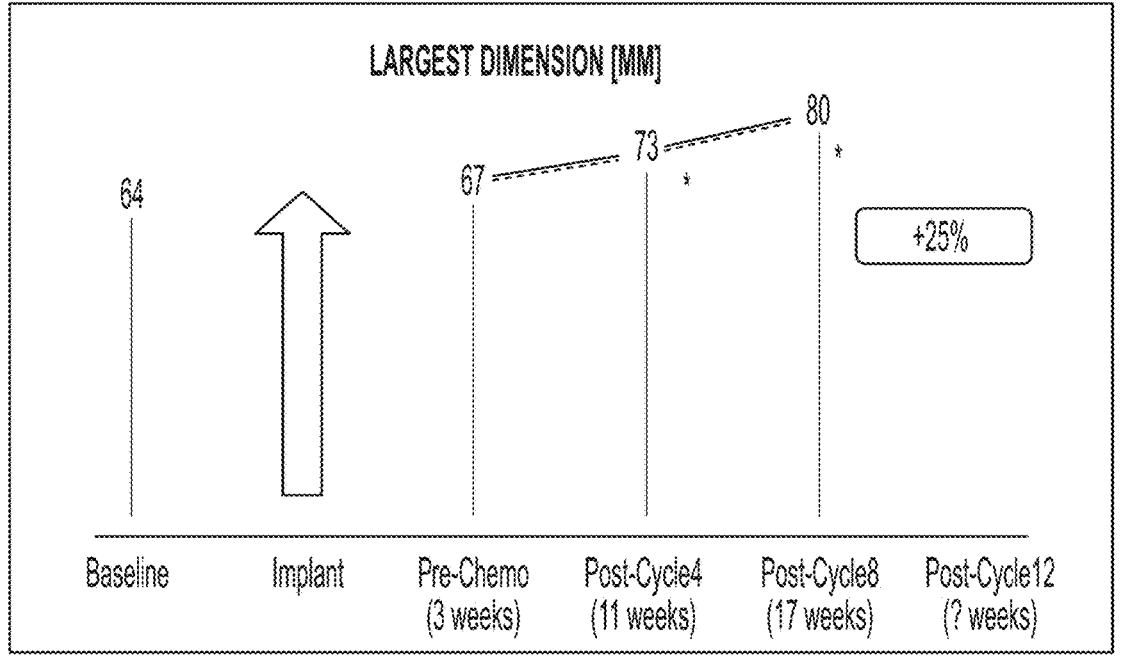
FIG. 41A illustrates a graph of the tumor's largest dimension in a second patient over time from a clinical trial of a drug delivery device in accordance with some embodiments disclosed herein.
FIG. 41B illustrates the tumor assessment from the second patient from a clinical trial of a drug delivery device in accordance with some embodiments disclosed herein.
Figure 42A:
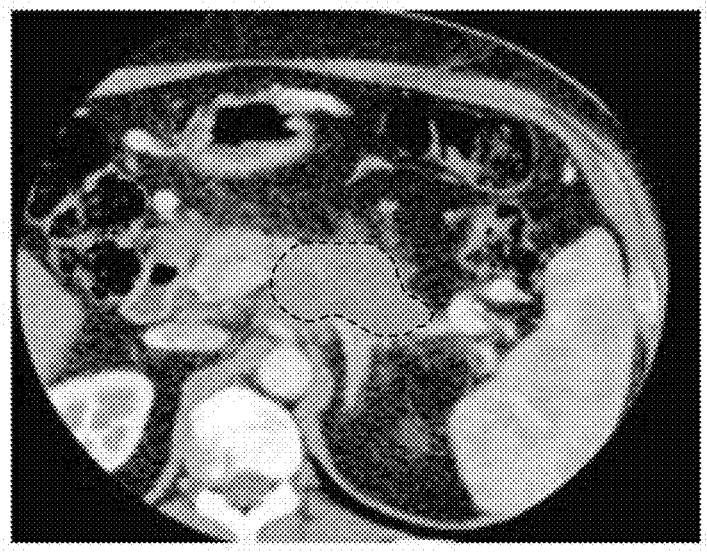
FIG. 42A illustrates a radiographical image from the tumor as dashed line of the second patient at baseline from a clinical trial of a drug delivery device in accordance with some embodiments disclosed herein.
Figure 42B:
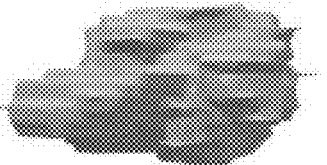
FIG. 42B illustrates a 3D rendering of the tumor of the second patient at baseline from a clinical trial of a drug delivery device in accordance with some embodiments disclosed herein.
Figure 43A:
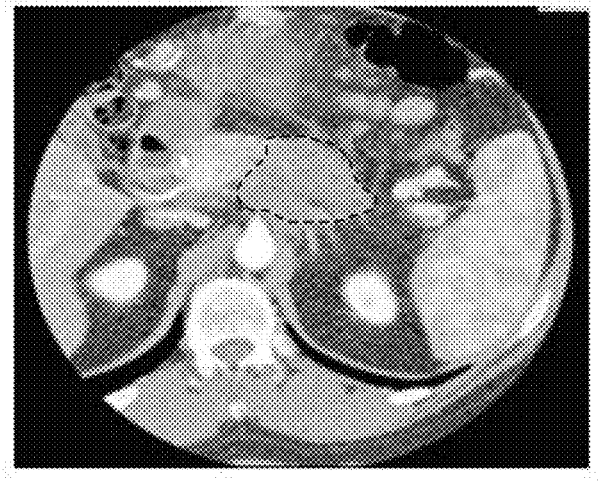
FIG. 43A illustrates a radiographical image from the tumor as dashed line of the second patient after 2 weeks post-implant from a clinical trial of a drug delivery device in accordance with some embodiments disclosed herein.
Figure 43B:
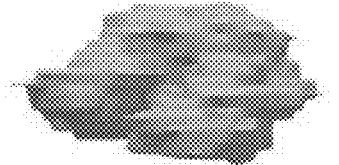
FIG. 43B illustrates a 3D rendering of the tumor of the second patient at 2 weeks post-implant from a clinical trial of a drug delivery device in accordance with some embodiments disclosed herein.
Figure 44A:
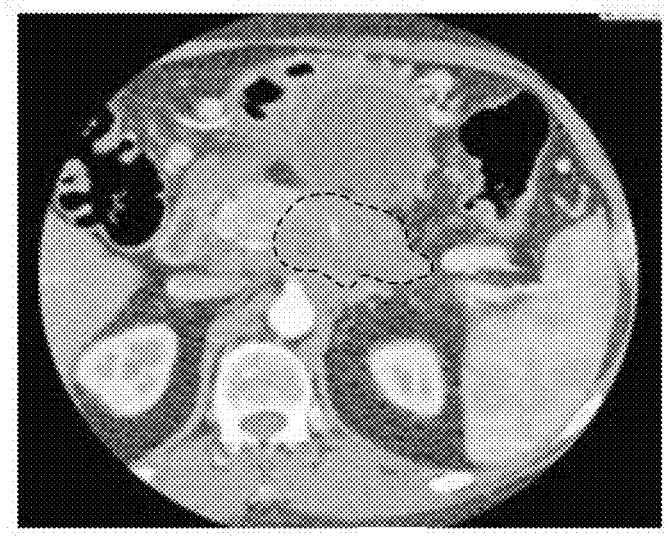
FIG. 44A illustrates a radiographical image from the tumor as dashed line of the second patient after 10 weeks post-implant pre cycle 5 of chemotherapy from a clinical trial of a drug delivery device in accordance with some embodiments disclosed herein.
Figure 44B:
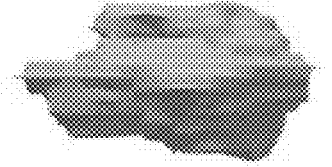
FIG. 44B illustrates a 3D rendering of the tumor of the second patient at 10 weeks post-implant pre cycle 5 of chemotherapy from a clinical trial of a drug delivery device in accordance with some embodiments disclosed herein.
Figure 45A:
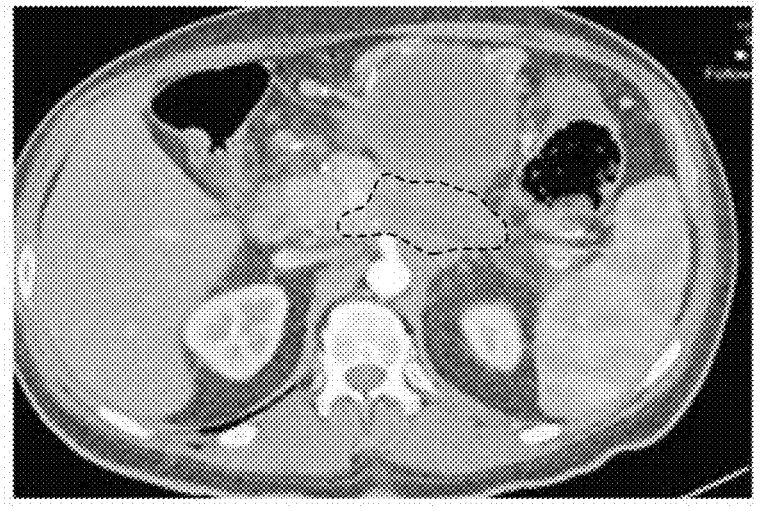
FIG. 45A illustrates a radiographical image from the tumor as dashed line of the second patient after 16 weeks post-implant pre cycle 9 of chemotherapy from a clinical trial of a drug delivery device in accordance with some embodiments disclosed herein.
Figure 45B:
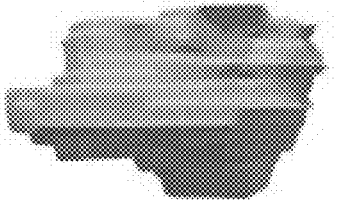
FIG. 45B illustrates a 3D rendering of the tumor of the second patient at 16 weeks post-implant pre cycle 9 of chemotherapy from a clinical trial of a drug delivery device in accordance with some embodiments disclosed herein.

The second patient had a locally advanced disease. The implantation procedure time took 18 minutes for the second patient and the clinical outcome was metastatic, primary stable/progressed. The second patient presented with a large tumor and distant metastasis was identified at the 3-month visit. It is possible that the subject already had metastatic disease at the time of presentation that had not been diagnosed. Despite the distant disease progression, the second patient still experienced a reduction in the anterior/posterior direction of the tumor and the tumor remained stable indicating that the subject received the benefits of local treatment. FIG. 41A illustrates a graph of the tumor's largest dimension in the second patient. The "*" in the graph equates to failed systemic chemo treatment and that the patient showed metastatic disease. FIG. 41B illustrates the data collected regarding tumor volume and size. As shown in FIG. 41B the length in the anterior/posterior direction of the tumor still decreased by 16%. FIGS. 42A-45B illustrate radiographical images of the tumor (as dashed lines) of the second patient as well as 3D renderings of the tumor at baseline, 2 weeks post-implant pre-chemo, 10 weeks post-implant pre cycle 5, and 16 weeks post-implant pre cycle 9. The second patient's latest visit was at the 6 month mark and the clinical outcome was RECIST metastatic, primary stable/progressed.

Figures 46A, 46B:
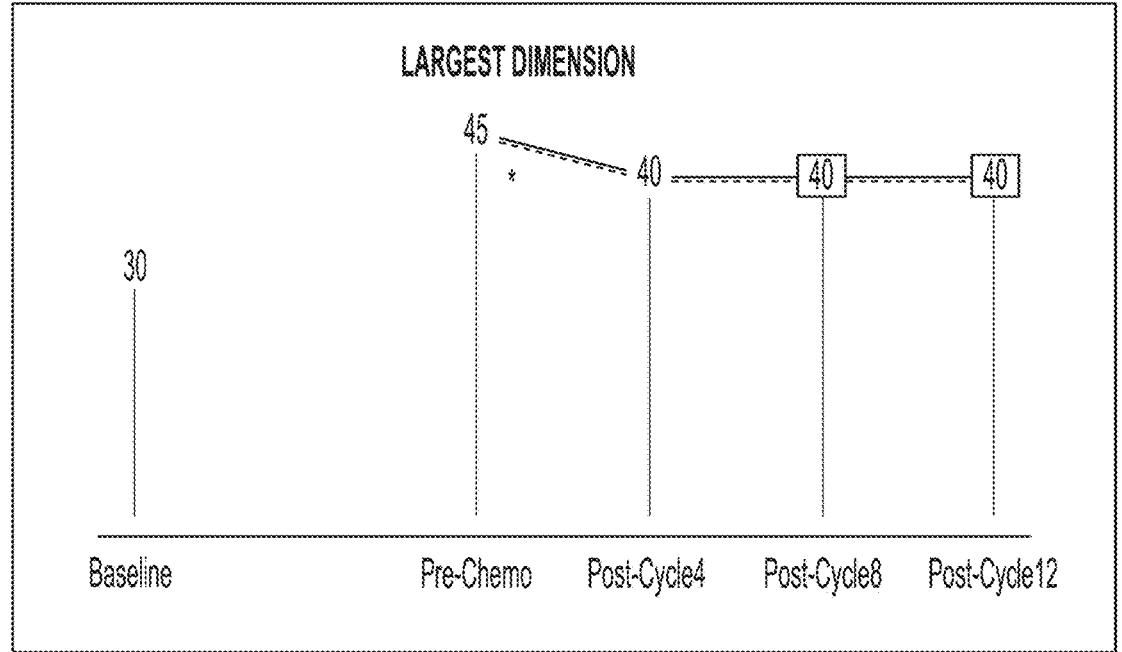
FIG. 46A illustrates a graph of the tumor's largest dimension in a third patient over time from a clinical trial of a drug delivery device in accordance with some embodiments disclosed herein.
FIG. 46B illustrates the tumor assessment from the third patient from a clinical trial of a drug delivery device in accordance with some embodiments disclosed herein.
Figure 47A:
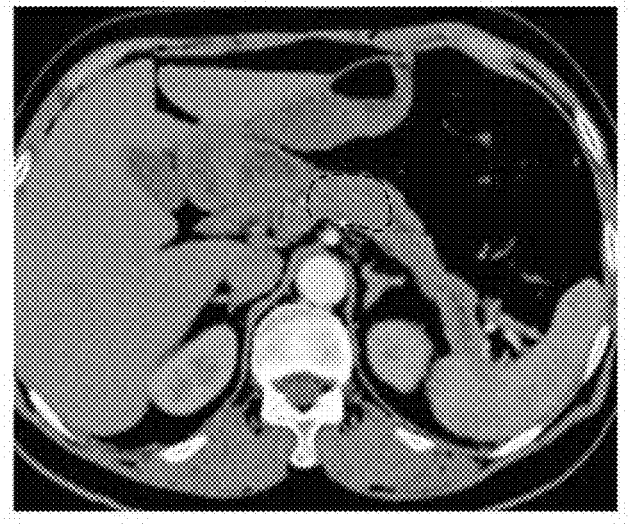
FIG. 47A illustrates a radiographical image from the tumor as dashed line of the third patient at baseline from a clinical trial of a drug delivery device in accordance with some embodiments disclosed herein.
Figure 47B:
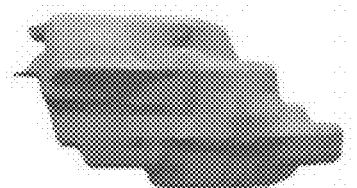
FIG. 47B illustrates a 3D rendering of the tumor of the third patient at baseline from a clinical trial of a drug delivery device in accordance with some embodiments disclosed herein.
Figure 48A:
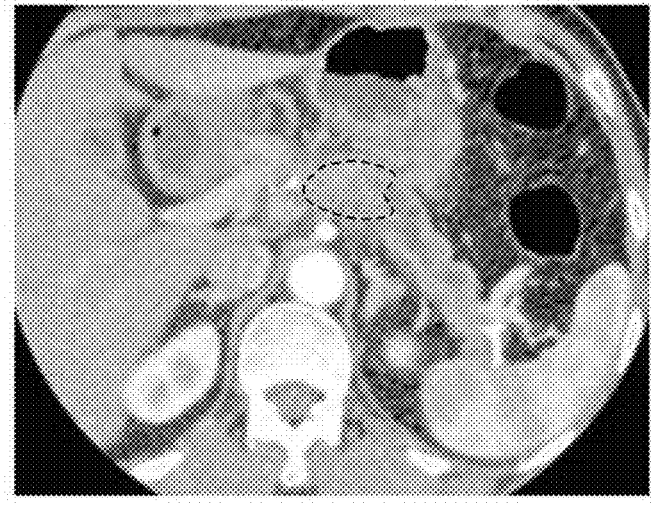
FIG. 48A illustrates a radiographical image from the tumor as dashed line of the third patient after 2 weeks post-implant from a clinical trial of a drug delivery device in accordance with some embodiments disclosed herein.
Figure 48B:
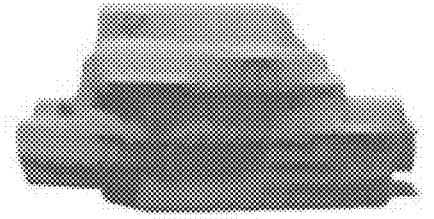
FIG. 48B illustrates a 3D rendering of the tumor of the third patient at 2 weeks post-implant from a clinical trial of a drug delivery device in accordance with some embodiments disclosed herein.
Figures 49A, 49B:
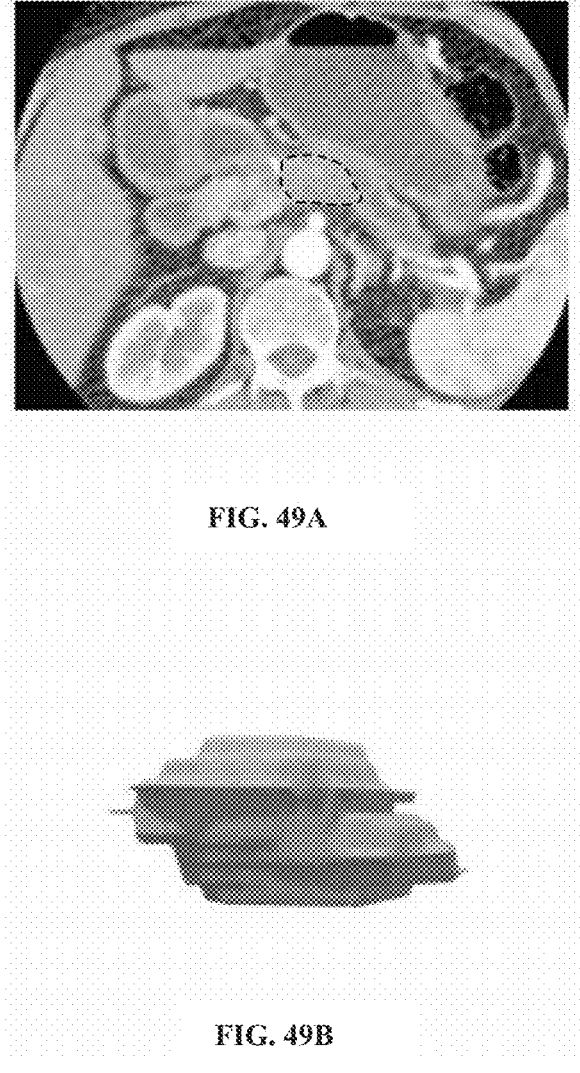
FIG. 49A illustrates a radiographical image from the tumor as dashed line of the third patient after 10 weeks post-implant pre cycle 5 of chemotherapy from a clinical trial of a drug delivery device in accordance with some embodiments disclosed herein.
FIG. 49B illustrates a 3D rendering of the tumor of the third patient at 10 weeks post-implant pre cycle 5 of chemotherapy from a clinical trial of a drug delivery device in accordance with some embodiments disclosed herein.
Figure 50A:
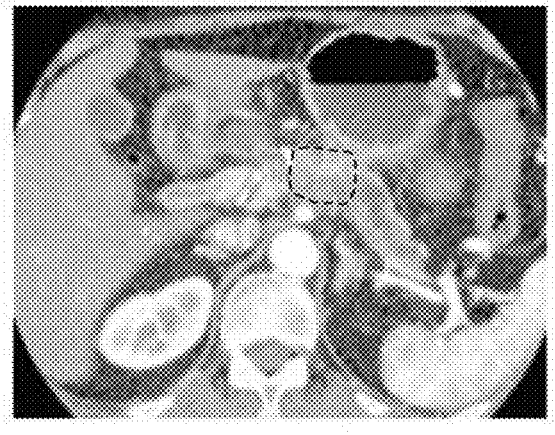
FIG. 50A illustrates a radiographical image from the tumor as dashed line of the third patient after 16 weeks post-implant pre cycle 9 of chemotherapy from a clinical trial of a drug delivery device in accordance with some embodiments disclosed herein.
Figure 50B:
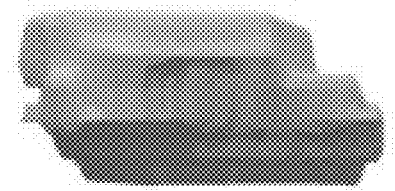
FIG. 50B illustrates a 3D rendering of the tumor of the third patient at 16 weeks post-implant pre cycle 9 of chemotherapy from a clinical trial of a drug delivery device in accordance with some embodiments disclosed herein.
Figure 51A:
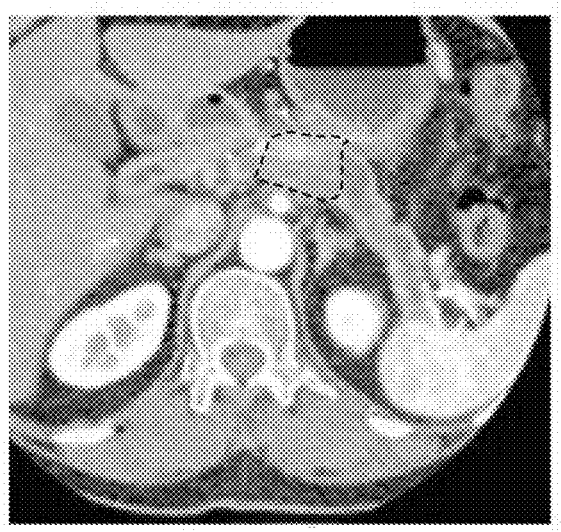
FIG. 51A illustrates a radiographical image from the tumor as dashed line of the third patient after 24 weeks post-implant pre cycle 12 of chemotherapy from a clinical trial of a drug delivery device in accordance with some embodiments disclosed herein.
Figure 51B:
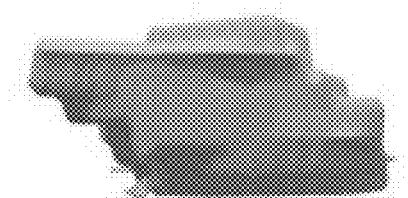
FIG. 51B illustrates a 3D rendering of the tumor of the third patient at 24 weeks post-implant pre cycle 12 of chemotherapy from a clinical trial of a drug delivery device in accordance with some embodiments disclosed herein.

The third patient also had locally advanced disease. The implantation procedure time took 32 minutes for the third patient and the clinical outcome was stable disease. FIG. 46A illustrates a graph of the tumor's largest dimension in the third patient and FIG. 46B illustrates the data collected regarding tumor volume and size. The "*" shown in FIG. 46A is to point out that the analysis for transversal dimension used week 2 data due to baseline uncertainty. FIGS. 47A-51B illustrate radiographical images of the tumor (as dashed line) of the third patient as well as 3D renderings of the tumor at baseline, 2 weeks post-implant pre-chemo, 10 weeks post-implant pre cycle 5, 16 weeks post-implant pre cycle 9, and 24 weeks post-implant pre cycle 12. The third patient's latest visit was at the 12 month mark and the clinical outcome was RECIST progressive disease (metastatic).

Figure 52:
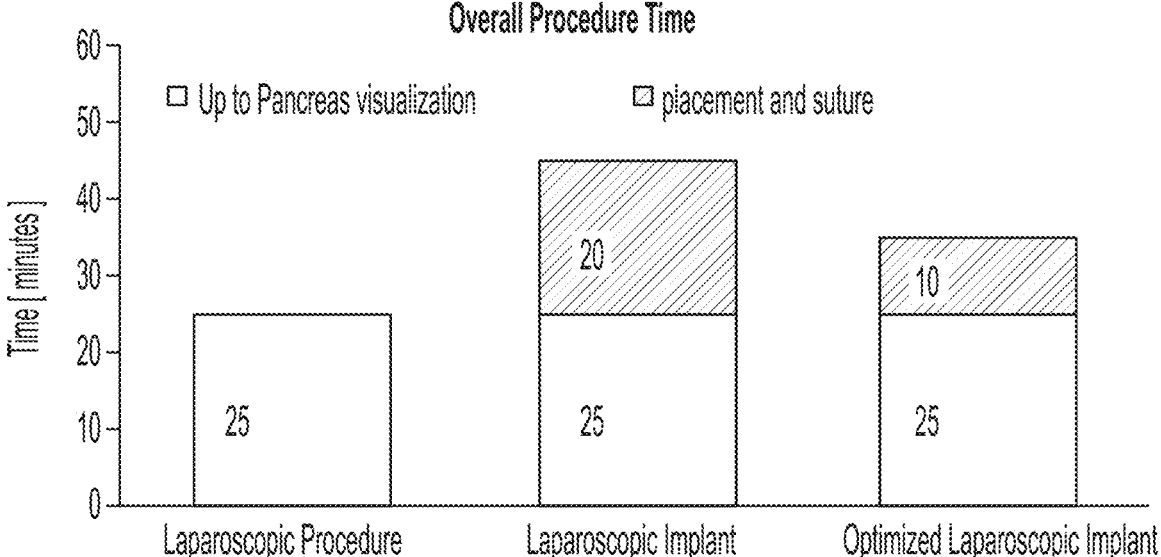
FIG. 52 illustrates the overall procedure time for implanting a drug delivery device in accordance with some embodiments disclosed herein.

From the three patients in the clinical trial, the drug delivery device was easily integrated into laparoscopic procedures. The device was successfully implanted using standard laparoscopic setup, there was minor increase in procedure time, and there is opportunity to further reduce time with robotic procedure and/or optimization as shown in FIG. 52.

Figure 53:
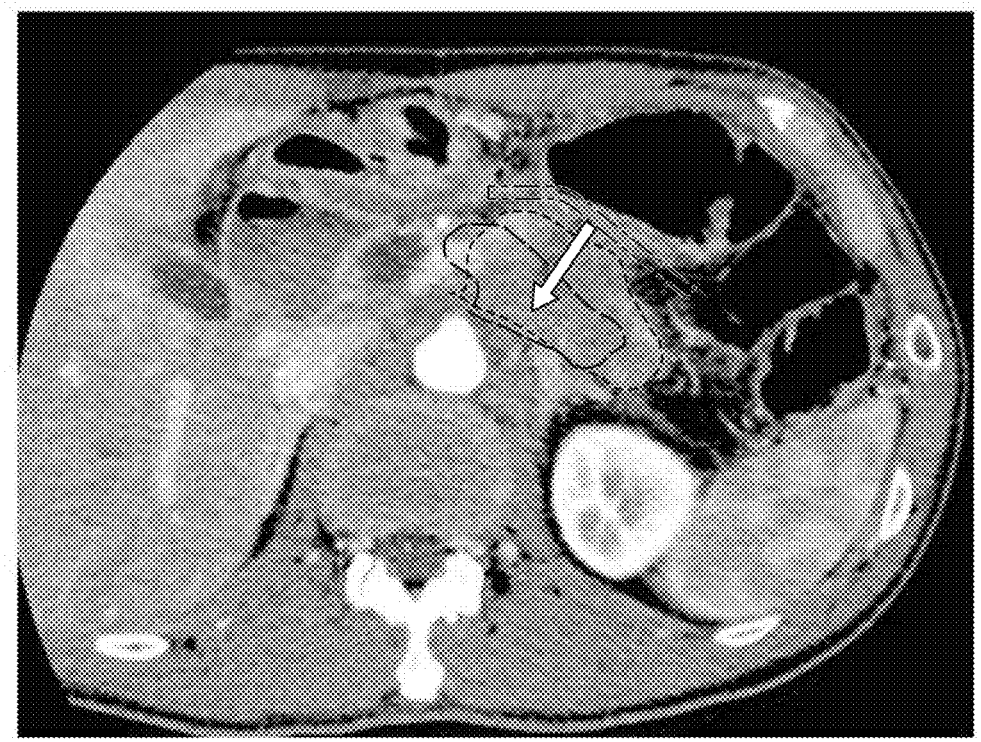
FIG. 53 illustrates the reduction in tumor size of the first patient from a clinical trial of a drug delivery device in accordance with some embodiments disclosed herein.

FIG. 53 illustrates the reduction in tumor size of the first patient from the clinical trial. As stated above, the first patient's tumor reduced from baseline greater than 70%. In addition, there was a higher response in antero-posterior direction (in the direction of drug release) measured in the axial plane with significant bulging effect reduction of the pancreatic lesion at pre-cycle 5 and confirmed on next visits.

Figure 54:
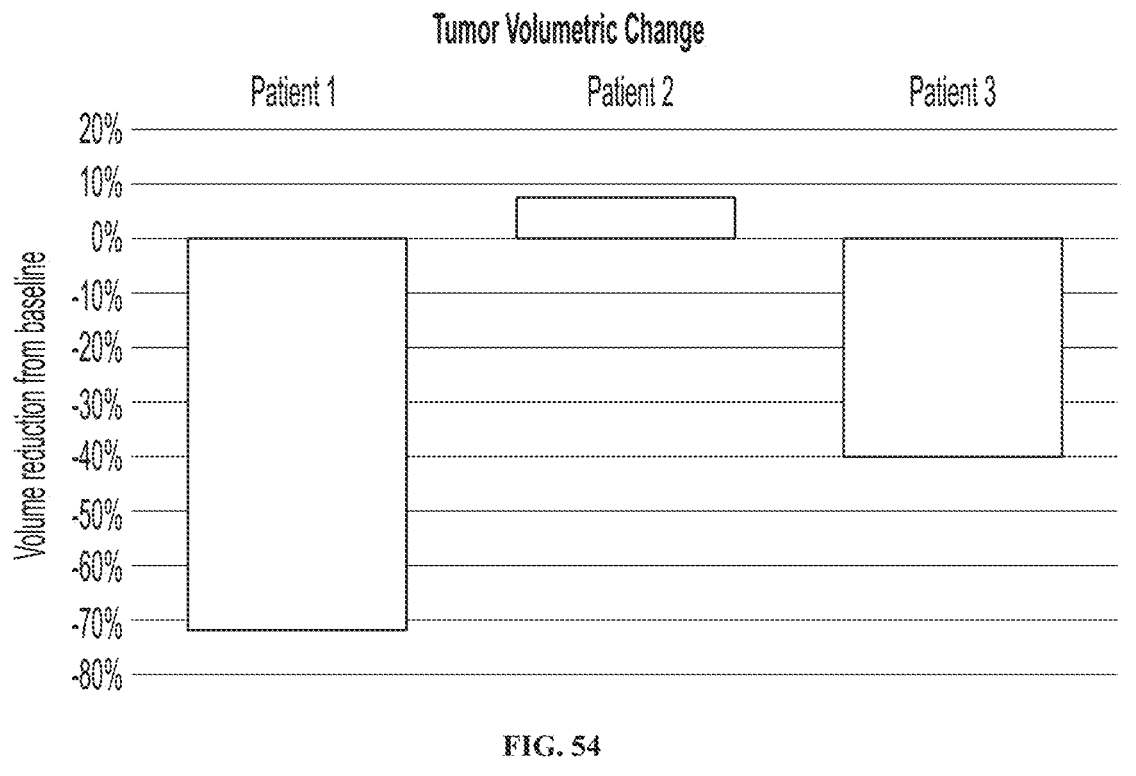

FIG. 54 illustrates tumor volumetric change from baseline for the three patients in the clinical trial. The drastic tumor volume reduction for the first patient (~70%) and the third patient (~40%) was confirmed at the latest scans. In addition, the second patient who failed systemic treatment and progressed to metastatic showed minimal local volumetric change. As such, the drug devices disclosed herein can stabilize and/or reduce tumor size (e.g., volume, transverse dimension, or anterior/posterior dimension).

Figure 55:
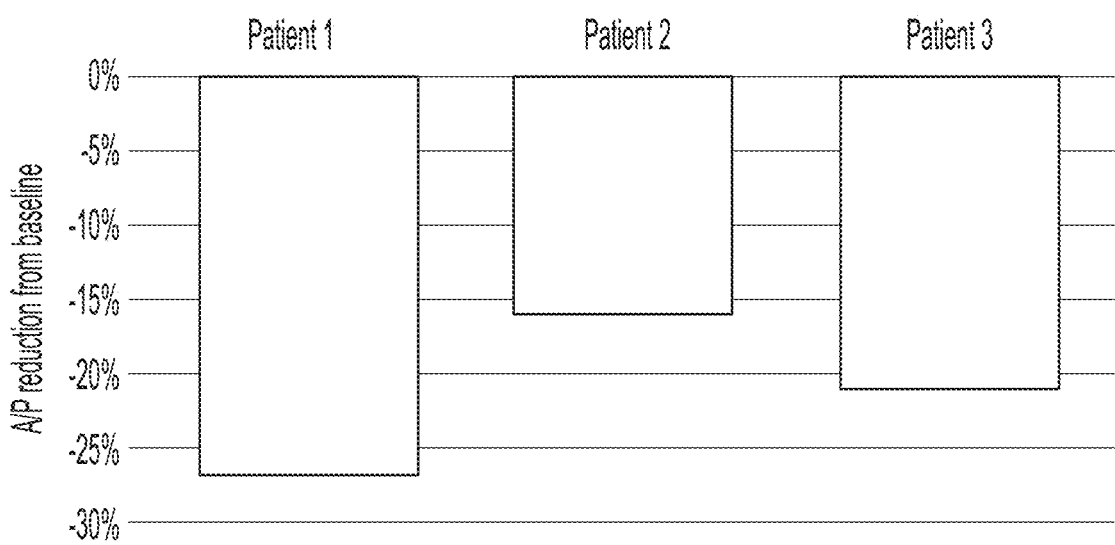
FIG. 55 illustrates tumor anterior/posterior reduction of the three patients from a clinical trial of a drug delivery device in accordance with some embodiments disclosed herein.

FIG. 55 illustrates tumor anterior/posterior reduction of the three patients. This strong reduction response in anterior/posterior diameter helps illustrate the drug delivery device's ability to unidirectionally release the API onto the tumor. This can also be shown in FIG. 53 with the implant shown as the dash-dot line, the tumor 2 weeks post-implant shown by the short dashed line, and the tumor 24 weeks post-implant shown in the long dashed line. As you can see by the arrow in FIG. 53, the tumor shrunk in the anterior/posterior direction (i.e., the direction orthogonal to the drug delivery device).

Figures 56A, 56B:
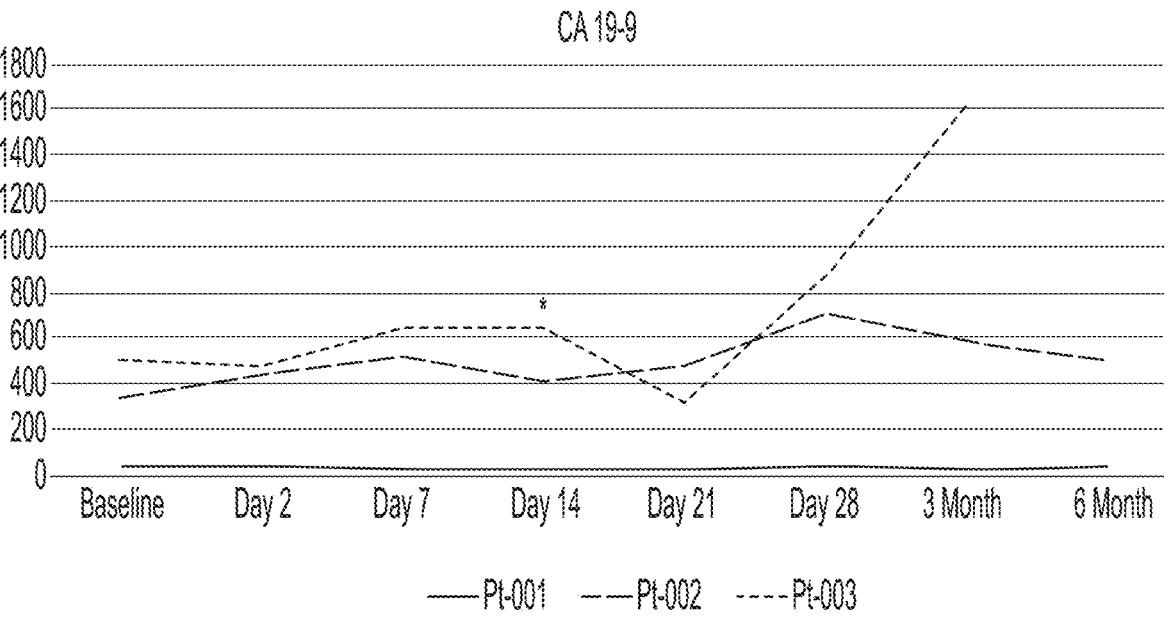
FIG. 56A illustrates a chart of the amount of CA 19-9 in the three patients' blood from a clinical trial of a drug delivery device in accordance with some embodiments disclosed herein.
FIG. 56B illustrates a table of the amount of CA 19-9 in the three patients' blood from a clinical trial of a drug delivery device in accordance with some embodiments disclosed herein.

FIGS. 56A-B illustrate the amount of CA 19-9 in the three patients' blood from the clinical trial over time. As shown in the figures, the first and third patients experienced a drop from baseline to day 21 of 28-37%. The second patient had metastatic disease but did show a slight reduction from day 7 to day 14 of 21%. The "*" in FIG. 56A shows that day 14 data for patient three was the same as day 7 for continuity.

Furthermore, no SAEs were reported in the 28-day safety window and beyond in any patients. There was no evidence of pancreatitis, peritonitis, or infection. There was no detectable paclitaxel in peripheral blood sampling in any patients. For example, the following modified ITT Population Table 1 illustrates that none of the patients from the clinical trial had any detectable paclitaxel in peripheral blood sampling:

TABLE 1

| | Patient 3 (N = 1) 33.3% | Patients 1 and 2 (N = 2) 66.7% | All Patients (N = 3) 100.0% |
|---|---|---|---|
| Screening/Baseline | | | |
| <40.0 Procedure | 100% (1/1) | 100% (2/2) | 100% (3/3) |
| <40.0 Day 2 | 100% (1/1) | 100% (2/2) | 100% (3/3) |
| <40.0 Day 7 | 100% (1/1) | 100% (2/2) | 100% (3/3) |
| <40.0 Day 14 | 100% (1/1) | 100% (2/2) | 100% (3/3) |
| <40.0 Day 21 | | 100% (2/2) | 66.7% (2/3) |
| <40.0 Day 28 | | 100% (2/2) | 66.7% (2/3) |
| <40.0 3 Months | 100% (1/1) | 100% (2/2) | 100% (3/3) |
| <40.0 | | 100% (2/2) | 66.7% (2/3) |

The lower limit of detection for the pharmacokinetic assay was 40 ng/mL. Results of undetectable indicate that paclitaxel was less than 40 ng/mL for every time point for every patient. The percentages refer to how many of the patients had undetectable paclitaxel in peripheral blood sampling. For example, in the third column, 100% refers to both patients 2 and 3 having no detectable paclitaxel in peripheral blood sampling of a patent. The 66.7% in the final column was because there was not a measurement for patient 1 for the given timepoint. As shown in the Table above, throughout the whole clinical trial testing, paclitaxel was not detectable in peripheral blood sampling for any of the patients.

The following modified ITT Population Table 2 illustrates the overall response rate for the three patients:

TABLE 2

| | Patient 3 (N = 1) 33.3% | Patients 1 and 2 (N = 2) 66.7% | All Patients (N = 3) 100.0% |
|---|---|---|---|
| Best Overall Response Rate | | | |
| Partial Response (PR) | 0.0% (0/1) | 50% (1/2) | 33.3% (1/3) |
| Stable Disease (SD) | 100% (1/1) | 50% (1/2) | 66.7% (2/3) |
| Overall Response Rate | | | |
| N | 0 | 1 | 1 |
| Rate | 0 (%) | 50 (%) | 33.3 (%) |
| 95% Confidence Interval | 0 (%), 97.5 (%) | 1.3 (%), 98.7 (%) | 0.8 (%), 90.6 (%) |

The best overall response rate is timepoint agnostic and can refer to the best response to treatment for each patient per standard RECIST measurements during the course of the clinical trial. For example, the first patient's best response was a stable disease response and the same was true for one of the second and third patients. The other of the second and third patient's best response to the treatment was partial response. The overall response rate removes the stable disease response and shows that only one of the patient's had a response being a partial response.

In addition, there was no delay in initiation of planned systemic therapy. As such, the drug delivery devices disclosed herein can behave as predicted in preclinical experiments and encourage local disease control in advanced cohort.

The drug delivery devices disclosed herein can stabilize and/or reduce the size of a tumor after implantation on a tumor. Specifically, the drug delivery devices disclosed herein can reduce the volume of a tumor by at least 10%, at least 20%, at least 30%, at least 40%, at least 50%, at least 60%, or at least 70% (with 100% reduction being the tumor disappearing) after implantation. The drug delivery devices disclosed herein can reduce the largest dimension of a tumor by at least 5%, at least 10%, at least 25%, at least 40%, or at least 50% after implantation. The drug delivery devices disclosed herein can reduce the anterior/posterior dimension of the tumor (i.e., orthogonal dimension from drug delivery device) by at least 10%, at least 15%, at least 20%, or at least 25% after implantation. In some embodiments, the change in tumor volume, tumor largest dimension, and/or tumor anterior/posterior dimension can be within ±10% or ±5% after implantation of the drug delivery device. In some embodiments, the reduction in size of the tumor, the reduction in tumor volume, the reduction in the largest dimension of the tumor, and/or the reduction of the anterior/posterior diameter orthogonal to the drug delivery device can be after the drug delivery device has completely dissolved in the patient, after the drug delivery device has partially dissolved in the patient, and/or after a portion of the drug delivery device (e.g., the API layer) has completely dissolved in the patient.

In some embodiments, the drug delivery devices disclosed herein can reduce the size of the cancerous tissue (e.g., tumor) in a patient. In some embodiments, a size of the tumor is reduced after 1 day, after 2 days, after 5 days, after 1 week, after 2 weeks, after 3 weeks, after 4 weeks, after 6 weeks, after 8 weeks, after 9 weeks, after 10 weeks, after 11 weeks, after 12 weeks, after 14 weeks, after 15 weeks, after 16 weeks, after 17 weeks, after 18 weeks, after 20 weeks, after 22 weeks, after 23 weeks, or after 24 weeks from implantation of the drug delivery device. In some embodiments, a volume of a tumor is reduced after 1 day, after 2 days, after 5 days, after 1 week, after 2 weeks, after 3 weeks, after 4 weeks, after 6 weeks, after 8 weeks, after 9 weeks, after 10 weeks, after 11 weeks, after 12 weeks, after 14 weeks, after 15 weeks, after 16 weeks, after 17 weeks, after 18 weeks, after 20 weeks, after 22 weeks, after 23 weeks, or after 24 weeks from implantation of the drug delivery device. In some embodiments, a largest dimension of the tumor is reduced after 1 day, after 2 days, after 5 days, after 1 week, after 2 weeks, after 3 weeks, after 4 weeks, after 6 weeks, after 8 weeks, after 9 weeks, after 10 weeks, after 11 weeks, after 12 weeks, after 14 weeks, after 15 weeks, after 16 weeks, after 17 weeks, after 18 weeks, after 20 weeks, after 22 weeks, after 23 weeks, or after 24 weeks from implantation of the drug delivery device. In some embodiments, the anterior/posterior diameter orthogonal to the drug delivery device is reduced after 1 day, after 2 days, after 5 days, after 1 week, after 2 weeks, after 3 weeks, after 4 weeks, after 6 weeks, after 8 weeks, after 9 weeks, after 10 weeks, after 11 weeks, after 12 weeks, after 14 weeks, after 15 weeks, after 16 weeks, after 17 weeks, after 18 weeks, after 20 weeks, after 22 weeks, after 23 weeks, or after 24 weeks from implantation of the drug delivery device. In some embodiments, the stabilization and/or reduction in size of the tumor, the stabilization and/or reduction in tumor volume, the stabilization and/or reduction in the largest dimension of the tumor, and/or the reduction of the anterior/posterior diameter orthogonal to the drug delivery device can be after the drug delivery device has completely dissolved in the patient, after the drug delivery device has partially dissolved in the patient, and/or after a portion of the drug delivery device (e.g., the API layer) has completely dissolved in the patient.

In some embodiments, a size (e.g., volume, transverse dimension, anterior/posterior dimension, etc.) of the tumor is stabilized and/or reduced after implantation of the drug delivery device without systemic chemotherapy. In some embodiments, the volume of the tumor is reduced by at least about 1%, at least about 2%, at least about 5%, at least about 7%, at least about 8%, at least about 9%, at least about 10%, at least about 11%, at least about 15%, at least about 20%, at least about 25%, at least about 30%, at least about 34%, at least about 35%, at least about 40%, at least about 45%, at least about 50%, at least about 55%, at least about 59%, at least about 60%, at least about 65%, at least about 68%, at least about 70%, at least about 72%, at least about 75%, at least about 80% after implantation of the drug delivery device. In some embodiments, the volume of the tumor is reduced by at most about 100%, at most about 95%, at most about 90%, at most about 85%, at most about 80%, at most about 75%, at most about 70%, at most about 65%, at most about 60%, at most about 55%, at most about 50%, at most about 40%, at most about 35%, at most about 30%, or at most about 25% after implantation of the drug delivery device. In some embodiments, the change in tumor volume can be within ±25%, ±20%, ±15%, ±10%, ±5%, ±2%, or ±1% after implantation of the drug delivery device. In some embodiments, the stabilization and/or reduction in tumor volume in this paragraph can be after the drug delivery device has completely dissolved in the patient, after the drug delivery device has partially dissolved in the patient, and/or after a portion of the drug delivery device (e.g., the API layer) has completely dissolved in the patient. In some embodiments, the volumes of the tumor in this paragraph are stabilized and/or reduced after implantation of the drug delivery device without systemic chemotherapy. In some embodiments, the volumes of the tumor in this paragraph are stabilized and/or reduced after implantation of the drug delivery device with systemic chemotherapy.

In some embodiments, the volume of the tumor is reduced by at least about 1%, at least about 2%, at least about 5%, at least about 7%, at least about 8%, at least about 9%, at least about 10%, at least about 11%, or at least about 15% two weeks after implantation of the drug delivery device. In some embodiments, the volume of the tumor is reduced by about 1-20% or about 5-15% two weeks after implantation of the drug delivery device. In some embodiments, the volume of the tumor is reduced by at least about 25%, at least about 30%, at least about 35%, at least about 40%, at least about 45%, at least about 50%, at least about 55%, at least about 59%, at least about 60%, or at least about 65% 9 weeks after implantation of the drug delivery device. In some embodiments, the volume of the tumor is reduced by at least about 15%, at least about 20%, at least about 25%, at least about 30%, at least about 34%, at least about 35%, or at least about 40% 11 weeks after implantation of the drug delivery device. In some embodiments, the volume of the tumor is reduced by at least about 45%, at least about 50%, at least about 55%, at least about 60%, at least about 65%, at least about 68%, at least about 70%, or at least about 75% 15 weeks after implantation of the drug delivery device. In some embodiments, the volume of the tumor is reduced by at least about 20%, at least about 25%, at least about 30%, at least about 35%, at least about 40%, or at least about 45% 16 weeks after implantation of the drug delivery device. In some embodiments, the volume of the tumor is reduced by at least about 55%, at least about 60%, at least about 65%, at least about 70%, at least about 72%, at least about 75%, or at least about 80% 23 weeks after implantation of the drug delivery device. In some embodiments, the volume of the tumor is reduced by at least about 20%, at least about 25%, at least about 30%, at least about 34%, at least about 35%, at least about 40%, or at least about 45% 24 weeks after implantation of the drug delivery device. In some embodiments, the reduction in tumor volume in this paragraph can be after the drug delivery device has completely dissolved in the patient, after the drug delivery device has partially dissolved in the patient, and/or after a portion of the drug delivery device (e.g., the API layer) has completely dissolved in the patient. In some embodiments, the volumes of the tumor in this paragraph are reduced after implantation of the drug delivery device without systemic chemotherapy. In some embodiments, the volumes of the tumor in this paragraph are reduced after implantation of the drug delivery device with systemic chemotherapy.

In some embodiments, a largest dimension of the tumor is reduced by at least about 1%, at least about 2%, at least about 3%, at least about 4%, at least about 5%, at least about 8%, at least about 10%, at least about 11%, at least about 12%, at least about 15%, at least about 20%, at least about 25%, at least about 30%, at least about 35%, at least about 40%, at least about 45%, at least about 50%, or at least about 55% after implantation of the drug delivery device. In some embodiments, the largest dimension of the tumor is reduced by at most 100%, at most 95%, at most 90%, at most 85%, at most 80%, at most 75%, at most 70%, at most 65%, at most 60%, at most 55%, at most 50%, at most 40%, at most 30%, or at most 25% after implantation of the drug delivery device. In some embodiments, the change in largest dimension of the tumor can be within ±25%, ±20%, ±15%, ±10%, ±5%, ±2%, or ±1% after implantation of the drug delivery device. In some embodiments, the stabilization and/or reduction in largest dimension of the tumor in this paragraph can be after the drug delivery device has completely dissolved in the patient, after the drug delivery device has partially dissolved in the patient, and/or after a portion of the drug delivery device (e.g., the API layer) has completely dissolved in the patient. In some embodiments, the largest dimensions of the tumor in this paragraph are stabilized and/or reduced after implantation of the drug delivery device without systemic chemotherapy. In some embodiments, the largest dimensions of the tumor in this paragraph are stabilized and/or reduced after implantation of the drug delivery device with systemic chemotherapy.

In some embodiments, a largest dimension of the tumor is reduced by at least about 1%, at least about 2%, at least about 3%, at least about 4%, at least about 5%, or at least about 10% two weeks after implantation of the drug delivery device. In some embodiments, a largest dimension of the tumor is reduced by about 1-10% or about 1-5% two weeks after implantation. In some embodiments, a largest dimension of the tumor is reduced by at least about 5%, at least about 8%, at least about 10%, at least about 12%, at least about 15%, or at least about 20% 9 weeks after implantation of the drug delivery device. In some embodiments, a largest dimension of the tumor is reduced by at least about 15%, at least about 20%, at least about 25%, at least about 30%, at least about 35%, at least about 40%, at least about 45%, at least about 50%, or at least about 50% 15 weeks after implantation of the drug delivery device. In some embodiments, a largest dimension of the tumor is reduced by at least about 15%, at least about 20%, at least about 25%, at least about 30%, at least about 35%, at least about 40%, at least about 45%, at least about 50%, or at least about 55% 23 weeks after implantation of the drug delivery device. In some embodiments, a largest dimension of the tumor is reduced by at least about 5%, at least about 8%, at least about 10%, at least about 11%, at least about 12%, at least about 15%, or at least about 20% between 2 weeks and 11 weeks from implantation of the drug delivery device. In some embodiments, the largest dimensions of the tumor in this paragraph are reduced after implantation of the drug delivery device without systemic chemotherapy. In some embodiments, the largest dimensions of the tumor in this paragraph are reduced after implantation of the drug delivery device with systemic chemotherapy.

In some embodiments, an anterior/posterior dimension orthogonal to the drug delivery device on the tumor is reduced by at least about 10%, at least about 15%, at least about 16%, at least about 20%, at least about 21%, at least about 25%, at least about 27%, at least about 30%, or at least about 35% after implantation of the drug delivery device. In some embodiments, an anterior/posterior dimension orthogonal to the drug delivery device on the tumor is reduced by at most about 100%, at most about 90%, at most about 75%, at most about 50%, at most about 40%, at most about 35%, at most about 30%, or at most about 25% after implantation of the drug delivery device. In some embodiments, the change in an anterior/posterior dimension orthogonal to the drug delivery device on the tumor can be within ±25%, ±20%, ±15%, ±10%, ±5%, ±2%, or ±1% after implantation of the drug delivery device. In some embodiments, the stabilization and/or reduction in an anterior/ posterior dimension orthogonal to the drug delivery device on the tumor in this paragraph can be after the drug delivery device has completely dissolved in the patient, after the drug delivery device has partially dissolved in the patient, and/or after a portion of the drug delivery device (e.g., the API layer) has completely dissolved in the patient. In some embodiments, an anterior/posterior dimension orthogonal to the drug delivery device on the tumor in this paragraph are stabilized and/or reduced after implantation of the drug delivery device without systemic chemotherapy. In some embodiments, an anterior/posterior dimension orthogonal to the drug delivery device on the tumor in this paragraph are stabilized and/or reduced after implantation of the drug delivery device with systemic chemotherapy.

In some embodiments, an anterior/posterior dimension orthogonal to the drug delivery device on the tumor is reduced by at least about 10%, at least about 15%, at least about 16%, at least about 20%, at least about 25%, at least about 27%, at least about 30%, or at least about 35% two weeks after implantation of the drug delivery device. In some embodiments an anterior/posterior dimension orthogonal to the drug delivery device on the tumor is reduced by at least about 10%, at least about 15%, at least about 16%, at least about 20%, at least about 25%, at least about 27%, at least about 30%, or at least about 35% 3 weeks after implantation of the drug delivery device. In some embodiments, an anterior/posterior dimension orthogonal to the drug delivery device on the tumor is reduced by about 5-40%, about 10-35%, about 15-30%, 20-30%, or about 25-30% 2 or 3 weeks after implantation of the drug delivery device. In some embodiments, an anterior/posterior dimension orthogonal to the drug delivery device on the tumor is reduced by at least about 10%, at least about 15%, at least about 16%, at least about 20%, at least about 21%, at least about 25%, at least about 27%, at least about 30%, or at least about 35% 9 weeks after implantation of the drug delivery device. In some embodiments, an anterior/posterior dimension orthogonal to the drug delivery device on the tumor is reduced by at least about 10%, at least about 15%, at least about 16%, at least about 20%, at least about 21%, at least about 25%, at least about 27%, at least about 30%, or at least about 35% 11 weeks after implantation of the drug delivery device. In some embodiments, an anterior/posterior dimension orthogonal to the drug delivery device on the tumor is reduced by at least about 10%, at least about 15%, at least about 16%, at least about 20%, at least about 21%, at least about 25%, at least about 27%, at least about 30%, or at least about 35% 15 weeks after implantation of the drug delivery device. In some embodiments, an anterior/posterior dimension orthogonal to the drug delivery device on the tumor is reduced by at least about 10%, at least about 15%, at least about 16%, at least about 20%, at least about 21%, at least about 25%, at least about 27%, at least about 30%, or at least about 35% 16 weeks after implantation of the drug delivery device. In some embodiments, an anterior/posterior dimension orthogonal to the drug delivery device on the tumor is reduced by at least about 10%, at least about 15%, at least about 16%, at least about 20%, at least about 21%, at least about 25%, at least about 27%, at least about 30%, or at least about 35% 17 weeks after implantation of the drug delivery device. In some embodiments, an anterior/posterior dimension orthogonal to the drug delivery device on the tumor is reduced by at least about 10%, at least about 15%, at least about 16%, at least about 20%, at least about 21%, at least about 25%, at least about 27%, at least about 30%, or at least about 35% 23 weeks after implantation of the drug delivery device. In some embodiments, an anterior/posterior dimension orthogonal to the drug delivery device on the tumor is reduced by at least about 10%, at least about 15%, at least about 16%, at least about 20%, at least about 21%, at least about 25%, at least about 27%, at least about 30%, or at least about 35% 24 weeks after implantation of the drug delivery device. In some embodiments, an anterior/posterior dimension orthogonal to the drug delivery device on the tumor in this paragraph are reduced after implantation of the drug delivery device without systemic chemotherapy. In some embodiments, an anterior/posterior dimension orthogonal to the drug delivery device on the tumor in this paragraph are reduced after implantation of the drug delivery device with systemic chemotherapy.

In some embodiments, an amount of CA 19-9 protein in the blood of a patient is reduced by at least about 20%, at least about 25%, at least about 28%, at least about 30%, or at least about 33%, at least about 35%, at least about 36%, or at least about 40% after implantation of the drug delivery device. In some embodiments, an amount of CA 19-9 protein in the blood of the patient is reduced by at most about 100%, at most about 75%, at most about 50%, at most about 40%, at most about 35%, or at most about 30% after implantation. In some embodiments, the change in the amount of CA 19-9 protein in the blood of a patient can be within ±25%, ±20%, ±15%, ±10%, ±5%, ±2%, or ±1% after implantation of the drug delivery device. In some embodiments, the stabilization and/or reduction in the amount of CA 19-9 protein in the blood of a patient in this paragraph can be after the drug delivery device has completely dissolved in the patient, after the drug delivery device has partially dissolved in the patient, and/or after a portion of the drug delivery device (e.g., the API layer) has completely dissolved in the patient. In some embodiments, the amount of CA 19-9 protein in the blood of a patient in this paragraph are stabilized and/or reduced after implantation of the drug delivery device without systemic chemotherapy. In some embodiments, the amount of CA 19-9 protein in the blood of a patient in this paragraph are stabilized and/or reduced after implantation of the drug delivery device with systemic chemotherapy.

In some embodiments, an amount of CA 19-9 protein in the blood of a patient is reduced by at least about 20%, at least about 25%, at least about 30%, or at least about 33% two weeks after implantation of the drug delivery device. In some embodiments, an amount of CA 19-9 protein in the blood of a patient is reduced by about 15-45%, about 20-40%, about 25-35%, or about 30-35% two weeks after implantation of the drug delivery device. In some embodiments, an amount of CA 19-9 protein in the blood of a patient is reduced by at least about 20%, at least about 25%, at least about 28%, at least about 30%, at least about 33%, at least about 35%, at least about 36%, or at least about 40% 3 weeks after from implantation of the drug delivery device. In some embodiments, the amount of CA 19-9 protein in the blood of a patient in this paragraph are reduced after implantation of the drug delivery device without systemic chemotherapy. In some embodiments, the amount of CA 19-9 protein in the blood of a patient in this paragraph are reduced after implantation of the drug delivery device with systemic chemotherapy.

In some embodiments, the methods of treating tissues (e.g., cancer) with the drug delivery devices disclosed herein can result in no serious adverse effects (SAEs). In some embodiments, the methods of treating tissues (e.g., cancer) with the drug delivery devices disclosed herein can result in no evidence of at least one selected from the group of pancreatitis, peritonitis, and infection. In some embodiments, the methods of treating tissues (e.g., cancer with the drug delivery devices disclosed herein can result in no detectable API from the drug delivery device in peripheral blood sampling of patients implanted with the drug delivery device. In some embodiments, the methods of treating tissues (e.g., cancer) with the drug delivery devices disclosed herein can elicit at least one of the following RECIST outcomes in a patient implanted with the drug delivery device: partial response, complete response, or stable disease. In some embodiments, the RECIST outcome can be after the drug delivery device has completely dissolved in the patient. In some embodiments, the RECIST outcome can be after the drug delivery device has partially dissolved in the patient. In some embodiments, the RECIST outcome can be at least about 1 month, at least about 2 months, at least about 3 months, at least about 6 months, at least about 9 months, or at least about a year after implantation of the drug delivery device.

Figure 57:
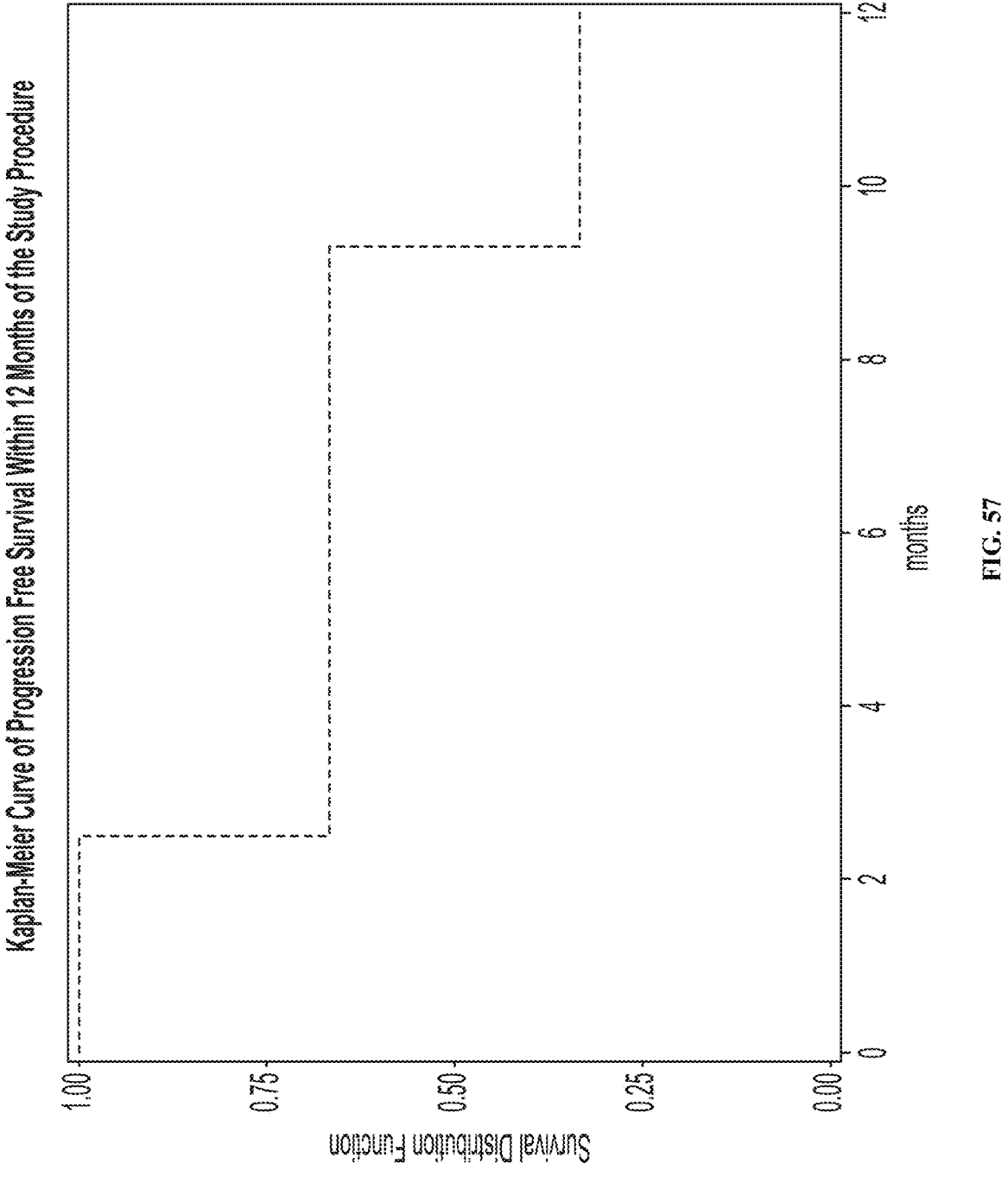
FIG. 57 illustrates a Kaplan-Meier Curve of Progression Free Survival within 12 months of the three patients from a clinical trial of a drug delivery device in accordance with some embodiments disclosed herein.

In some embodiments, the methods of treating tissues (e.g., cancer) with the drug delivery devices disclosed herein can result in no toxicity in the patient from the drug delivery device. In some embodiments, the methods of treating tissues with the drug delivery devices disclosed herein can result in at least one of the following in a patient implanted with the drug delivery device: improved quality of life, reduced pain, and local disease control. In some embodiments, the drug delivery device can increase progression-free survival (PFS) of the patient. FIG. 57 illustrates a Kaplan-Meier Curve of PFS within 12 months of the three patients from the clinical trial described above. This curve shows how likely it is that a patient survives without the tumor or cancer progressing since treatment begins with the drug delivery device (i.e., implantation of the drug delivery device) based on standard RECIST measurements to define progression of the tumor or cancer (e.g., increase of primary tumor and/or metastatic lesions per RECIST). As shown in FIG. 57, a patient has a ⅓ likelihood of progression free survival within 12 months of implantation of the drug delivery device. The first step in the Kaplan-Meier Curve around the 3 month mark was because one of the patients had a progression at that time and the second step around the 9 month mark is because one of the patients had a progression at that time, whereas the last patient did not show any signs of progression for the whole 12 months.

In some embodiments, there is at least about a 5% likelihood, at least about a 10% likelihood, at least about a 15% likelihood, at least about a 20% likelihood, at least about a 25%, at least about a 30% likelihood, at least about a ⅓ likelihood, at least about a 35% likelihood, at least about a 40% likelihood, at least about a 45% likelihood, at least about a 50% likelihood, at least about a 55% likelihood, at least about a 60% likelihood, at least about a 65% likelihood, or at least about a ⅔ likelihood of progression free survival within 12 months of implantation of the drug delivery device. In some embodiments, there is at least about a 25% likelihood, at least about a 30% likelihood, at least about a 35% likelihood, at least about a 40% likelihood, at least about a 45%, at least about a 50% likelihood, at least about a 55% likelihood, at least about a 60% likelihood, at least about a 65% likelihood, at least about a ⅔ likelihood, at least about a 70% likelihood, at least about a 75% likelihood, at least about a 80% likelihood, at least about a 85% likelihood, or at least about a 90% likelihood of progression free survival within 9 months of implantation of the drug delivery device. In some embodiments, at least about a 50% likelihood, at least about a 55% likelihood, at least about a 60% likelihood, at least about a 65% likelihood, at least about a ⅔ likelihood, at least about a 70% likelihood, at least about a 75% likelihood, at least about a 80% likelihood, at least about a 85% likelihood, at least about a 90% likelihood, at least a 95% likelihood, or at least a 100% likelihood of progression free survival within 3 months of implantation of the drug delivery device.

Figure 58:
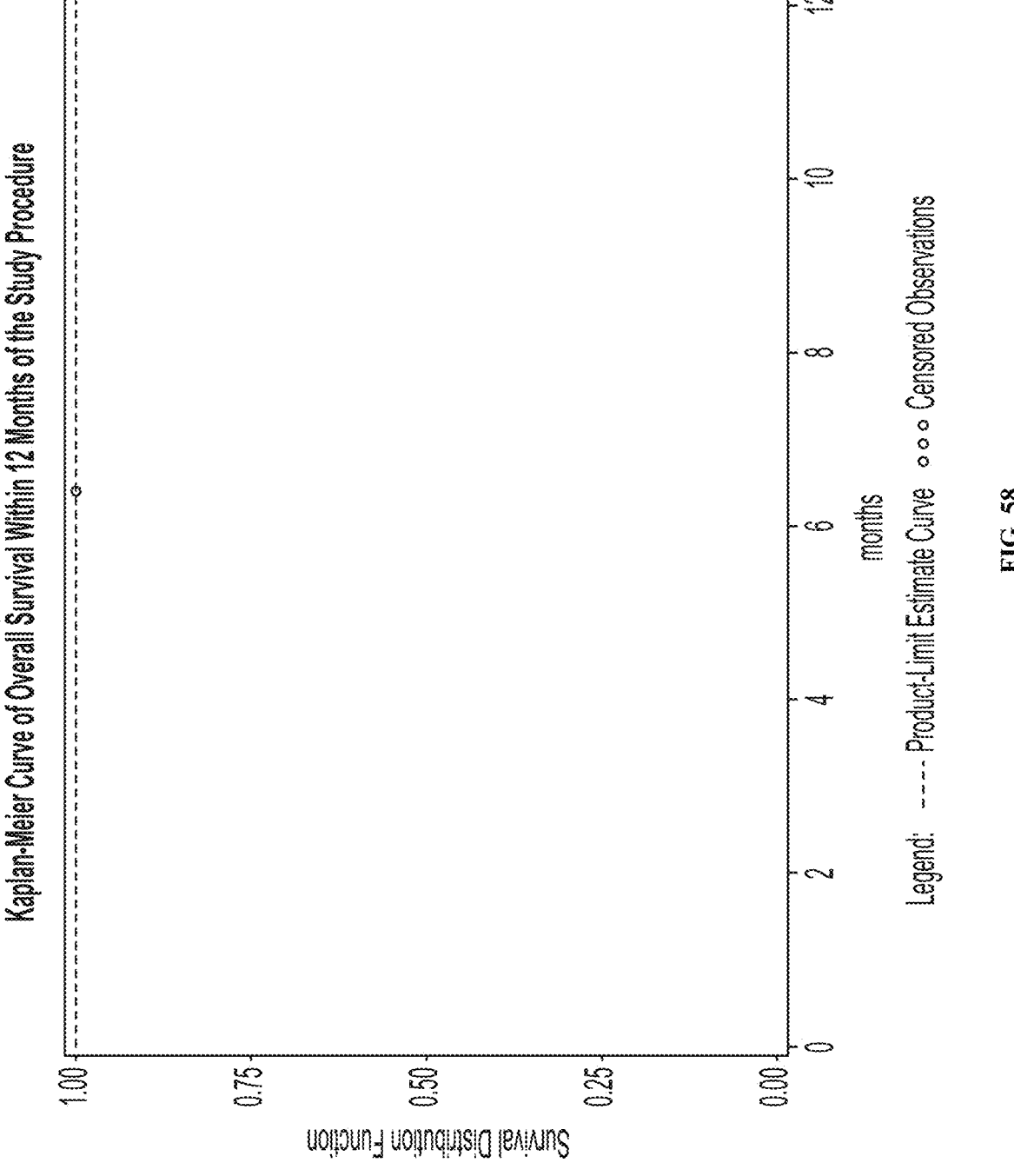
FIG. 58 illustrates a Kaplan-Meier Curve of Overall Survival within 12 months of the three patients from a clinical trial of a drug delivery device in accordance with some embodiments disclosed herein.

FIG. 58 illustrates a Kaplan-Meier Curve of Overall Survival within 12 months of the three patients from the clinical trial of a drug delivery device explained above. As shown in FIG. 58, the curve shows a 100% likelihood of survival within 12 months of implantation as all patients survived during the course of the study after implantation. There is a censored observation for one of the patients in FIG. 58 as that patient did not sign on for the long term 12 month follow up. Instead, that patient finished the 6 month study.

In some embodiments, the drug delivery device can convert a non-resectable tumor into a resectable tumor. In other words, the drug delivery device can increase the resection rate of the tumor. In some embodiments, the drug delivery device can downstage the disease (i.e., downstage the cancer). In some embodiments, the drug delivery device can increase the overall survival of the patient. In some embodiments, the drug delivery device can decrease the risk of metastasis of the patient. In some embodiments, the drug delivery device can prevent metastasis of the patient. In some embodiments, the drug delivery device can prevent metastasis through at least 6 months, at least 1 year, or at least 2 years.

In some embodiments, the drug delivery devices and methods disclosed herein can be used together with systemic chemotherapy, radiation therapy, and/or surgery. In some embodiments, the drug delivery devices and methods disclosed herein can improve tumor penetration of systemic chemotherapy in a patient. In some embodiments, systemic chemotherapy can be administered (or start being administered) after implantation (e.g., two weeks, 3 weeks, 4 weeks, etc. after implantation) of the drug delivery device. In some embodiments, systemic chemotherapy can be administered (or start being administered) at least 1 week, at least 2 weeks, at least 3 weeks, at least 4 weeks, at least 3 months, at least 6 months, or at least one year after implantation of the drug delivery device.

The drug delivery devices disclosed herein can change the route of administration to target just the area of interest, thereby increasing the amount of drug reaching the tumor with the aim to enhance therapeutic efficacy. As such, the drug delivery device can be applied in patients with PDAC: (i) pre-operatively as neoadjuvant treatment to control progression and downsize locally advanced and borderline anatomy to improve respectability; (ii) post-resection to reduce the rate of local recurrence; or (iii) in metastatic patient to control local progression and improve quality of life.

Additional Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Reference to "about" a value or parameter herein includes (and describes) variations that are directed to that value or parameter per se. For example, description referring to "about X" includes description of "X". In addition, reference to phrases "less than", "greater than", "at most", "at least", "less than or equal to", "greater than or equal to", or other similar phrases followed by a string of values or parameters is meant to apply the phrase to each value or parameter in the string of values or parameters. For example, a statement that a layer has a thickness of at least about 5 cm, about 10 cm, or about 15 cm is meant to mean that the layer has a thickness of at least about 5 cm, at least about 10 cm, or at least about 15 cm.

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of a pathological consequence of a cancer. The methods of the invention contemplate any one or more of these aspects of treatment.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The above description is presented to enable a person skilled in the art to make and use the disclosure, and is provided in the context of a particular application and its requirements. Various modifications to the preferred embodiments will be readily apparent to those skilled in the art, and the generic principles defined herein may be applied to other embodiments and applications without departing from the spirit and scope of the disclosure. Thus, this disclosure is not intended to be limited to the embodiments shown, but is to be accorded the widest scope consistent with the principles and features disclosed herein.

The invention claimed is:

1. A method of treating pancreatic cancer comprising:
   implanting a drug delivery device in a peritumoral area of the pancreas of a patient, wherein the drug delivery device comprises:
      a first layer comprising an active pharmaceutical ingredient (API), a first solvent, and at least 70 wt. % of a first biodegradable polymer; and
      a second layer on a side of the first layer, the second layer comprising a second solvent and at least 85 wt. % of a second biodegradable polymer;
   wherein the API is released from the drug delivery device into a tumor of the pancreas by in vivo degradation of the first biodegradable polymer.

2. The method of claim 1, further comprising administering systemic chemotherapy to the patient after implantation of the drug delivery device.

3. The method of claim 1, wherein the tumor is pancreatic ductal adenocarcinoma.

4. The method of claim 1, wherein the first layer comprises 7.5-11 wt. % of API.

5. The method of claim 4, wherein the API is paclitaxel.

6. The method of claim 1, wherein the first solvent comprises acetone and the first layer comprises 3-11 wt. % acetone.

7. The method of claim 6, wherein the second solvent comprises acetone and the second layer comprises 3-11 wt. % acetone.

8. The method of claim 1, wherein the first biodegradable polymer comprises poly(lactic-co-glycolic acid) (PLGA) 50:50 and the second biodegradable polymer comprises PLGA 75:25.

9. The method of claim 1, wherein the pancreatic cancer is non-immediately resectable pancreatic cancer, non-metastatic pancreatic cancer, borderline resectable pancreatic cancer, resectable pancreatic cancer, locally advanced pancreatic cancer, metastatic pancreatic cancer, or metastatic spread to the pancreas.

10. The method of claim 1, wherein the second biodegradable polymer has a slower degradation rate than the first biodegradable polymer.

11. The method of claim 1, wherein the first layer has an outer surface that is inset relative to an outer surface of the second layer.

12. The method of claim 11, wherein the second layer comprises an orientation identifier.

13. The method of claim 11, wherein the second layer comprises a rim extending beyond the outer surface of the first layer.

14. The method of claim 13, wherein the step of implanting the drug delivery device comprises attaching a suture to the rim of the second layer.

15. The method of claim 1, wherein the step of implanting the drug delivery device comprises placing the drug delivery device into a tubular shape, and inserting the drug delivery device in the tubular shape into a trocar.

16. The method of claim 15, wherein the step of implanting the drug delivery device comprises removing the drug delivery device from the trocar, flattening the drug delivery device from the tubular shape, and placing the drug delivery device onto the tumor.

\* \* \* \* \*